(12) United States Patent
Loussaert et al.

(10) Patent No.: US 7,834,245 B2
(45) Date of Patent: Nov. 16, 2010

(54) NITRATE REDUCTASES FROM RED ALGAE, COMPOSITIONS AND METHODS OF USE THEREOF

(75) Inventors: Dale F Loussaert, Clive, IA (US); Dennis O'Neill, Ankeny, IA (US); Carl R Simmons, Des Moines, IA (US); Haiyin Wang, Johnston, IA (US)

(73) Assignee: Pioneer Hi-Bred International, Inc, Johnston, IA (US)

( * ) Notice: Subject to any disclaimer, the term of this patent is extended or adjusted under 35 U.S.C. 154(b) by 95 days.

(21) Appl. No.: 12/138,477

(22) Filed: Jun. 13, 2008

(65) Prior Publication Data

US 2008/0313775 A1 Dec. 18, 2008

Related U.S. Application Data

(60) Provisional application No. 60/944,343, filed on Jun. 15, 2007.

(51) Int. Cl.
*A01H 1/00* (2006.01)
*C07H 21/04* (2006.01)
*C12N 15/29* (2006.01)
*C07K 14/415* (2006.01)

(52) U.S. Cl. .................. 800/295; 435/6; 435/69.1; 435/468; 435/419; 435/252.3; 435/320.1; 435/183; 530/370; 536/23.6; 800/278; 800/301

(58) Field of Classification Search .......... 435/6, 435/69.1, 468, 412, 415, 419, 320.1, 183; 530/370; 536/23.6; 800/278, 295, 320.1, 800/312

See application file for complete search history.

(56) References Cited

OTHER PUBLICATIONS

Goltz et al., GenEml Database, Accession No. AM270178, J. Biol. Chem., vol. 257, No. 18, pp. 11186-11190, 1982.*

Araki, S., et al.; "Some Enzymic Properties of Nitrate Reductase from *Porphyra yezoensis* UEDA f. narawaensis MIURA" Bulletin of the Japanese Society of Scientific Fisheries (1979) 45(7):919-924.

Chow, F., et al.; "In vitro assay and light regulation of nitrate reductase in red alga *Gracilaria chilensis*"; Journal of Plant Physiology (2004) 161:769-776; Elsevier Ltd.; Amsterdam, The Netherlands.

Nakamura, Y. and Ikawa, T., et al.; "Purification and Properties of NADH: Nitrate Reductase from the Red Alga *Porphyra yezoensis*"; Plant Cell Physiol (1993) 34(8):1239-1249; Oxford University Press, Oxford, UK.

Thomas, T.E. and Harrison, P.J.; "A Comparison of In Vitro and In Vivo Nitrate Reductase Assays in Three Intertidal Seaweeds"; Botanica Marina (1988) 31:101-107; Walter de Gruyter; Berlin, Germany.

* cited by examiner

*Primary Examiner*—Phuong T Bui

(57) ABSTRACT

The NR enzymes described herein were discovered in the red algae of *Porphyra perforata* (PpNR) and *Porphyra yezoensis* (PyNR). The present invention provides methods and compositions relating to altering NR activity, nitrogen utilization and/or uptake in plants. The invention relates to a method for the production of plants with maintained or increased yield under low nitrogen fertility. The invention provides isolated nitrate reductase (NR) nucleic acids and their encoded proteins. The invention further provides recombinant expression cassettes, host cells, and transgenic plants. Plants transformed with nucleotide sequences encoding the NR enzyme show improved properties, for example, increased yield and growth.

17 Claims, 6 Drawing Sheets

```
                 1                                                50
Pp-NR      (1)   MEAASGALSELRLEKGVKGWDPVKVPGRSSLKSTPIATPEGSLRGGSLYT
Py-NR      (1)   MEAASGALSELRLEKGVKGWDPVKVPSRSSLKSTPIATPEGSLRGGSLYT
Consensus  (1)   MEAASGALSELRLEKGVKGWDPVKVP RSSLKSTPIATPEGSLRGGSLYT
                 51                                               100
Pp-NR      (51)  ARSQH--AAGANDVMAANGVSASSTASGLSFAPSDGSGSGSGRVGWTELN
Py-NR      (51)  TRAADGGAAGANGGMAANGVSTSSTSSGLSFAPSGGSGSGSGRVGWTELN
Consensus  (51)    RA    AAGAN  MAANGVS SSTASGLSFAPS GSGSGSGRVGWTELN
                 101                                              150
Pp-NR      (99)  DALNAKLASKSTMLDKQHVADEVDDRDVKTPDNWIPRHPALIRLTGKHPF
Py-NR      (101) NALNAKLLSKSTMLDKQHVAEEVDDRDVKTPDNWIPRHPDLVRLTGKHPF
Consensus  (101)  ALNAKL SKSTMLDKQHVADEVDDRDVKTPDNWIPRHP LIRLTGKHPF
                 151                                              200
Pp-NR      (149) NCEAPLSMLVDQGFITPPSLHFVRNHGAAPQLSFDDHRLEVTGLVDTPLT
Py-NR      (151) NCEAPLSMLVDQGFITPPSLHFVRNHGAAPQLSFDDHRLEVSGLVDTPLT
Consensus  (151) NCEAPLSMLVDQGFITPPSLHFVRNHGAAPQLSFDDHRLEVSGLVDTPLT
                 201                                              250
Pp-NR      (199) LSMADILAMPSVTIPVTLTCAGNRRKEQNMTKQTIGFSWGAAATSCNFWT
Py-NR      (201) LSMEDILAMPSVTIPVTLTCAGNRRKEQNMTKQTIGFSWGAAATSCNFWT
Consensus  (201) LSM DILAMPSVTIPVTLTCAGNRRKEQNMTKQTIGFSWGAAATSCNFWT
                 251                                              300
Pp-NR      (249) GVRVRDVLQKAGIQMDKARHVCFVGCDNLPGGKYGTSVDLATAMDQFGEV
Py-NR      (251) GVRLRDVLEKAGIQMDKARHVCFVGCDDLPGGKYGTSIDLATAMDQFGEV
Consensus  (251) GVRLRDVL KAGIQMDKARHVCFVGCD LPGGKYGTSIDLATAMDQFGEV
                 301                                              350
Pp-NR      (299) MLAYEQNGIRLTPDHGAPLRVVIPGWIGGRMVKWVTGLSVTSEESQEHYH
Py-NR      (301) MLAYEQNGIRLTPDHGAPLRVVIPGWIGGRMVKWLTGVSVTAEESQEHYH
Consensus  (301) MLAYEQNGIRLTPDHGAPLRVVIPGWIGGRMVKWLTGVSVTAEESQEHYH
                 351                                              400
Pp-NR      (349) FFDNRILPPHVDAELAKSEGWWYKREYLFNQLNINSAISSPANGELMSLS
Py-NR      (351) FFDNRIMPPHVDAELAKSEGWWYKREYLFNQLNINSAISSPANGELMSLS
Consensus  (351) FFDNRILPPHVDAELAKSEGWWYKREYLFNQLNINSAISSPANGELMSLS
                 401                                              450
Pp-NR      (399) GAGVYTLKGYAYSGGGRKVTRVEVSVDGGKTWLLATLDHPEERHSHAPSY
Py-NR      (401) GAGVYTLKGYAYSGGGRKVTRVEVSVDGGKTWLLATLDHPEERHSHAPSY
Consensus  (401) GAGVYTLKGYAYSGGGRKVTRVEVSVDGGKTWLLATLDHPEERHSHAPSY
                 451                                              500
Pp-NR      (449) GRYYCWCFWEYTIDKFALLNAATSSGELLVRAWDEGNNTQPAKLTWNLMG
Py-NR      (451) GRYYCWCFWEYTIDKFALLNAATSSGELLVRAWDEGNNTQPAKLTWNLMG
Consensus  (451) GRYYCWCFWEYTIDKFALLNAATSSGELLVRAWDEGNNTQPAKLTWNLMG
                 501                                              550
Pp-NR      (499) MGNNCYFRVTVAPKQSSGEFALEFLHPTVAGPAEGGWMPPPQESVVAAAA
Py-NR      (501) MGNNCYFRVTVAPKQSSGEFVLEFLHPTVPGPAEGGWMPPPQESVVAAAA
Consensus  (501) MGNNCYFRVTVAPKQSSGEF LEFLHPTV GPAEGGWMPPPQESVVAAAA
                 551                                              600
Pp-NR      (549) AAAVAETLKRTKSAPQMNKMDQQDSKTITMEEVAKHDTEEDSWIVVHNKV
Py-NR      (551) AAVVAETLKRAKSAPQINKMDQEDTKTYTMEEVAKHDTEEDSWIVVHNKV
Consensus  (551) AA VAETLKR KSAPQINKMDQ DSKT TMEEVAKHDTEEDSWIVVHNKV
                 601                                              650
Pp-NR      (599) YDCTPFLKDHPGGGASIVMNAGADCTEEFDAIHSTKAKSMLDDYYIGELA
Py-NR      (601) YDCTPFLKDHPGGGASIVMNAGADCTEEFDAIHSTKAKGMLDDYYIGELA
Consensus  (601) YDCTPFLKDHPGGGASIVMNAGADCTEEFDAIHSTKAK MLDDYYIGELA
```

FIGURE 1A

```
              651                                                   700
   Pp-NR (649) VEDIEDEPEQPALHLSKSSVQLMKDDFKEQSVRKAVEGVDEEVVTPVALN
   Py-NR (651) IEDIEDEPEQPALHMSKSSVQLMKDDFKEQSVRKAVDDEEAAPVAPVALN
Consensus (651) IEDIEDEPEQPALHLSKSSVQLMKDDFKEQSVRKAVD  D   V PVALN
              701                                                   750
   Pp-NR (699) PKKWIHFPLIQKEELSHDTRRFRFGLPTPGHRLGLPVGFHMFLMATIDGA
   Py-NR (701) PKKWVHFPLIQKEELSHDTRRFRFGLPTEGHRLGLPVGFHMFLAATIEGS
Consensus (701) PKKWIHFPLIQKEELSHDTRRFRFGLPT GHRLGLPVGFHMFL ATIDGA
              751                                                   800
   Pp-NR (749) MVMRAYTPTSSDAELGYFDLVIKVYFANVHPRFPDGGKLTQYMEEMSLGD
   Py-NR (751) MVMRAYTPTSSDAQLGYFDLVIKVYFANVHPKFPGGGKLTQYMEEMSLGD
Consensus (751) MVMRAYTPTSSDA LGYFDLVIKVYFANVHPKFP GGKLTQYMEEMSLGD
              801                                                   850
   Pp-NR (799) EIRVKGPLGHIEYRSRGEMTIDGKPRTVSALTGLMAGSGITPFYQILQAV
   Py-NR (801) EIRVKDPLGHIEYRGRGEMTIDGKPRTVSALTGLMAGSGITPFYQILQAV
Consensus (801) EIRVK PLGHIEYR RGEMTIDGKPRTVSALTGLMAGSGITPFYQILQAV
              851                                                   900
   Pp-NR (849) MADPEDKTELYLIYANQTPEDVLLRSELDKMAAERDNIHVWYTCDRAPED
   Py-NR (851) MADPEDKTELYLIYANQTPEDVLLRSELDKMAAERDNIHVWYTCDRAPED
Consensus (851) MADPEDKTELYLIYANQTPEDVLLRSELDKMAAERDNIHVWYTCDRAPED
              901                                                   950
   Pp-NR (899) WKYDIGFMTVDMIKEHGAPAGPDVLGLSCGPPPFIKFAATPSLTKNGYAE
   Py-NR (901) WQFDIGFMTEKMIKEHGAPAGPDVLGLSCGPPPFIKFAATPSLTKNGYAE
Consensus (901) W FDIGFMT  MIKEHGAPAGPDVLGLSCGPPPFIKFAATPSLTKNGYAE
              951
   Pp-NR (949) ENQFLF
   Py-NR (951) EDQFLF
Consensus (951) E QFLF
```

FIGURE 1B

SEQUENCE LISTING

<160> NUMBER OF SEQ ID NOS: 34

<210> SEQ ID NO 1
<211> LENGTH: 2865
<212> TYPE: DNA
<213> ORGANISM: Porphyra perforata

<400> SEQUENCE: 1

```
atggaggctg cttctggtgc cctcagtgag ctccggttgg agaaggggt taagggctgg      60 gacccggtca aggtgcccgg ccggagctcc ctcaagagca cgcctatcgc caccccagag     120
ggctccctcc gcggtggctc cctctacacg gcccggtcgc agcacgcggc tggcgccaac     180
gacgtcatgg cggccaatgg ggtgtcggcg tcgagcaccg cgtcggggtt gagctttgct     240
ccttcggacg gcagtggcag tggcagtggc cgcgtcgggt ggacggagct gaacgatgct     300
ctgaacgcca agctcgcgtc caagtcgacg atgttggaca agcagcacgt tgcggacgag     360
gtggatgacc gggacgtcaa gacgccagac aactggatcc cccgccaccc ggccttgatc     420
cgtctgacgg gcaagcaccc gttcaactgt gaggcgccgc tgtcgatgct ggtggatcag     480
```

-continued

```
ggttttatca cccccccatc tctgcactttt gtgcgcaacc acggggctgc accgcagctg    540
tcttttgacg accaccggct ggaggtgacc ggcctcgtcg acactccttt gacgttgtcc    600
atggctgaca tcttggccat gccgagcgtc accatcccgg tcacgctgac gtgcgcggga    660
aaccggcgga aggagcagaa catgacaaag cagacgattg gcttctcgtg gggcgccgcc    720
gccaccagct gcaacttttg gactggcgtg cgcgtacggg atgtgcttca aaaggcgggc    780
atccagatgg acaaggcgcg ccatgtttgc tttgtgggct gtgacaacct gccgggggc     840
aagtacggca cgtcggttga cctggcgacg gccatggacc agttcgggga ggtgatgctt    900
gcgtacgagc agaacggcat ccgcctcacg cccgaccacg gcgcgcccct gcgggtggta    960
attcctgggt ggattggcgg ccgcatggtg aagtgggtga ccggcctgtc ggtaacgtcg    1020
gaagagtcgc aggagcacta tcactttttt gataaccgca tcctgccacc acacgtggac    1080
gcggagctgg ccaagtctga gggctggtgg tacaagcgcg agtacctgtt caaccagctc    1140
aatatcaact ctgccatcag ctctcctgcc aatggcgaac tgatgtccct gtcgggcgcg    1200
ggggtgtaca ccctcaaggg ttacgcctac tctggcggcg gccgcaaggt cacccgtgtg    1260
gaggtgtcgg tggacggcgg caagacttgg ctgctggcca cgttggacca ccccgaggag    1320
cggcactcgc acgctccgtc gtatggtcgc tattactgct ggtgcttctg ggagtacacc    1380
attgataagt ttgcgctgct caacgcgcg actagttcgg gcgagttgct ggtgcgtgcg     1440
tgggatgagg gcaacaatac ccagcccgcc aagctgacct ggaacttgat gggtatgggc    1500
aacaactgct acttccgcgt gacggtggcg cccaagcagt cgtcgggtga atttgcgctc    1560
gagtttctcc acccgacggt ggcgggcccc gcggagggtg gctggatgcc gccaccgcag    1620
gagtcggtag ttgcggctgc cgccgcgcg gcagtagcag agacactgaa gcggaccaaa     1680
tcggcgccgc agatgaacaa gatggaccag caggactcca agacgattac catggaggag    1740
gtggccaagc acgacacgga agaggactcg tggattgtgg tgcacaacaa ggtgtatgac    1800
tgtacgcctt tccttaagga ccaccccggt ggtggcgcca gcattgtgat gaacgcgggt    1860
gcggactgca cggaggagtt tgatgcgatc cactcaacca aggccaagtc catgctggac    1920
gactactata ttggcgaact ggccgttgag gacattgagg acgagccgga gcaaccagcc    1980
ctgcacctgt ccaagtcgtc ggtgcagctg atgaaggatg acttcaaaga gcagagcgtg    2040
cgtaaggctg tggagggtgt ggacgaggag gtcgtgacgc cggtggcact taaccccaag    2100
aagtggattc actttccgct catccagaag gaggagttga gccatgacac gcggcgcttc    2160
cgcttttgggc tccccactcc tggccaccgg ttgggcctgc ctgtgggctt ccacatgttc    2220
ttgatggcca ccattgacgg tgcaatggtc atgcgggcat acacaccgac gtcgtcggac    2280
gcagagctgg gctacttcga cctggtcatc aaggtgtact ttgcaaacgt gcaccccagg    2340
ttccctgacg gtggtaagct cacccagtac atggaggaga tgtcgctggg cgacgagatt    2400
cgcgtcaagg gcccgcttgg ccacattgag taccgtagcc gcggcgagat gaccattgac    2460
ggcaagccgc ggacggtaag tgccctgacg ggcctgatgg cggcagtgg catcacgccc     2520
ttttaccaga ttctccaggc tgtcatggcc gacccggagg acaagaccga gctgtacctc    2580
atctatgcca accagacacc ggaggatgtg ctgctgcgt cagagctgga caagatggcg     2640
gcagagcgcg acaacatcca tgtctggtac acatgcgacc gcgcgccgga ggactggaag    2700
tatgacattg gcttcatgac ggtagacatg atcaaggagc atggggcgcc ggcaggcccc    2760
gatgtgttgg gcctgtcgtg cggaccgccg ccatttatca gtttgcggc gaccccgagc     2820
```
ttgaccaaga acggctatgc ggaggagaac cagttcttgt tttag    2865

<210> SEQ ID NO 2
<211> LENGTH: 2865
<212> TYPE: DNA
<213> ORGANISM: Porphyra perforata

<400> SEQUENCE: 2

| | |
|---|---|
| atggaagctg ccagcggcgc tctttcggaa ctgcgcttgg agaagggtgt taagggctgg | 60 |
| gacccggtta aggttcctgg caggtcaagc ttgaagagca cgccatcgc tactcccgag | 120 |
| ggctcactcc gcggtggctc tctgtacaca gcgaggtcac acatgctgc gggcgctaat | 180 |
| gacgttatgg ctgccaatgg tgtctctgcg tcttctacgg ccagcgggct gtctttcgct | 240 |
| ccttccgatg gttccggtag cggtagcggt cgcgtgggtt ggaccgaact caatgatgcg | 300 |
| ctcaacgcta agctggcctc caagtccacc atgctcgata gcagcacgt ggcggacgag | 360 |
| gttgatgacc gggacgtgaa gactccggac aactggattc cgcgccatcc tgccctcatc | 420 |
| cgcctgaccg ggaagcatcc tttcaactgc gaggctccgc tgtccatgct ggtggatcaa | 480 |
| gggttcatca cgccgccgag cctccacttc gttaggaatc acgcgctgc tccgcagttg | 540 |
| tccttcgacg accaccgctt ggaggtgact ggccttgtgg acactccgct gactttgagc | 600 |
| atggccgata tccttgcgat gccgagcgtc actattcccg tgactcttac ctgcgctggc | 660 |
| aaccggcgga aggagcagaa catgaccaag cagacgatcg gcttctcgtg gggtgccgct | 720 |
| gcgacctctt gcaacttctg gactggcgtg agggtgcggg atgttcttca gaaggctggc | 780 |
| atccagatgg ataaggcccg ccacgtctgc ttcgttggct gtgacaatct cccgggtggc | 840 |
| aagtatggga cgtcggtgga cctggctacc gctatggacc agttcggcga ggtgatgctg | 900 |
| gcgtacgagc agaatggcat cgcctcacg ccagaccacg tgcccctct cgcgttgtt | 960 |
| atccctgggt ggattggcgg caggatggtt aagtgggtca caggcctcag cgtcactagc | 1020 |
| gaggagtccc aggagcacta ccacttcttc gacaaccgca tcttgccgcc tcacgtcgat | 1080 |
| gctgaacttg ccaagtccga aggctggtgg tacaagcgcg agtacctctt caaccagctc | 1140 |
| aacatcaaca gcgccatctc gagccctgcg aacggcgagc tcatgtcact ctcaggcgct | 1200 |
| ggcgtgtaca cccttaaggg ctacgcgtac tcaggtggcg gaggaaggt tacgagggtt | 1260 |
| gaggtcagcg ttgacggcgg taagacttgg cttctggcca ccctcgatca tccggaagag | 1320 |
| aggcactctc atgctccttc ctatggccgc tactactgct ggtgcttctg ggagtacacc | 1380 |
| attgacaagt tcgccctcct caacgcggcc acgtcctctg cgaactctt ggttcgcgct | 1440 |
| tgggacgaag ggaacaatac ccaacccgcg aagctcacct ggaacctgat gggcatgggc | 1500 |
| aacaactgct acttccgggt cacggtggcc ccgaagcagt cttccggcga gtttgcgctt | 1560 |
| gagtttcttc atcccaccgt tgctggccct gcagaaggcg ggtggatgcc tcctcctcaa | 1620 |
| gagtctgtgg ttgctgccgc tgctgctgcg gctgtggctc aaaccctgaa gcgcactaag | 1680 |
| gccgcgccgc agatgaacaa gatggaccag caggactcca agacgatcac gatggaggag | 1740 |
| gtcgctaagc atgacaccga ggaggactcc tggatcgtgg tgcacaacaa ggtctacgac | 1800 |
| tgcactccgt ttctcaagga ccaccctggc ggcggtgcca gcatcgtcat gaatgctggt | 1860 |
| gccgactgca cggaggaatt cgacgctatc cacagcacga aggccaagtc gatgctcgac | 1920 |
| gactactaca tcggcgagct ggccgttgag gacatagagg atgagcctga gcagccggct | 1980 |
| ctccacctct ccaagtcctc tgtgcagctc atgaaggacg acttcaagga gcagtccgtg | 2040 |
| cgcaaggctg ttgaaggcgt ggacgaagag gtcgtgactc ctgtggccct gaaccctaag | 2100 |

```
aagtggattc acttcccgct catccagaag gaggaactgt cccacgatac gaggcgcttc    2160
cggtttggcc tccctacacc tggtcatcgc cttgggctcc cggtgggctt ccatatgttc    2220
ctgatggcga ccatagacgg tgctatggtg atgagggcct acacgccgac ctcctctgat    2280
gcggagctgg gctacttcga tctcgtgatc aaggtctact tcgccaatgt ccacccgcgc    2340
ttcccggacg gcgtaagtt gacgcagtac atggaggaga tgtcgctggg cgacgagatc     2400
agggttaagg gtccgcttgg ccacatcgag taccgctccc gcggcgagat gaccattgat    2460
ggcaagccaa ggaccgtctc tgctctcact ggtctcatgg ccgggtcagg catcactccc    2520
ttctaccaga tcctccaagc cgtcatggct gacccagagg acaagaccga gctctacctg    2580
atctacgcca tcagacgcc cgaggacgtg ctcctgaggt cagagctgga caagatggcc     2640
gccgagcgcg ataacatcca cgtgtggtac acttgtgaca gggcgcctga ggactggaag    2700
tacgacatcg gcttcatgac ggtggacatg atcaaggagc atggtgctcc ggctggccca    2760
gatgttcttg gcctgtcttg cggtccacca cccttcatca agttcgccgc cactccaagc    2820
ctcaccaaga acggctacgc ggaggagaac cagttcctgt tctag                   2865

<210> SEQ ID NO 3
<211> LENGTH: 2865
<212> TYPE: DNA
<213> ORGANISM: Porphyra perforata

<400> SEQUENCE: 3
atggaagctg ccagcggcgc tctttcggaa ctgcgcttgg agaagggtgt taagggctgg      60
gacccggtta aggttcctgg caggtcaagc ttgaagagca cgcccatcgc tactcccgag     120
ggctcactcc gcggtggctc tctgtacaca gcgaggtcac aacatgctgc gggcgctaat    180
gacgttatgg ctgccaatgg tgtctctgcg tcttctacgg ccagcgggct gtctttcgct    240
ccttccgatg gttccggtag cggtagcggt cgcgtgggtt ggaccgaact caatgatgcg    300
ctcaacgcta agctggcctc caagtccacc atgctcgata gcagcacgt ggcggacgag     360 gttgatgacc gggacgtgaa gactccggac aactggattc cgcgccatcc tgccctcatc    420
cgcctgaccg ggaagcatcc tttcaactgc gaggctccgc tgtccatgct ggtggatcaa    480
gggttcatca cgccgccgag cctccacttc gttaggaatc acggcgctgc tccgcagttg    540
tccttcgacg accaccgctt ggaggtgact ggccttgtgg acactccgct gactttgagc    600
atggccgata tccttgcgat gccgagcgtc actattcccg tgactcttac ctgcgctggc    660
aaccggcgga aggagcagaa catgaccaag cagacgatcg gcttctcgtg gggtgccgct    720
gcgacctctt gcaacttctg gactggcgtg agggtgcggg atgttcttca gaaggctggc    780
atccagatgg ataaggcccg ccacgtctgc ttcgttggct gtgacaatct cccgggtggc    840
aagtatggga cgtcggtgga cctggctacc gctatggacc agttcggcga ggtgatgctg    900
gcgtacgagc agaatggcat tcgcctcacg ccagaccacg gtgcccctct tcgcgttgtt    960
atccctgggt ggattggcgg caggatggtt aagtgggtca caggcctcag cgtcactagc    1020
gaggagtccc aggagcacta ccacttcttc gacaaccgca tcttgccgcc tcacgtcgat    1080
gctgaacttg ccaagtccga aggctggtgg tacaagcgcg agtacctctt caaccagctc    1140
aacatcaaca gcgccatctc gagccctgcg aacggcgagc tcatgtcact ctcaggcgct    1200
ggcgtgtaca cccttaaggg ctacgcgtac tcaggtggcg ggaggaaggt tacgagggtt    1260
gaggtcagcg ttgacggcgg taagacttgg cttctggcca ccctcgatca tccggaagag    1320
```

```
aggcactctc atgctccttc ctatggccgc tactactgct ggtgcttctg ggagtacacc    1380
attgacaagt tcgccctcct caacgcggcc acgtcctctg cgaactctt  ggttcgcgct    1440 tgggacgaag ggaacaatac ccaacccgcg aagctcacct ggaacctgat gggcatgggc    1500
aacaactgct acttccgggt cacggtggcc ccgaagcagt cttccggcga gtttgcgctt    1560
gagtttcttc atcccaccgt tgctggccct gcagaaggcg ggtggatgcc tcctcctcaa    1620
gagtctgtgg ttgctgccgc tgctgctgcg gctgtggctg aaaccctgaa gcgcactaag    1680
gacgcgccgc agatgaacaa gatggaccag caggactcca agacgatcac gatggaggag    1740
gtcgctaagc atgacaccga ggaggactcc tggatcgtgg tgcacaacaa ggtctacgac    1800
tgcactccgt ttctcaagga ccaccctggc ggcggtgcca gcatcgtcat gaatgctggt    1860
gccgactgca cggaggaatt cgacgctatc cacagcacga aggccaagtc gatgctcgac    1920
gactactaca tcggcgagct ggccgttgag gacatagagg atgagcctga gcagccggct    1980
ctccacctct ccaagtcctc tgtgcagctc atgaaggacg acttcaagga gcagtccgtg    2040
cgcaaggctg ttgaaggcgt ggacgaagag gtcgtgactc ctgtggccct gaaccctaag    2100
aagtggattc acttcccgct catccagaag gaggaactgt cccacgatac gaggcgcttc    2160
cggtttggcc tccctacacc tggtcatcgc cttgggctcc cggtgggctt ccatatgttc    2220
ctgatggcga ccatagacgg tgctatggtg atgagggcct acacgccgac ctcctctgat    2280
gcggagctgg gctacttcga tctcgtgatc aaggtctact tcgccaatgt ccacccgcgc    2340
ttcccggacg gcggtaagtt gacgcagtac atggaggaga tgtcgctggg cgacgagatc    2400
agggttaagg gtccgcttgg ccacatcgag taccgctccc gcggcgagat gaccattgat    2460
ggcaagccaa ggaccgtctc tgctctcact ggtctcatgg ccgggtcagg catcactccc    2520
ttctaccaga tcctccaagc cgtcatggct gacccagagg acaagaccga gctctacctg    2580
atctacgcca atcagacgcc cgaggacgtg ctcctgaggt cagagctgga caagatggcc    2640
gccgagcgcg ataacatcca cgtgtggtac acttgtgaca gggcgcctga ggactggaag    2700
tacgacatcg gcttcatgac ggtggacatg atcaaggagc atggtgctcc ggctggccca    2760
gatgttcttg gcctgtcttg cggtccacca cccttcatca agttcgccgc cactccaagc    2820
ctcaccaaga acggctacgc ggaggagaac cagttcctgt tctag                    2865
```

<210> SEQ ID NO 4
<211> LENGTH: 2871
<212> TYPE: DNA
<213> ORGANISM: Porphyra yezoensis

<400> SEQUENCE: 4

```
atggaggccg cctcgggcgc cctcagcgag ctccggctgg agaaggggt  caagggctgg      60 gaccccgtca aggtgcccag ccggagctcc ctcaagagca ccccaattgc cacccccgag     120
ggctccctcc gcggcggctc tctgtatacg acccgcgcgg cagacggcgg ggcggcgggc     180
gccaacggcg gcatggcggc caatggggtg tccacgtcgt ccacttcgtc gggactgagc     240
tttgccccgt cggcggcag  cggcagcggc agcggccgcg ttgggtggac ggagctgaac     300
aacgcgctca cgccaagct  cctgtccaag tcgacgatgc tggacaagca gcacgttgcg     360
gaggaggtgg acgaccggga cgtgaagacg ccagacaact ggatccccg  ccacccggat     420 ttggtccggc tgacgggcaa gcacccgttc aactgtgagg cgccgctgtc catgctagta     480
gaccagggct tcatcacccc ccgtcgctg  cactttgtac gcaaccatgg ggcggcgccg     540
cagttgtcgt ttgacgacca ccggctggag gtgagcggcc tcgtcgacac ccccctgact     600
```

```
ctttccatgg aagacatttt ggccatgcca agcgtcacca tcccagtgac gctgacgtgc      660
gcaggcaacc ggcggaagga gcagaatatg acaaagcaga ccattggttt ctcgtggggc      720
gccgcggcta ctagctgcaa cttttggacg ggcgtgcgcc tgcggatgt gctcgagaag       780
gcggcatcc agatggacaa ggcccgtcat gtgtgctttg tgggctgtga cgacctgcct       840
ggtggcaagt acggcacatc gattgacctg gcgacggcca tggatcagtt tggggaggtg      900
atgctcgcgt acgagcagaa tggcatccgc ctgacgcccg accatggcgc gccctgcgg       960
gtggtgattc cagggtggat tggcggccgg atggtcaagt ggctgacggg cgtgtcggtg     1020
acagctgagg agtcacagga gcactaccac ttctttgaca accgtatcat gccgcctcac     1080
gttgacgcgg agctggccaa gtcggagggc tggtggtaca gcgggagta cctgttcaac      1140
cagctgaaca ttaactctgc catcagctcc cctgccaatg gggagctgat gtccctgtcg     1200
ggcgcggggg tgtacaccct gaagggctac gcctactctg gcgtgcggccg taaggtgacc     1260
cgcgtggagg tgtcggtgga cggcggtaag acgtggttgc tggccaccctt ggaccaccct    1320
gaggagcgtc actctcacgc tccctcgtat ggccgctatt actgctggtg cttctgggag     1380
tacaccattg acaagtttgc cctgctaaac gcggcaacca gctcgggcga gctgctagtg     1440
cgcgcatggg acgagggcaa caacacccag cccgccaagc tgacctggaa cctgatgggc     1500
atgggcaaca actgctactt ccgtgtgacg gtggcaccta agcagtcgtc gggtgaattc     1560
gtgcttgaat ttctgcaccc gacggtgccc ggccccgcgg agggtggctg gatgcccca       1620
ccacaggagt cggtggtggc ggccgccgct gcggcagtgg tggcggagac gcttaagcgg     1680
gcgaagtcgg cgccgcagat caacaagatg gaccaggagg acaccaagac ttacaccatg     1740
gaggaggtgg ccaagcacga cacggaggag gactcttgga ttgtggtgca caacaaggtg     1800
tatgattgca caccttcct caaggaccac cctggtggcg cgccagtat tgtgatgaac        1860
gcgggtgccg actgcacaga ggagttcgac gcgattcact caaccaaggc caagggcatg     1920
ctggacgact attacattgg tgagctggcc atcgaggaca ttgaggacga gccggagcag     1980
ccagctctgc acatgtccaa atcgtctgtg cagctgatga aggatgactt caaggagcag     2040
agcgtccgca aggccgtgga cgatgaggaa gcagcacccg tggcgcctgt ggctctcaac     2100
cccaagaagt gggttcactt cccgctcatc cagaaggagg agctgagcca cgacacccgg     2160
cgcttccgct ttgggctccc tacagagggt caccggctgg gcttgcccgt cggcttccac     2220
atgttcctgg ccgctaccat cgaaggctcc atggtcatgc gggcctacac gccaacgtcg     2280
tcggacgcac agctggggta cttttgacctg gtcatcaagg tgtactttgc caacgtgcac     2340
cccaagttcc ctggcggtgg caagctcacc cagtacatgg aggagatgtc tcttggcgac     2400
gagattcgcg tgaaggaccc gctcggccac attgagtacc gcggccgcgg tgagatgacg     2460
attgacggca gccgcgcac ggtcagcgcc ctgacaggcc tgatggcggg gagcggcatc       2520
acccccttttt accagatcct gcaggctgtc atggcggacc cagaggataa gaccgagctg    2580
tacctcatct atgccaacca gacaccggag gacgtgctgc tgcggtcaga gctggataag     2640
atggcagcgg agcgcgacaa catccacgtt tggtacacgt gcgaccgcgc accagaggac     2700
tggcagtttg acattggctt catgaccgag aagatgatca aggagcatgg ggcgccggcg     2760
ggccccgacg tgctgggcct gtcgtgcgga ccaccgccat ttatcaagtt tgcggcgacc     2820
ccaagcctga ccaagaatgg ctacgcggag gaggaccagt cctgttccta a              2871
```

<210> SEQ ID NO 5

<211> LENGTH: 2871
<212> TYPE: DNA
<213> ORGANISM: Porphyra yezoensis

<400> SEQUENCE: 5

```
atggaggccg cttctggcgc tctcagcgag ctccgcctcg agaagggtgt gaagggctgg      60
gaccctgtga aggtgccgag ccgcagcagc ctcaagagca ctccgatcgc cacaccggag     120
ggtagcctca gaggcggcag cctctatacc actcgcgctg ccgacggtgg tgccgctggc     180
gctaatggcg gtatggctgc caacggcgtg agcaccagca gcactagcag cggcttgagc     240
ttcgccccta gcgcggttc tggtagcggt agcggtagda tgggctggac cgagctcaac     300
aacgccctca cgccaagct cctcagcaag agcaccatgc tcgacaagca gcacgtggcc     360
gaggaggtgg acgaccgcga cgttaagacc ccggacaact ggattcctcg gcatccggac     420
cttgtgcgcc tcacaggcaa gcacccgttc aactgcgagg ctccgctcag catgctcgtg     480
gaccagggct tcatcacacc gccgagcctc catttcgttc gcaaccacgg cgccgctcct     540
cagctcagct tcgacgacca ccggctcgag gtgagcggtc tcgtggacac tccgctcacc     600
ctcagcatgg aggacatcct cgccatgccg agcgtgacca ttcccgtgac cctcacttgc     660
gccggcaacc gccgcaagga gcagaacatg accaagcaga ccatcggctt cagctggggc     720
gctgccgcta ccagctgcaa cttctggaca ggtgtgcgct gcgcgacgt tctcgagaag     780 gctggcattc agatggacaa ggcccgccac gtgtgcttcg tgggctgcga cgaccttccg     840
ggcggcaagt acggcaccag catcgacctc gccactgcta tggaccagtt cggcgaggtg     900
atgctcgcct acgagcagaa cggcatccgc cttactcctg atcacggcgc tccgcttcgc     960
gtggttatcc ctggttggat tggcggccgc atggtgaagt ggctcaccgg cgtgagcgtg    1020
accgccgagg agagccagga gcactaccac ttcttcgaca accggatcat gccgccgcac    1080
gtggatgccg agctcgccaa gtctgagggc tggtggtaca agcgcgagta cctcttcaac    1140
cagctcaaca tcaacagcgc catcagcagc ccggccaatg cgagctcat gagcctcagc     1200 ggtgccggcg tgtacaccct caagggctat gcttacagcg gtgcggcag aaaggtgacg    1260 cgcgttgagg tgagcgtgga cggcggtaag acttggctcc tcgctaccct cgatcacccg    1320
gaggagcgcc acagccacgc tccaagctac ggccgctact actgctggtg cttctgggag    1380
tacaccatcg acaagttcgc cctcctcaac gccgccacat ctagcggcga gctcctcgtt    1440
cgggcctggg atgagggtaa caacacccag ccggccaagc tcacctggaa cttgatgggc    1500
atgggcaaca actgctactt ccgcgtgacc gtggctccaa agcagagcag cggcgagttc    1560
gtgcttgagt tcctccaccc gactgtgccg ggtcctgcag agggtggttg gatgcctccg    1620
ccgcaggaga gcgttgtggc cgctgctgct gccgctgttg tggccgagac cttgaagcgg    1680
gccaaggccg ccccgcagat caacaagatg gaccaggagg acaccaagac ctacactatg    1740
gaggaggtgg ctaagcacga caccgaggag acagctgga tcgtggtgca acaacaaggtg     1800 tacgactgca ccccgttcct caaggaccac ccgggtggcg gcgcctctat tgtgatgaac    1860
gccggcgctg actgcactga ggagttcgac gccatccaca gcaccaaggc caagggcatg    1920
ctcgacgact actacatcgg cgagctcgcc atcgaggaca tcgaggacga gccggagcag    1980
ccggccctcc acatgtctaa gagcagcgtg cagctcatga aggacgactt caaggagcag    2040
agcgtgcgca aggccgtgga cgatgaggag gctgccccag tggctccggt ggccttgaat    2100
ccgaagaagt gggtgcactt cccgctcatc cagaaggagg agctcagcca cgacacacgc    2160
cgctttcggt ttggtctccc aaccgagggc caccgccttg gcctcccggt tggctttcat    2220
```

```
atgttcctcg ccgccaccat cgagggcagc atggtgatgc gcgcctacac accgaccagc    2280
agcgatgccc agctcggcta cttcgacctc gtgatcaagg tgtacttcgc caacgtgcac    2340
cctaagttcc ctggtggcgg caagctcacc cagtacatgg aggagatgag cctcggcgac    2400
gagatccgcg tgaaggaccc actcggccat atcgagtatc gcggtcgcgg cgagatgacc    2460
attgatggca gccgcgcac tgtgagcgcc ctcaccggcc tcatggctgg tagcggcatc    2520
accccgttct accagatcct ccaggcggtg atggccgacc cggaggacaa gaccgagctc    2580
tacctcatct acgccaacca gaccccggag gacgtgctcc ttcgcagcga gctcgacaag    2640
atggccgccg agcgcgacaa cattcacgtg tggtacacct gcgaccgcgc tcctgaggac    2700
tggcagttcg acatcggctt catgaccgag aagatgatca aggagcacgg cgctcctgcc    2760
ggcccagatg tgcttggtct cagctgcggc cctccgcctt tcatcaagtt cgccgccact    2820
ccgagcctca ccaagaacgg ctacgccgag gaggaccagt cctcttccta g             2871
```

<210> SEQ ID NO 6
<211> LENGTH: 2871
<212> TYPE: DNA
<213> ORGANISM: Porphyra yezoensis

<400> SEQUENCE: 6

```
atggaggccg cttctggcgc tctcagcgag ctccgcctcg agaagggtgt gaagggctgg     60
gaccctgtga aggtgccgag ccgcagcagc ctcaagagca ctccgatcgc cacaccggag    120
ggtagcctca gaggcggcag cctctatacc actcgcgctg ccgacggtgg tgccgctggc    180
gctaatggcg gtatggctgc caacggcgtg agcaccagca gcactagcag cggcttgagc    240
ttcgccccta gcgcggttc tggtagcggt agcggtagag tgggctggac cgagctcaac    300
aacgccctca cgccaagct cctcagcaag agcaccatgc tcgacaagca gcacgtggcc    360
gaggaggtgg acgaccgcga cgttaagacc ccggacaact ggattcctcg gcatccggac    420
cttgtgcgcc tcacaggcaa gcacccgttc aactgcgagg ctccgctcag catgctcgtg    480
gaccagggct tcatcacacc gccgagcctc catttcgttc gcaaccacgg cgccgctcct    540
cagctcagct tcgacgacca ccggctcgag gtgagcggtc tcgtggacac tccgctcacc    600
ctcagcatgg aggacatcct cgccatgccg agcgtgacca ttcccgtgac cctcacttgc    660
gccggcaacc gccgcaagga gcagaacatg accaagcaga ccatcggctt cagctggggc    720
gctgccgcta ccagctgcaa cttctggaca ggtgtgcgct gcgcgacgt tctcgagaag    780 gctggcattc agatggacaa ggcccgccac gtgtgcttcg tgggctgcga cgaccttccg    840
ggcggcaagt acggcaccag catcgacctc gccactgcta tggaccagtt cggcgaggtg    900
atgctcgcct acgagcagaa cggcatccgc cttactcctg atcacggcgc tccgcttcgc    960
gtggttatcc ctggttggat tggcggccgc atggtgaagt ggctcaccgg cgtgagcgtg   1020
accgccgagg agagccagga gcactaccac ttcttcgaca ccggatcat gccgccgcac   1080 gtggatgccg agctcgccaa gtctgagggc tggtggtaca agcgcgagta cctcttcaac   1140
cagctcaaca tcaacagcgc catcagcagc ccggccaatg gcgagctcat gagcctcagc   1200 ggtgccggc tgtacaccct caagggctat gcttacagcg gtggcggcag aaaggtgacg   1260
cgcgttgagg tgagcgtgga cggcggtaag acttggctcc tcgctaccct cgatcacccg   1320
gaggagcgcc acagccacgc tccaagctac ggccgctact actgctggtg cttctgggag   1380
tacaccatcg acaagttcgc cctcctcaac gccgccacat ctagcggcga gctcctcgtt   1440
```

-continued

```
cgggcctggg atgagggtaa caacacccag ccggccaagc tcacctggaa cttgatgggc      1500
atgggcaaca actgctactt ccgcgtgacc gtggctccaa agcagagcag cggcgagttc      1560
gtgcttgagt tcctccaccc gactgtgccg ggtcctgcag agggtggttg gatgcctccg      1620
ccgcaggaga gcgttgtggc cgctgctgct gccgctgttg tggccgagac cttgaagcgg      1680
gccaaggacg ccccgcagat caacaagatg gaccaggagg acaccaagac ctacactatg      1740
gaggaggtgg ctaagcacga caccgaggag acagctggac tcgtggtgca caacaaggtg      1800
tacgactgca ccccgttcct caaggaccac ccgggtggcg cgcctctat tgtgatgaac       1860 gccggcgctg actgcactga ggagttcgac gccatccaca gcaccaaggc caagggcatg      1920
ctcgacgact actacatcgg cgagctcgcc atcgaggaca tcgaggacga gccggagcag      1980
ccggccctcc acatgtctaa gagcagcgtg cagctcatga aggacgactt caaggagcag      2040
agcgtgcgca aggccgtgga cgatgaggag gctgccccag tggctccggt ggccttgaat      2100
ccgaagaagt gggtgcactt cccgctcatc cagaaggagg agctcagcca cgacacacgc      2160
cgctttcggt ttggtctccc aaccgagggc caccgccttg gcctcccggt tggctttcat      2220
atgttcctcg ccgccaccat cgagggcagc atggtgatgc cgcctacac accgaccagc       2280 agcgatgccc agctcggcta cttcgacctc gtgatcaagg tgtacttcgc caacgtgcac      2340
cctaagttcc ctggtggcgg caagctcacc cagtacatgg aggagatgag cctcggcgac      2400
gagatccgcg tgaaggaccc actcggccat atcgagtatc gcggtcgcgg cgagatgacc      2460
attgatggca gccgcgcac tgtgagcgcc ctcaccggcc tcatggctgg tagcggcatc       2520
accccgttct accagatcct ccaggcggtg atggccgacc cggaggacaa gaccgagctc      2580
tacctcatct acgccaacca gaccccggag gacgtgctcc ttcgcagcga gctcgacaag      2640
atggccgccg agcgcgacaa cattcacgtg tggtacacct gcgaccgcgc tcctgaggac      2700 tgcagttcg acatcggctt catgaccgag aagatgatca aggagcacgg cgctcctgcc       2760
ggcccagatg tgcttggtct cagctgcggc cctccgcctt tcatcaagtt cgccgccact      2820
ccgagcctca ccaagaacgg ctacgccgag gaggaccagt cctcttcta g               2871
```

<210> SEQ ID NO 7
<211> LENGTH: 954
<212> TYPE: PRT
<213> ORGANISM: Porphyra perforata

<400> SEQUENCE: 7

```
Met Glu Ala Ala Ser Gly Ala Leu Ser Glu Leu Arg Leu Glu Lys Gly
 1               5                  10                  15

Val Lys Gly Trp Asp Pro Val Lys Val Pro Gly Arg Ser Ser Leu Lys
            20                  25                  30

Ser Thr Pro Ile Ala Thr Pro Glu Gly Ser Leu Arg Gly Gly Ser Leu
        35                  40                  45

Tyr Thr Ala Arg Ser Gln His Ala Ala Gly Ala Asn Asp Val Met Ala
    50                  55                  60

Ala Asn Gly Val Ser Ala Ser Thr Ala Ser Gly Leu Ser Phe Ala
65                  70                  75                  80

Pro Ser Asp Gly Ser Gly Ser Gly Ser Gly Arg Val Gly Trp Thr Glu
                85                  90                  95

Leu Asn Asp Ala Leu Asn Ala Lys Leu Ala Ser Lys Ser Thr Met Leu
            100                 105                 110

Asp Lys Gln His Val Ala Asp Glu Val Asp Asp Arg Asp Val Lys Thr
        115                 120                 125
```

```
Pro Asp Asn Trp Ile Pro Arg His Pro Ala Leu Ile Arg Leu Thr Gly
130                 135                 140

Lys His Pro Phe Asn Cys Glu Ala Pro Leu Ser Met Leu Val Asp Gln
145                 150                 155                 160

Gly Phe Ile Thr Pro Pro Ser Leu His Phe Val Arg Asn His Gly Ala
                165                 170                 175

Ala Pro Gln Leu Ser Phe Asp Asp His Arg Leu Glu Val Thr Gly Leu
            180                 185                 190

Val Asp Thr Pro Leu Thr Leu Ser Met Ala Asp Ile Leu Ala Met Pro
        195                 200                 205

Ser Val Thr Ile Pro Val Thr Leu Thr Cys Ala Gly Asn Arg Arg Lys
210                 215                 220

Glu Gln Asn Met Thr Lys Gln Thr Ile Gly Phe Ser Trp Gly Ala Ala
225                 230                 235                 240

Ala Thr Ser Cys Asn Phe Trp Thr Gly Val Arg Val Arg Asp Val Leu
                245                 250                 255

Gln Lys Ala Gly Ile Gln Met Asp Lys Ala Arg His Val Cys Phe Val
            260                 265                 270

Gly Cys Asp Asn Leu Pro Gly Gly Lys Tyr Gly Thr Ser Val Asp Leu
        275                 280                 285

Ala Thr Ala Met Asp Gln Phe Gly Glu Val Met Leu Ala Tyr Glu Gln
    290                 295                 300

Asn Gly Ile Arg Leu Thr Pro Asp His Gly Ala Pro Leu Arg Val Val
305                 310                 315                 320

Ile Pro Gly Trp Ile Gly Gly Arg Met Val Lys Trp Val Thr Gly Leu
                325                 330                 335

Ser Val Thr Ser Glu Glu Ser Gln Glu His Tyr His Phe Phe Asp Asn
            340                 345                 350

Arg Ile Leu Pro Pro His Val Asp Ala Glu Leu Ala Lys Ser Glu Gly
        355                 360                 365

Trp Trp Tyr Lys Arg Glu Tyr Leu Phe Asn Gln Leu Asn Ile Asn Ser
    370                 375                 380

Ala Ile Ser Ser Pro Ala Asn Gly Glu Leu Met Ser Leu Ser Gly Ala
385                 390                 395                 400

Gly Val Tyr Thr Leu Lys Gly Tyr Ala Tyr Ser Gly Gly Arg Lys
                405                 410                 415

Val Thr Arg Val Glu Val Ser Val Asp Gly Gly Lys Thr Trp Leu Leu
            420                 425                 430

Ala Thr Leu Asp His Pro Glu Glu Arg His Ser His Ala Pro Ser Tyr
        435                 440                 445

Gly Arg Tyr Tyr Cys Trp Cys Phe Trp Glu Tyr Thr Ile Asp Lys Phe
    450                 455                 460

Ala Leu Leu Asn Ala Ala Thr Ser Ser Gly Glu Leu Leu Val Arg Ala
465                 470                 475                 480

Trp Asp Glu Gly Asn Asn Thr Gln Pro Ala Lys Leu Thr Trp Asn Leu
                485                 490                 495

Met Gly Met Gly Asn Asn Cys Tyr Phe Arg Val Thr Val Ala Pro Lys
            500                 505                 510

Gln Ser Ser Gly Glu Phe Ala Leu Glu Phe Leu His Pro Thr Val Ala
        515                 520                 525

Gly Pro Ala Glu Gly Gly Trp Met Pro Pro Gln Glu Ser Val Val
    530                 535                 540
```

```
Ala Ala Ala Ala Ala Ala Val Ala Glu Thr Leu Lys Arg Thr Lys
545                 550                 555                 560

Ser Ala Pro Gln Met Asn Lys Met Asp Gln Asp Ser Lys Thr Ile
                565                 570                 575

Thr Met Glu Glu Val Ala Lys His Asp Thr Glu Glu Asp Ser Trp Ile
            580                 585                 590

Val Val His Asn Lys Val Tyr Asp Cys Thr Pro Phe Leu Lys Asp His
        595                 600                 605

Pro Gly Gly Gly Ala Ser Ile Val Met Asn Ala Gly Ala Asp Cys Thr
    610                 615                 620

Glu Glu Phe Asp Ala Ile His Ser Thr Lys Ala Lys Ser Met Leu Asp
625                 630                 635                 640

Asp Tyr Tyr Ile Gly Glu Leu Ala Val Glu Asp Ile Glu Asp Glu Pro
                645                 650                 655

Glu Gln Pro Ala Leu His Leu Ser Lys Ser Ser Val Gln Leu Met Lys
                660                 665                 670

Asp Asp Phe Lys Glu Gln Ser Val Arg Lys Ala Val Glu Gly Val Asp
        675                 680                 685

Glu Glu Val Val Thr Pro Val Ala Leu Asn Pro Lys Lys Trp Ile His
        690                 695                 700

Phe Pro Leu Ile Gln Lys Glu Leu Ser His Asp Thr Arg Arg Phe
705                 710                 715                 720

Arg Phe Gly Leu Pro Thr Pro Gly His Arg Leu Gly Leu Pro Val Gly
                725                 730                 735

Phe His Met Phe Leu Met Ala Thr Ile Asp Gly Ala Met Val Met Arg
            740                 745                 750

Ala Tyr Thr Pro Thr Ser Ser Asp Ala Glu Leu Gly Tyr Phe Asp Leu
            755                 760                 765

Val Ile Lys Val Tyr Phe Ala Asn Val His Pro Arg Phe Pro Asp Gly
    770                 775                 780

Gly Lys Leu Thr Gln Tyr Met Glu Glu Met Ser Leu Gly Asp Glu Ile
785                 790                 795                 800

Arg Val Lys Gly Pro Leu Gly His Ile Glu Tyr Arg Ser Arg Gly Glu
                805                 810                 815

Met Thr Ile Asp Gly Lys Pro Arg Thr Val Ser Ala Leu Thr Gly Leu
            820                 825                 830

Met Ala Gly Ser Gly Ile Thr Pro Phe Tyr Gln Ile Leu Gln Ala Val
            835                 840                 845

Met Ala Asp Pro Glu Asp Lys Thr Glu Leu Tyr Leu Ile Tyr Ala Asn
850                 855                 860

Gln Thr Pro Glu Asp Val Leu Leu Arg Ser Glu Leu Asp Lys Met Ala
865                 870                 875                 880

Ala Glu Arg Asp Asn Ile His Val Trp Tyr Thr Cys Asp Arg Ala Pro
                885                 890                 895

Glu Asp Trp Lys Tyr Asp Ile Gly Phe Met Thr Val Asp Met Ile Lys
            900                 905                 910

Glu His Gly Ala Pro Ala Gly Pro Asp Val Leu Gly Leu Ser Cys Gly
            915                 920                 925

Pro Pro Pro Phe Ile Lys Phe Ala Ala Thr Pro Ser Leu Thr Lys Asn
    930                 935                 940

Gly Tyr Ala Glu Glu Asn Gln Phe Leu Phe
945                 950
```

<210> SEQ ID NO 8
<211> LENGTH: 954
<212> TYPE: PRT
<213> ORGANISM: Porphyra perforata

<400> SEQUENCE: 8

```
Met Glu Ala Ala Ser Gly Ala Leu Ser Glu Leu Arg Leu Glu Lys Gly
 1               5                  10                  15

Val Lys Gly Trp Asp Pro Val Lys Val Pro Gly Arg Ser Ser Leu Lys
            20                  25                  30

Ser Thr Pro Ile Ala Thr Pro Glu Gly Ser Leu Arg Gly Gly Ser Leu
        35                  40                  45

Tyr Thr Ala Arg Ser Gln His Ala Ala Gly Ala Asn Asp Val Met Ala
    50                  55                  60

Ala Asn Gly Val Ser Ala Ser Ser Thr Ala Ser Gly Leu Ser Phe Ala
65                  70                  75                  80

Pro Ser Asp Gly Ser Gly Ser Gly Ser Gly Arg Val Gly Trp Thr Glu
                85                  90                  95

Leu Asn Asp Ala Leu Asn Ala Lys Leu Ala Ser Lys Ser Thr Met Leu
            100                 105                 110

Asp Lys Gln His Val Ala Asp Glu Val Asp Asp Arg Asp Val Lys Thr
        115                 120                 125

Pro Asp Asn Trp Ile Pro Arg His Pro Ala Leu Ile Arg Leu Thr Gly
    130                 135                 140

Lys His Pro Phe Asn Cys Glu Ala Pro Leu Ser Met Leu Val Asp Gln
145                 150                 155                 160

Gly Phe Ile Thr Pro Pro Ser Leu His Phe Val Arg Asn His Gly Ala
                165                 170                 175

Ala Pro Gln Leu Ser Phe Asp Asp His Arg Leu Glu Val Thr Gly Leu
            180                 185                 190

Val Asp Thr Pro Leu Thr Leu Ser Met Ala Asp Ile Leu Ala Met Pro
        195                 200                 205

Ser Val Thr Ile Pro Val Thr Leu Thr Cys Ala Gly Asn Arg Arg Lys
    210                 215                 220

Glu Gln Asn Met Thr Lys Gln Thr Ile Gly Phe Ser Trp Gly Ala Ala
225                 230                 235                 240

Ala Thr Ser Cys Asn Phe Trp Thr Gly Val Arg Val Arg Asp Val Leu
                245                 250                 255

Gln Lys Ala Gly Ile Gln Met Asp Lys Ala Arg His Val Cys Phe Val
            260                 265                 270

Gly Cys Asp Asn Leu Pro Gly Gly Lys Tyr Gly Thr Ser Val Asp Leu
        275                 280                 285

Ala Thr Ala Met Asp Gln Phe Gly Glu Val Met Leu Ala Tyr Glu Gln
    290                 295                 300

Asn Gly Ile Arg Leu Thr Pro Asp His Gly Ala Pro Leu Arg Val Val
305                 310                 315                 320

Ile Pro Gly Trp Ile Gly Gly Arg Met Val Lys Trp Val Thr Gly Leu
                325                 330                 335

Ser Val Thr Ser Glu Glu Ser Gln Glu His Tyr His Phe Phe Asp Asn
            340                 345                 350

Arg Ile Leu Pro Pro His Val Asp Ala Glu Leu Ala Lys Ser Glu Gly
        355                 360                 365

Trp Trp Tyr Lys Arg Glu Tyr Leu Phe Asn Gln Leu Asn Ile Asn Ser
    370                 375                 380
```

```
Ala Ile Ser Ser Pro Ala Asn Gly Glu Leu Met Ser Leu Ser Gly Ala
385                 390                 395                 400

Gly Val Tyr Thr Leu Lys Gly Tyr Ala Tyr Ser Gly Gly Arg Lys
                405                 410                 415

Val Thr Arg Val Glu Val Ser Val Asp Gly Gly Lys Thr Trp Leu Leu
            420                 425                 430

Ala Thr Leu Asp His Pro Glu Glu Arg His Ser His Ala Pro Ser Tyr
        435                 440                 445

Gly Arg Tyr Tyr Cys Trp Cys Phe Trp Glu Tyr Thr Ile Asp Lys Phe
    450                 455                 460

Ala Leu Leu Asn Ala Ala Thr Ser Ser Gly Glu Leu Leu Val Arg Ala
465                 470                 475                 480

Trp Asp Glu Gly Asn Asn Thr Gln Pro Ala Lys Leu Thr Trp Asn Leu
                485                 490                 495

Met Gly Met Gly Asn Asn Cys Tyr Phe Arg Val Thr Val Ala Pro Lys
                500                 505                 510

Gln Ser Ser Gly Glu Phe Ala Leu Glu Phe Leu His Pro Thr Val Ala
            515                 520                 525

Gly Pro Ala Glu Gly Gly Trp Met Pro Pro Gln Glu Ser Val Val
530                 535                 540

Ala Ala Ala Ala Ala Ala Val Ala Glu Thr Leu Lys Arg Thr Lys
545                 550                 555                 560

Ala Ala Pro Gln Met Asn Lys Met Asp Gln Gln Asp Ser Lys Thr Ile
                565                 570                 575

Thr Met Glu Glu Val Ala Lys His Asp Thr Glu Glu Asp Ser Trp Ile
                580                 585                 590

Val Val His Asn Lys Val Tyr Asp Cys Thr Pro Phe Leu Lys Asp His
            595                 600                 605

Pro Gly Gly Gly Ala Ser Ile Val Met Asn Ala Gly Ala Asp Cys Thr
    610                 615                 620

Glu Glu Phe Asp Ala Ile His Ser Thr Lys Ala Lys Ser Met Leu Asp
625                 630                 635                 640

Asp Tyr Tyr Ile Gly Glu Leu Ala Val Glu Asp Ile Glu Asp Glu Pro
                645                 650                 655

Glu Gln Pro Ala Leu His Leu Ser Lys Ser Ser Val Gln Leu Met Lys
                660                 665                 670

Asp Asp Phe Lys Glu Gln Ser Val Arg Lys Ala Val Glu Gly Val Asp
        675                 680                 685

Glu Glu Val Val Thr Pro Val Ala Leu Asn Pro Lys Lys Trp Ile His
690                 695                 700

Phe Pro Leu Ile Gln Lys Glu Glu Leu Ser His Asp Thr Arg Arg Phe
705                 710                 715                 720

Arg Phe Gly Leu Pro Thr Pro Gly His Arg Leu Gly Leu Pro Val Gly
                725                 730                 735

Phe His Met Phe Leu Met Ala Thr Ile Asp Gly Ala Met Val Met Arg
            740                 745                 750

Ala Tyr Thr Pro Thr Ser Ser Asp Ala Glu Leu Gly Tyr Phe Asp Leu
        755                 760                 765

Val Ile Lys Val Tyr Phe Ala Asn Val His Pro Arg Phe Pro Asp Gly
    770                 775                 780

Gly Lys Leu Thr Gln Tyr Met Glu Glu Met Ser Leu Gly Asp Glu Ile
785                 790                 795                 800

Arg Val Lys Gly Pro Leu Gly His Ile Glu Tyr Arg Ser Arg Gly Glu
```

```
                    805                 810                 815
Met Thr Ile Asp Gly Lys Pro Arg Thr Val Ser Ala Leu Thr Gly Leu
            820                 825                 830

Met Ala Gly Ser Gly Ile Thr Pro Phe Tyr Gln Ile Leu Gln Ala Val
            835                 840                 845

Met Ala Asp Pro Glu Asp Lys Thr Glu Leu Tyr Leu Ile Tyr Ala Asn
850                 855                 860

Gln Thr Pro Glu Asp Val Leu Leu Arg Ser Glu Leu Asp Lys Met Ala
865                 870                 875                 880

Ala Glu Arg Asp Asn Ile His Val Trp Tyr Thr Cys Asp Arg Ala Pro
                885                 890                 895

Glu Asp Trp Lys Tyr Asp Ile Gly Phe Met Thr Val Asp Met Ile Lys
            900                 905                 910

Glu His Gly Ala Pro Ala Gly Pro Asp Val Leu Gly Leu Ser Cys Gly
            915                 920                 925

Pro Pro Pro Phe Ile Lys Phe Ala Ala Thr Pro Ser Leu Thr Lys Asn
            930                 935                 940

Gly Tyr Ala Glu Glu Asn Gln Phe Leu Phe
945                 950

<210> SEQ ID NO 9
<211> LENGTH: 954
<212> TYPE: PRT
<213> ORGANISM: Porphyra perforata

<400> SEQUENCE: 9

Met Glu Ala Ala Ser Gly Ala Leu Ser Glu Leu Arg Leu Glu Lys Gly
1               5                   10                  15

Val Lys Gly Trp Asp Pro Val Lys Val Pro Gly Arg Ser Ser Leu Lys
            20                  25                  30

Ser Thr Pro Ile Ala Thr Pro Glu Gly Ser Leu Arg Gly Gly Ser Leu
        35                  40                  45

Tyr Thr Ala Arg Ser Gln His Ala Ala Gly Ala Asn Asp Val Met Ala
    50                  55                  60

Ala Asn Gly Val Ser Ala Ser Ser Thr Ala Ser Gly Leu Ser Phe Ala
65                  70                  75                  80

Pro Ser Asp Gly Ser Gly Ser Gly Ser Arg Val Gly Trp Thr Glu
                85                  90                  95

Leu Asn Asp Ala Leu Asn Ala Lys Leu Ala Ser Lys Ser Thr Met Leu
            100                 105                 110

Asp Lys Gln His Val Ala Asp Glu Val Asp Asp Arg Asp Val Lys Thr
            115                 120                 125

Pro Asp Asn Trp Ile Pro Arg His Pro Ala Leu Ile Arg Leu Thr Gly
        130                 135                 140

Lys His Pro Phe Asn Cys Glu Ala Pro Leu Ser Met Leu Val Asp Gln
145                 150                 155                 160

Gly Phe Ile Thr Pro Pro Ser Leu His Phe Val Arg Asn His Gly Ala
                165                 170                 175

Ala Pro Gln Leu Ser Phe Asp Asp His Arg Leu Glu Val Thr Gly Leu
            180                 185                 190

Val Asp Thr Pro Leu Thr Leu Ser Met Ala Asp Ile Leu Ala Met Pro
            195                 200                 205

Ser Val Thr Ile Pro Val Thr Leu Thr Cys Ala Gly Asn Arg Arg Lys
    210                 215                 220
```

-continued

```
Glu Gln Asn Met Thr Lys Gln Thr Ile Gly Phe Ser Trp Gly Ala Ala
225                 230                 235                 240

Ala Thr Ser Cys Asn Phe Trp Thr Gly Val Arg Val Arg Asp Val Leu
            245                 250                 255

Gln Lys Ala Gly Ile Gln Met Asp Lys Ala Arg His Val Cys Phe Val
        260                 265                 270

Gly Cys Asp Asn Leu Pro Gly Gly Lys Tyr Gly Thr Ser Val Asp Leu
    275                 280                 285

Ala Thr Ala Met Asp Gln Phe Gly Glu Val Met Leu Ala Tyr Glu Gln
290                 295                 300

Asn Gly Ile Arg Leu Thr Pro Asp His Gly Ala Pro Leu Arg Val Val
305                 310                 315                 320

Ile Pro Gly Trp Ile Gly Gly Arg Met Val Lys Trp Val Thr Gly Leu
                325                 330                 335

Ser Val Thr Ser Glu Glu Ser Gln Glu His Tyr His Phe Phe Asp Asn
            340                 345                 350

Arg Ile Leu Pro Pro His Val Asp Ala Glu Leu Ala Lys Ser Glu Gly
        355                 360                 365

Trp Trp Tyr Lys Arg Glu Tyr Leu Phe Asn Gln Leu Asn Ile Asn Ser
    370                 375                 380

Ala Ile Ser Ser Pro Ala Asn Gly Glu Leu Met Ser Leu Ser Gly Ala
385                 390                 395                 400

Gly Val Tyr Thr Leu Lys Gly Tyr Ala Tyr Ser Gly Gly Arg Lys
                405                 410                 415

Val Thr Arg Val Glu Val Ser Val Asp Gly Gly Lys Thr Trp Leu Leu
            420                 425                 430

Ala Thr Leu Asp His Pro Glu Glu Arg His Ser His Ala Pro Ser Tyr
        435                 440                 445

Gly Arg Tyr Tyr Cys Trp Cys Phe Trp Glu Tyr Thr Ile Asp Lys Phe
    450                 455                 460

Ala Leu Leu Asn Ala Ala Thr Ser Ser Gly Glu Leu Leu Val Arg Ala
465                 470                 475                 480

Trp Asp Glu Gly Asn Asn Thr Gln Pro Ala Lys Leu Thr Trp Asn Leu
                485                 490                 495

Met Gly Met Gly Asn Asn Cys Tyr Phe Arg Val Thr Val Ala Pro Lys
            500                 505                 510

Gln Ser Ser Gly Glu Phe Ala Leu Glu Phe Leu His Pro Thr Val Ala
        515                 520                 525

Gly Pro Ala Glu Gly Gly Trp Met Pro Pro Gln Glu Ser Val Val
    530                 535                 540

Ala Ala Ala Ala Ala Ala Val Ala Glu Thr Leu Lys Arg Thr Lys
545                 550                 555                 560

Asp Ala Pro Gln Met Asn Lys Met Asp Gln Gln Asp Ser Lys Thr Ile
                565                 570                 575

Thr Met Glu Glu Val Ala Lys His Asp Thr Glu Glu Asp Ser Trp Ile
            580                 585                 590

Val Val His Asn Lys Val Tyr Asp Cys Thr Pro Phe Leu Lys Asp His
        595                 600                 605

Pro Gly Gly Gly Ala Ser Ile Val Met Asn Ala Gly Ala Asp Cys Thr
    610                 615                 620

Glu Glu Phe Asp Ala Ile His Ser Thr Lys Ala Lys Ser Met Leu Asp
625                 630                 635                 640

Asp Tyr Tyr Ile Gly Glu Leu Ala Val Glu Asp Ile Glu Asp Glu Pro
```

```
                    645                 650                 655
Glu Gln Pro Ala Leu His Leu Ser Lys Ser Ser Val Gln Leu Met Lys
                660                 665                 670

Asp Asp Phe Lys Glu Gln Ser Val Arg Lys Ala Val Glu Gly Val Asp
            675                 680                 685

Glu Glu Val Val Thr Pro Val Ala Leu Asn Pro Lys Lys Trp Ile His
        690                 695                 700

Phe Pro Leu Ile Gln Lys Glu Leu Ser His Asp Thr Arg Arg Phe
705                 710                 715                 720

Arg Phe Gly Leu Pro Thr Pro Gly His Arg Leu Gly Leu Pro Val Gly
                725                 730                 735

Phe His Met Phe Leu Met Ala Thr Ile Asp Gly Ala Met Val Met Arg
            740                 745                 750

Ala Tyr Thr Pro Thr Ser Ser Asp Ala Glu Leu Gly Tyr Phe Asp Leu
        755                 760                 765

Val Ile Lys Val Tyr Phe Ala Asn Val His Pro Arg Phe Pro Asp Gly
    770                 775                 780

Gly Lys Leu Thr Gln Tyr Met Glu Glu Met Ser Leu Gly Asp Glu Ile
785                 790                 795                 800

Arg Val Lys Gly Pro Leu Gly His Ile Glu Tyr Arg Ser Arg Gly Glu
                805                 810                 815

Met Thr Ile Asp Gly Lys Pro Arg Thr Val Ser Ala Leu Thr Gly Leu
            820                 825                 830

Met Ala Gly Ser Gly Ile Thr Pro Phe Tyr Gln Ile Leu Gln Ala Val
        835                 840                 845

Met Ala Asp Pro Glu Asp Lys Thr Glu Leu Tyr Leu Ile Tyr Ala Asn
    850                 855                 860

Gln Thr Pro Glu Asp Val Leu Leu Arg Ser Glu Leu Asp Lys Met Ala
865                 870                 875                 880

Ala Glu Arg Asp Asn Ile His Val Trp Tyr Thr Cys Asp Arg Ala Pro
                885                 890                 895

Glu Asp Trp Lys Tyr Asp Ile Gly Phe Met Thr Val Asp Met Ile Lys
            900                 905                 910

Glu His Gly Ala Pro Ala Gly Pro Asp Val Leu Gly Leu Ser Cys Gly
        915                 920                 925

Pro Pro Pro Phe Ile Lys Phe Ala Ala Thr Pro Ser Leu Thr Lys Asn
    930                 935                 940

Gly Tyr Ala Glu Glu Asn Gln Phe Leu Phe
945                 950

<210> SEQ ID NO 10
<211> LENGTH: 956
<212> TYPE: PRT
<213> ORGANISM: Porphyra yezoensis

<400> SEQUENCE: 10

Met Glu Ala Ala Ser Gly Ala Leu Ser Glu Leu Arg Leu Glu Lys Gly
1               5                   10                  15

Val Lys Gly Trp Asp Pro Val Lys Val Pro Ser Arg Ser Ser Leu Lys
                20                  25                  30

Ser Thr Pro Ile Ala Thr Pro Glu Gly Ser Leu Arg Gly Gly Ser Leu
            35                  40                  45

Tyr Thr Thr Arg Ala Ala Asp Gly Gly Ala Ala Gly Ala Asn Gly Gly
        50                  55                  60
```

-continued

```
Met Ala Ala Asn Gly Val Ser Thr Ser Ser Thr Ser Ser Gly Leu Ser
 65                  70                  75                  80

Phe Ala Pro Ser Gly Ser Gly Ser Gly Ser Gly Arg Val Gly Trp
                 85                  90                  95

Thr Glu Leu Asn Asn Ala Leu Asn Ala Lys Leu Leu Ser Lys Ser Thr
                100                 105                 110

Met Leu Asp Lys Gln His Val Ala Glu Val Asp Asp Arg Asp Val
                115                 120                 125

Lys Thr Pro Asp Asn Trp Ile Pro Arg His Pro Asp Leu Val Arg Leu
130                 135                 140

Thr Gly Lys His Pro Phe Asn Cys Glu Ala Pro Leu Ser Met Leu Val
145                 150                 155                 160

Asp Gln Gly Phe Ile Thr Pro Pro Ser Leu His Phe Val Arg Asn His
                165                 170                 175

Gly Ala Ala Pro Gln Leu Ser Phe Asp Asp His Arg Leu Glu Val Ser
                180                 185                 190

Gly Leu Val Asp Thr Pro Leu Thr Leu Ser Met Glu Asp Ile Leu Ala
                195                 200                 205

Met Pro Ser Val Thr Ile Pro Val Thr Leu Thr Cys Ala Gly Asn Arg
210                 215                 220

Arg Lys Glu Gln Asn Met Thr Lys Gln Thr Ile Gly Phe Ser Trp Gly
225                 230                 235                 240

Ala Ala Ala Thr Ser Cys Asn Phe Trp Thr Gly Val Arg Leu Arg Asp
                245                 250                 255

Val Leu Glu Lys Ala Gly Ile Gln Met Asp Lys Ala Arg His Val Cys
                260                 265                 270

Phe Val Gly Cys Asp Asp Leu Pro Gly Gly Lys Tyr Gly Thr Ser Ile
                275                 280                 285

Asp Leu Ala Thr Ala Met Asp Gln Phe Gly Glu Val Met Leu Ala Tyr
                290                 295                 300

Glu Gln Asn Gly Ile Arg Leu Thr Pro Asp His Gly Ala Pro Leu Arg
305                 310                 315                 320

Val Val Ile Pro Gly Trp Ile Gly Gly Arg Met Val Lys Trp Leu Thr
                325                 330                 335

Gly Val Ser Val Thr Ala Glu Glu Ser Gln Glu His Tyr His Phe Phe
                340                 345                 350

Asp Asn Arg Ile Met Pro Pro His Val Asp Ala Glu Leu Ala Lys Ser
                355                 360                 365

Glu Gly Trp Trp Tyr Lys Arg Glu Tyr Leu Phe Asn Gln Leu Asn Ile
                370                 375                 380

Asn Ser Ala Ile Ser Ser Pro Ala Asn Gly Glu Leu Met Ser Leu Ser
385                 390                 395                 400

Gly Ala Gly Val Tyr Thr Leu Lys Gly Tyr Ala Tyr Ser Gly Gly Gly
                405                 410                 415

Arg Lys Val Thr Arg Val Glu Val Ser Val Asp Gly Gly Lys Thr Trp
                420                 425                 430

Leu Leu Ala Thr Leu Asp His Pro Glu Glu Arg His Ser His Ala Pro
                435                 440                 445

Ser Tyr Gly Arg Tyr Tyr Cys Trp Cys Phe Trp Glu Tyr Thr Ile Asp
                450                 455                 460

Lys Phe Ala Leu Leu Asn Ala Ala Thr Ser Ser Gly Glu Leu Leu Val
465                 470                 475                 480

Arg Ala Trp Asp Glu Gly Asn Asn Thr Gln Pro Ala Lys Leu Thr Trp
```

-continued

```
                485                 490                 495
Asn Leu Met Gly Met Gly Asn Asn Cys Tyr Phe Arg Val Thr Val Ala
            500                 505                 510
Pro Lys Gln Ser Ser Gly Glu Phe Val Leu Glu Phe Leu His Pro Thr
        515                 520                 525
Val Pro Gly Pro Ala Glu Gly Gly Trp Met Pro Pro Gln Glu Ser
    530                 535                 540
Val Val Ala Ala Ala Ala Ala Val Val Ala Glu Thr Leu Lys Arg
545                 550                 555                 560
Ala Lys Ser Ala Pro Gln Ile Asn Lys Met Asp Gln Glu Asp Thr Lys
                565                 570                 575
Thr Tyr Thr Met Glu Glu Val Ala Lys His Asp Thr Glu Glu Asp Ser
            580                 585                 590
Trp Ile Val Val His Asn Lys Val Tyr Asp Cys Thr Pro Phe Leu Lys
        595                 600                 605
Asp His Pro Gly Gly Ala Ser Ile Val Met Asn Ala Gly Ala Asp
    610                 615                 620
Cys Thr Glu Glu Phe Asp Ala Ile His Ser Thr Lys Ala Lys Gly Met
625                 630                 635                 640
Leu Asp Asp Tyr Tyr Ile Gly Glu Leu Ala Ile Glu Asp Ile Glu Asp
                645                 650                 655
Glu Pro Glu Gln Pro Ala Leu His Met Ser Lys Ser Ser Val Gln Leu
            660                 665                 670
Met Lys Asp Asp Phe Lys Glu Gln Ser Val Arg Lys Ala Val Asp Asp
        675                 680                 685
Glu Glu Ala Ala Pro Val Ala Pro Val Ala Leu Asn Pro Lys Lys Trp
    690                 695                 700
Val His Phe Pro Leu Ile Gln Lys Glu Glu Leu Ser His Asp Thr Arg
705                 710                 715                 720
Arg Phe Arg Phe Gly Leu Pro Thr Glu Gly His Arg Leu Gly Leu Pro
                725                 730                 735
Val Gly Phe His Met Phe Leu Ala Ala Thr Ile Glu Gly Ser Met Val
            740                 745                 750
Met Arg Ala Tyr Thr Pro Thr Ser Ser Asp Ala Gln Leu Gly Tyr Phe
        755                 760                 765
Asp Leu Val Ile Lys Val Tyr Phe Ala Asn Val His Pro Lys Phe Pro
    770                 775                 780
Gly Gly Gly Lys Leu Thr Gln Tyr Met Glu Glu Met Ser Leu Gly Asp
785                 790                 795                 800
Glu Ile Arg Val Lys Asp Pro Leu Gly His Ile Glu Tyr Arg Gly Arg
                805                 810                 815
Gly Glu Met Thr Ile Asp Gly Lys Pro Arg Thr Val Ser Ala Leu Thr
            820                 825                 830
Gly Leu Met Ala Gly Ser Gly Ile Thr Pro Phe Tyr Gln Ile Leu Gln
        835                 840                 845
Ala Val Met Ala Asp Pro Glu Asp Lys Thr Glu Leu Tyr Leu Ile Tyr
    850                 855                 860
Ala Asn Gln Thr Pro Glu Asp Val Leu Leu Arg Ser Glu Leu Asp Lys
865                 870                 875                 880
Met Ala Ala Glu Arg Asp Asn Ile His Val Trp Tyr Thr Cys Asp Arg
                885                 890                 895
Ala Pro Glu Asp Trp Gln Phe Asp Ile Gly Phe Met Thr Glu Lys Met
            900                 905                 910
```

```
Ile Lys Glu His Gly Ala Pro Ala Gly Pro Asp Val Leu Gly Leu Ser
            915                 920                 925

Cys Gly Pro Pro Pro Phe Ile Lys Phe Ala Ala Thr Pro Ser Leu Thr
            930                 935                 940

Lys Asn Gly Tyr Ala Glu Glu Asp Gln Phe Leu Phe
945                 950                 955

<210> SEQ ID NO 11
<211> LENGTH: 956
<212> TYPE: PRT
<213> ORGANISM: Porphyra yezoensis

<400> SEQUENCE: 11

Met Glu Ala Ala Ser Gly Ala Leu Ser Glu Leu Arg Leu Glu Lys Gly
  1               5                  10                  15

Val Lys Gly Trp Asp Pro Val Lys Val Pro Ser Arg Ser Ser Leu Lys
             20                  25                  30

Ser Thr Pro Ile Ala Thr Pro Glu Gly Ser Leu Arg Gly Gly Ser Leu
         35                  40                  45

Tyr Thr Thr Arg Ala Ala Asp Gly Gly Ala Ala Gly Ala Asn Gly Gly
     50                  55                  60

Met Ala Ala Asn Gly Val Ser Thr Ser Ser Thr Ser Ser Gly Leu Ser
 65                  70                  75                  80

Phe Ala Pro Ser Gly Gly Ser Gly Ser Gly Arg Val Gly Trp
                 85                  90                  95

Thr Glu Leu Asn Asn Ala Leu Asn Ala Lys Leu Leu Ser Lys Ser Thr
                100                 105                 110

Met Leu Asp Lys Gln His Val Ala Glu Glu Val Asp Asp Arg Asp Val
            115                 120                 125

Lys Thr Pro Asp Asn Trp Ile Pro Arg His Pro Asp Leu Val Arg Leu
        130                 135                 140

Thr Gly Lys His Pro Phe Asn Cys Glu Ala Pro Leu Ser Met Leu Val
145                 150                 155                 160

Asp Gln Gly Phe Ile Thr Pro Pro Ser Leu His Phe Val Arg Asn His
                165                 170                 175

Gly Ala Ala Pro Gln Leu Ser Phe Asp Asp His Arg Leu Glu Val Ser
            180                 185                 190

Gly Leu Val Asp Thr Pro Leu Thr Leu Ser Met Glu Asp Ile Leu Ala
        195                 200                 205

Met Pro Ser Val Thr Ile Pro Val Thr Leu Thr Cys Ala Gly Asn Arg
    210                 215                 220

Arg Lys Glu Gln Asn Met Thr Lys Gln Thr Ile Gly Phe Ser Trp Gly
225                 230                 235                 240

Ala Ala Ala Thr Ser Cys Asn Phe Trp Thr Gly Val Arg Leu Arg Asp
                245                 250                 255

Val Leu Glu Lys Ala Gly Ile Gln Met Asp Lys Ala Arg His Val Cys
            260                 265                 270

Phe Val Gly Cys Asp Asp Leu Pro Gly Gly Lys Tyr Gly Thr Ser Ile
        275                 280                 285

Asp Leu Ala Thr Ala Met Asp Gln Phe Gly Glu Val Met Leu Ala Tyr
    290                 295                 300

Glu Gln Asn Gly Ile Arg Leu Thr Pro Asp His Gly Ala Pro Leu Arg
305                 310                 315                 320

Val Val Ile Pro Gly Trp Ile Gly Gly Arg Met Val Lys Trp Leu Thr
```

```
                    325                 330                 335
Gly Val Ser Val Thr Ala Glu Glu Ser Gln Glu His Tyr His Phe Phe
                340                 345                 350

Asp Asn Arg Ile Met Pro Pro His Val Asp Ala Glu Leu Ala Lys Ser
                355                 360                 365

Glu Gly Trp Trp Tyr Lys Arg Glu Tyr Leu Phe Asn Gln Leu Asn Ile
            370                 375                 380

Asn Ser Ala Ile Ser Ser Pro Ala Asn Gly Glu Leu Met Ser Leu Ser
385                 390                 395                 400

Gly Ala Gly Val Tyr Thr Leu Lys Gly Tyr Ala Tyr Ser Gly Gly Gly
                405                 410                 415

Arg Lys Val Thr Arg Val Glu Val Ser Val Asp Gly Gly Lys Thr Trp
                420                 425                 430

Leu Leu Ala Thr Leu Asp His Pro Glu Glu Arg His Ser His Ala Pro
                435                 440                 445

Ser Tyr Gly Arg Tyr Tyr Cys Trp Cys Phe Trp Glu Tyr Thr Ile Asp
            450                 455                 460

Lys Phe Ala Leu Leu Asn Ala Ala Thr Ser Ser Gly Glu Leu Leu Val
465                 470                 475                 480

Arg Ala Trp Asp Glu Gly Asn Asn Thr Gln Pro Ala Lys Leu Thr Trp
                485                 490                 495

Asn Leu Met Gly Met Gly Asn Asn Cys Tyr Phe Arg Val Thr Val Ala
                500                 505                 510

Pro Lys Gln Ser Ser Gly Glu Phe Val Leu Glu Phe Leu His Pro Thr
            515                 520                 525

Val Pro Gly Pro Ala Glu Gly Gly Trp Met Pro Pro Gln Glu Ser
                530                 535                 540

Val Val Ala Ala Ala Ala Ala Val Ala Glu Thr Leu Lys Arg
545                 550                 555                 560

Ala Lys Ala Ala Pro Gln Ile Asn Lys Met Asp Gln Glu Asp Thr Lys
                565                 570                 575

Thr Tyr Thr Met Glu Glu Val Ala Lys His Asp Thr Glu Asp Ser
            580                 585                 590

Trp Ile Val Val His Asn Lys Val Tyr Asp Cys Thr Pro Phe Leu Lys
            595                 600                 605

Asp His Pro Gly Gly Gly Ala Ser Ile Val Met Asn Ala Gly Ala Asp
            610                 615                 620

Cys Thr Glu Glu Phe Asp Ala Ile His Ser Thr Lys Ala Lys Gly Met
625                 630                 635                 640

Leu Asp Asp Tyr Tyr Ile Gly Glu Leu Ala Ile Glu Asp Ile Glu Asp
                645                 650                 655

Glu Pro Glu Gln Pro Ala Leu His Met Ser Lys Ser Ser Val Gln Leu
                660                 665                 670

Met Lys Asp Asp Phe Lys Glu Gln Ser Val Arg Lys Ala Val Asp Asp
                675                 680                 685

Glu Glu Ala Ala Pro Val Ala Pro Val Ala Leu Asn Pro Lys Lys Trp
                690                 695                 700

Val His Phe Pro Leu Ile Gln Lys Glu Glu Leu Ser His Asp Thr Arg
705                 710                 715                 720

Arg Phe Arg Phe Gly Leu Pro Thr Glu Gly His Arg Leu Gly Leu Pro
                725                 730                 735

Val Gly Phe His Met Phe Leu Ala Ala Thr Ile Glu Gly Ser Met Val
                740                 745                 750
```

```
Met Arg Ala Tyr Thr Pro Thr Ser Ser Asp Ala Gln Leu Gly Tyr Phe
            755                 760                 765

Asp Leu Val Ile Lys Val Tyr Phe Ala Asn Val His Pro Lys Phe Pro
            770                 775                 780

Gly Gly Gly Lys Leu Thr Gln Tyr Met Glu Glu Met Ser Leu Gly Asp
785                 790                 795                 800

Glu Ile Arg Val Lys Asp Pro Leu Gly His Ile Glu Tyr Arg Gly Arg
            805                 810                 815

Gly Glu Met Thr Ile Asp Gly Lys Pro Arg Thr Val Ser Ala Leu Thr
            820                 825                 830

Gly Leu Met Ala Gly Ser Gly Ile Thr Pro Phe Tyr Gln Ile Leu Gln
            835                 840                 845

Ala Val Met Ala Asp Pro Glu Asp Lys Thr Glu Leu Tyr Leu Ile Tyr
            850                 855                 860

Ala Asn Gln Thr Pro Glu Asp Val Leu Leu Arg Ser Glu Leu Asp Lys
865                 870                 875                 880

Met Ala Ala Glu Arg Asp Asn Ile His Val Trp Tyr Thr Cys Asp Arg
            885                 890                 895

Ala Pro Glu Asp Trp Gln Phe Asp Ile Gly Phe Met Thr Glu Lys Met
            900                 905                 910

Ile Lys Glu His Gly Ala Pro Ala Gly Pro Asp Val Leu Gly Leu Ser
            915                 920                 925

Cys Gly Pro Pro Pro Phe Ile Lys Phe Ala Ala Thr Pro Ser Leu Thr
930                 935                 940

Lys Asn Gly Tyr Ala Glu Glu Asp Gln Phe Leu Phe
945                 950                 955

<210> SEQ ID NO 12
<211> LENGTH: 956
<212> TYPE: PRT
<213> ORGANISM: Porphyra yezoensis

<400> SEQUENCE: 12

Met Glu Ala Ala Ser Gly Ala Leu Ser Glu Leu Arg Leu Glu Lys Gly
  1               5                  10                  15

Val Lys Gly Trp Asp Pro Val Lys Val Pro Ser Arg Ser Ser Leu Lys
            20                  25                  30

Ser Thr Pro Ile Ala Thr Pro Glu Gly Ser Leu Arg Gly Gly Ser Leu
            35                  40                  45

Tyr Thr Thr Arg Ala Ala Asp Gly Gly Ala Ala Gly Ala Asn Gly Gly
            50                  55                  60

Met Ala Ala Asn Gly Val Ser Thr Ser Ser Thr Ser Ser Gly Leu Ser
 65                  70                  75                  80

Phe Ala Pro Ser Gly Gly Ser Gly Ser Gly Arg Val Gly Trp
            85                  90                  95

Thr Glu Leu Asn Asn Ala Leu Asn Ala Lys Leu Leu Ser Lys Ser Thr
            100                 105                 110

Met Leu Asp Lys Gln His Val Ala Glu Glu Val Asp Asp Arg Asp Val
            115                 120                 125

Lys Thr Pro Asp Asn Trp Ile Pro Arg His Pro Asp Leu Val Arg Leu
            130                 135                 140

Thr Gly Lys His Pro Phe Asn Cys Glu Ala Pro Leu Ser Met Leu Val
145                 150                 155                 160

Asp Gln Gly Phe Ile Thr Pro Pro Ser Leu His Phe Val Arg Asn His
```

-continued

```
                165                 170                 175
Gly Ala Ala Pro Gln Leu Ser Phe Asp Asp His Arg Leu Glu Val Ser
                180                 185                 190
Gly Leu Val Asp Thr Pro Leu Thr Leu Ser Met Glu Asp Ile Leu Ala
                195                 200                 205
Met Pro Ser Val Thr Ile Pro Val Thr Leu Thr Cys Ala Gly Asn Arg
                210                 215                 220
Arg Lys Glu Gln Asn Met Thr Lys Gln Thr Ile Gly Phe Ser Trp Gly
225                 230                 235                 240
Ala Ala Ala Thr Ser Cys Asn Phe Trp Thr Gly Val Arg Leu Arg Asp
                245                 250                 255
Val Leu Glu Lys Ala Gly Ile Gln Met Asp Lys Ala Arg His Val Cys
                260                 265                 270
Phe Val Gly Cys Asp Asp Leu Pro Gly Gly Lys Tyr Gly Thr Ser Ile
                275                 280                 285
Asp Leu Ala Thr Ala Met Asp Gln Phe Gly Glu Val Met Leu Ala Tyr
                290                 295                 300
Glu Gln Asn Gly Ile Arg Leu Thr Pro Asp His Gly Ala Pro Leu Arg
305                 310                 315                 320
Val Val Ile Pro Gly Trp Ile Gly Gly Arg Met Val Lys Trp Leu Thr
                325                 330                 335
Gly Val Ser Val Thr Ala Glu Glu Ser Gln Glu His Tyr His Phe Phe
                340                 345                 350
Asp Asn Arg Ile Met Pro Pro His Val Asp Ala Glu Leu Ala Lys Ser
                355                 360                 365
Glu Gly Trp Trp Tyr Lys Arg Glu Tyr Leu Phe Asn Gln Leu Asn Ile
370                 375                 380
Asn Ser Ala Ile Ser Ser Pro Ala Asn Gly Glu Leu Met Ser Leu Ser
385                 390                 395                 400
Gly Ala Gly Val Tyr Thr Leu Lys Gly Tyr Ala Tyr Ser Gly Gly Gly
                405                 410                 415
Arg Lys Val Thr Arg Val Glu Val Ser Val Asp Gly Gly Lys Thr Trp
                420                 425                 430
Leu Leu Ala Thr Leu Asp His Pro Glu Glu Arg His Ser His Ala Pro
                435                 440                 445
Ser Tyr Gly Arg Tyr Tyr Cys Trp Cys Phe Trp Glu Tyr Thr Ile Asp
                450                 455                 460
Lys Phe Ala Leu Leu Asn Ala Thr Ser Ser Gly Glu Leu Leu Val
465                 470                 475                 480
Arg Ala Trp Asp Glu Gly Asn Asn Thr Gln Pro Ala Lys Leu Thr Trp
                485                 490                 495
Asn Leu Met Gly Met Gly Asn Asn Cys Tyr Phe Arg Val Thr Val Ala
                500                 505                 510
Pro Lys Gln Ser Ser Gly Glu Phe Val Leu Glu Phe His Pro Thr
                515                 520                 525
Val Pro Gly Pro Ala Glu Gly Gly Trp Met Pro Pro Gln Glu Ser
                530                 535                 540
Val Val Ala Ala Ala Ala Ala Val Ala Glu Thr Leu Lys Arg
545                 550                 555                 560
Ala Lys Asp Ala Pro Gln Ile Asn Lys Met Asp Gln Glu Asp Thr Lys
                565                 570                 575
Thr Tyr Thr Met Glu Glu Val Ala Lys His Asp Thr Glu Glu Asp Ser
                580                 585                 590
```

```
Trp Ile Val Val His Asn Lys Val Tyr Asp Cys Thr Pro Phe Leu Lys
            595                 600                 605

Asp His Pro Gly Gly Gly Ala Ser Ile Val Met Asn Ala Gly Ala Asp
            610                 615                 620

Cys Thr Glu Glu Phe Asp Ala Ile His Ser Thr Lys Ala Lys Gly Met
625                 630                 635                 640

Leu Asp Asp Tyr Tyr Ile Gly Glu Leu Ala Ile Glu Asp Ile Glu Asp
            645                 650                 655

Glu Pro Glu Gln Pro Ala Leu His Met Ser Lys Ser Ser Val Gln Leu
            660                 665                 670

Met Lys Asp Asp Phe Lys Glu Gln Ser Val Arg Lys Ala Val Asp Asp
            675                 680                 685

Glu Glu Ala Ala Pro Val Ala Pro Val Ala Leu Asn Pro Lys Lys Trp
            690                 695                 700

Val His Phe Pro Leu Ile Gln Lys Glu Glu Leu Ser His Asp Thr Arg
705                 710                 715                 720

Arg Phe Arg Phe Gly Leu Pro Thr Glu Gly His Arg Leu Gly Leu Pro
            725                 730                 735

Val Gly Phe His Met Phe Leu Ala Ala Thr Ile Glu Gly Ser Met Val
            740                 745                 750

Met Arg Ala Tyr Thr Pro Thr Ser Ser Asp Ala Gln Leu Gly Tyr Phe
            755                 760                 765

Asp Leu Val Ile Lys Val Tyr Phe Ala Asn Val His Pro Lys Phe Pro
            770                 775                 780

Gly Gly Gly Lys Leu Thr Gln Tyr Met Glu Glu Met Ser Leu Gly Asp
785                 790                 795                 800

Glu Ile Arg Val Lys Asp Pro Leu Gly His Ile Glu Tyr Arg Gly Arg
            805                 810                 815

Gly Glu Met Thr Ile Asp Gly Lys Pro Arg Thr Val Ser Ala Leu Thr
            820                 825                 830

Gly Leu Met Ala Gly Ser Gly Ile Thr Pro Phe Tyr Gln Ile Leu Gln
            835                 840                 845

Ala Val Met Ala Asp Pro Glu Asp Lys Thr Glu Leu Tyr Leu Ile Tyr
850                 855                 860

Ala Asn Gln Thr Pro Glu Asp Val Leu Leu Arg Ser Glu Leu Asp Lys
865                 870                 875                 880

Met Ala Ala Glu Arg Asp Asn Ile His Val Trp Tyr Thr Cys Asp Arg
            885                 890                 895

Ala Pro Glu Asp Trp Gln Phe Asp Ile Gly Phe Met Thr Glu Lys Met
            900                 905                 910

Ile Lys Glu His Gly Ala Pro Ala Gly Pro Asp Val Leu Gly Leu Ser
            915                 920                 925

Cys Gly Pro Pro Pro Phe Ile Lys Phe Ala Ala Thr Pro Ser Leu Thr
            930                 935                 940

Lys Asn Gly Tyr Ala Glu Glu Asp Gln Phe Leu Phe
945                 950                 955
```

<210> SEQ ID NO 13
<211> LENGTH: 26
<212> TYPE: DNA
<213> ORGANISM: Porphyra yezoensis

<400> SEQUENCE: 13
attgtggtgc acaacaaggt gtatga                                    26

```
<210> SEQ ID NO 14
<211> LENGTH: 20
<212> TYPE: DNA
<213> ORGANISM: Porphyra yezoensis

<400> SEQUENCE: 14
tcggcttcca catgttcctg                                                   20

<210> SEQ ID NO 15
<211> LENGTH: 20
<212> TYPE: DNA
<213> ORGANISM: Porphyra perforata

<400> SEQUENCE: 15
ccgtgtacct ccgcaactct                                                   20

<210> SEQ ID NO 16
<211> LENGTH: 20
<212> TYPE: DNA
<213> ORGANISM: Porphyra perforata

<400> SEQUENCE: 16
gctgcacttt gtgcgcaacc                                                   20

<210> SEQ ID NO 17
<211> LENGTH: 20
<212> TYPE: DNA
<213> ORGANISM: Porphyra perforata

<400> SEQUENCE: 17
gcatgggacg agggcaacaa                                                   20

<210> SEQ ID NO 18
<211> LENGTH: 25
<212> TYPE: DNA
<213> ORGANISM: Porphyra perforata

<400> SEQUENCE: 18
gcttgcccgt cggcttccac atgtt                                             25

<210> SEQ ID NO 19
<211> LENGTH: 24
<212> TYPE: DNA
<213> ORGANISM: Porphyra perforata

<400> SEQUENCE: 19
catcgaaggc tccatggtca tgcg                                              24

<210> SEQ ID NO 20
<211> LENGTH: 25
<212> TYPE: DNA
<213> ORGANISM: Porphyra perforata

<400> SEQUENCE: 20
ctacacgcca acgtcgtctg acgca                                             25

<210> SEQ ID NO 21
<211> LENGTH: 21
<212> TYPE: DNA
<213> ORGANISM: Porphyra perforata

<400> SEQUENCE: 21
```

```
catggaggct gcttctggtg c                                              21

<210> SEQ ID NO 22
<211> LENGTH: 21
<212> TYPE: DNA
<213> ORGANISM: Porphyra perforata

<400> SEQUENCE: 22
tcaacgagct gcttgtgggc a                                              21

<210> SEQ ID NO 23
<211> LENGTH: 19
<212> TYPE: DNA
<213> ORGANISM: Porphyra yezoensis

<400> SEQUENCE: 23
cccatcaccg cacagccga                                                 19

<210> SEQ ID NO 24
<211> LENGTH: 22
<212> TYPE: DNA
<213> ORGANISM: Porphyra yezoensis

<400> SEQUENCE: 24
agagaggcgc cccttgcatg tt                                             22

<210> SEQ ID NO 25
<211> LENGTH: 2164
<212> TYPE: DNA
<213> ORGANISM: Zea mays

<400> SEQUENCE: 25
ttcgttacca actgggttgc ataggatttc atgattaaga gtgtgtttgg tttagctgtg      60
agttttctcc tatgaaaaaa ctgttgtgag aaaaaatagt tggaagtcgt ttagttcaaa     120
ctgttgtgag ttatccactg taaacaaatt gtatattgtt tatatacact ctgtttaaat     180
atatctctta atcagtatat ataattaaaa aactaatttc acatttgtgt tcctaatatt     240
ttttacaaat aaatcattgt ttaattccat ttgtaataag tttttattaa aattgctttt     300
atttcattta ttataaacat ttaattgttt taatcctatt ttagttttaa tttattgtat     360
ctatttatta atataacgaa cttcgataag aaacaaaagc aaggtcaagg tgtttttttca    420 aagtagttgt ggaaaagctg aacccctttt attcaacttt tagaagcagg aaaacagaac     480
caaacagacc ctaaaaatgt gtgaatttt agcaggttaa ttattcgcat ctctttggtc      540
atgtttaaga ggctggaata gatcaactgc aagaacacat agcagagtgg atagggggggg    600 ggggggggag ggtcgtcgtc tccctatctg acctctcttc tgcattggat tgccttttc     660 ggtactctat ttaaaactta aaagtacaaa tgaggtgccg gattgatgga gtgatatata    720
agtttgatgt gttttttcaca taagtgacaa gtattattga aagagaacat ttgcattgct    780
actgtttgca tatgggaaaa ttgagaattg tatcatgcca tggccgatca gttctttact    840
tagctcgatg taatgcacaa tgttgatagt atgtcgagga tctagcgatg taatggtgtt    900
aggacacgtg gttagctact aatataaatg taaggtcatt cgatggtttt tctattttca    960
attacctagc attatctcat ttctaattgt gataacaaat gcattagacc ataattctgt    1020
aaatatgtac atttaagcac acagtctata ttttaaaatt cttcttttg tgtggatatc     1080 ccaacccaaa tccacctctc tcttcaatcc gtgcatgttc accgctgcca agtgccaaca    1140
acacatcgca tcgtgcatat ctttgttggc ttgtgcacgg tcggcgccaa tggaggagac    1200
```

```
acctgtacgg tgcccttggt agaacaacat ccttatccct atatgtatgg tgcccttcgt   1260
agaatgacac cccttatccc tacaatagcc atgtatgcat accaagaatt aaatatactt   1320
tttcttgaac cacaataatt tattatagcg gcacttcttg ttcaggttga acacttattt   1380
ggaacaataa aatgccgagt tcctaaccac aggttcactt tttttttttcc ttatcctcct   1440 aggaaactaa attttaaaat cataaattta atttaaatgt taatgaaaac aaaaaattat   1500
ctacaaagac gactcttagc cacagccgcc tcactgcacc ctcaaccaca tcctgcaaac   1560
agacaccctc gccacatccc tccagattct tcactccgat gcagcctact tgctaacaga   1620
cgccctctcc acatcctgca aagcattcct ccaaattctt gcgatccccc gaatccagca   1680
ttaactgcta agggacgccc tctccacatc ctgctaccca attagccaac ggaataacac   1740
aagaaggcag gtgagcagtg acaaagcacg tcaacagcac cgagccaagc caaaaaggag   1800
caaggaggag caagcccaag ccgcagccgc agctctccag gtccccttgc gattgccgcc   1860
agcagtagca gacacccctc tccacatccc ctccggccgc taacagcagc aagccaagcc   1920
aaaaaggagc ctcagccgca gccggttccg ttgcggttac cgccgatcac atgcccaagg   1980
ccgcgccttt ccgaacgccg agggccgccc gttcccgtgc acagccacac acacacccgc   2040
ccgccaacga ctccccatcc ctatttgaac ccacccgcgc actgcattga tcaccaatcg   2100
catcgcagca gcacgagcag cacgccgtgc cgctccaacc atctcgcttc cgtgcttagc   2160
ttcc                                                                2164

<210> SEQ ID NO 26
<211> LENGTH: 3906
<212> TYPE: DNA
<213> ORGANISM: Oryza sativa

<400> SEQUENCE: 26
agaatctgaa gacagtgctg aaaatggtgc tgaaatgttc tctaaaactg acatgactgg     60
aaggaataac atgaatcagg tgtctgcatc aagcttttca agcattgcac aaagatttct    120
tgctaataca cttcagcgaa gaactcccaa atacactgat cttcctatgt catctgttat    180
agttaacact gatgcaaacg ggactgatga atctacccaa atatcttctc tagcccccaa    240
tgaaacaaca ttcgaggcat ctcaatttga gaagaaaaca gaaaatgaca caaatggact    300
gcccaaatcg tcactcttct ctagtagcca ttactctgag aaatcatctc cgccgcttga    360
gtacatgaaa atatctttcc accctatgag tgcatttgaa atgtcaaaat tggacctaga    420
tttctctgat gaaaatcttc atgagaatgc cgatgatatg atgttaccaa cgtttcagtt    480
acttccaggg tcttccgttc cacagcttgg tagtggttct gaatcggaag atgatacttt    540
tggcagatct tatagttatt cttcgtatga tgatctaagt ccacggttat attcaaactc    600
tgagttgtgg gatcaagaag acgcaaatgg attggaggat catgatatgc ataacaatcc    660
aaatcagata ggatccttcg gagcaccaat ctctagcttt gtggaatttg agcagatgga    720
cttatctggt gcgaagtcca ctgtatcact tacagatctt ggggatgata atggacttgg    780
cacgttagat tctcatcctg ctggagaact tcctaacttc gatactttga tggctcatca    840
aaatgaggcc ttcattccgc acaatccagt aagtttatca ccagatgaag gtcagttgcc    900
tccacctcct cctcttcccc caatgcaatg gaggacaatg agacaagtag cttctgtaga    960
agaaggaaga ggttctgcag ctaaagaaga tatgcttgag agtacctcag atctaccacc   1020
agtacacact cctgttcagg aagaacatct tctgcccatc gcaccaccag atcaacaaaa   1080
```

```
tcttctgccc atcgcaccac cagatcaaca agggcatgcg aaggaggtag tatgtctcat   1140
ctttaattga ctctatttg aataattctg tatcaataat cactgtcttt tattaatgat    1200
tcattaactt gacttatgca gaatgacaga aaagttgatg gggtaaaaga gataagcaat   1260
cctctcgaca ttgagatcag agcaagcttg cttcagcaaa tcagggataa ggtttgcttc   1320
attctttctt aaaaaaaaaa tctgttgttc tctattgttt catagttttg ttactctttt   1380
gtgttgaaac ctgagcaatt ttagaatttt tagttacgaa cagatagcac cagagtatca   1440
tgtgacaata tatcatggag gctctgtgcc ttcttctttt gccaatacaa atatttttt    1500
ttctgatggt tgttatttga ttcttgaact tgaaagctag ttagcaaatt tttggcattc   1560
aatactgata tttttgttca ttttaataac ttgcagtcag gtcagcagaa gctgaatgga   1620
catgaaaagt caaaagcagt aggcaatgat actaaaaact tggatgaaag ggaggagttg   1680
cttcaacaaa tcaggagcaa ggtatttcca ttatctgccc tattgtactt gtgtagtata   1740
atgctacctg acaggtcttt atgttaagtt ttcttgatcc atgcctagtc gacagacttg   1800
cagttgaaac acgatacact agaacaccca cattgagggc ccatctctct caaccaaacc   1860
ataaacacac aataagaagg ctaaataact acttagttg ttactatgct cgtatgatgc    1920
atacagtcat ctcagaaaat aactgtagct agtttgctaa tatgttcaca tgatgcagac   1980
attcaattta agacgaacaa atgcatctaa gacaaacacc tcatcaccaa ccactgccaa   2040
ctccagcgtt gtagcaatct tggaaaaggc aaatgcaatc cgccaggttt gtattgattc   2100
ttttttccc cttgatgtta gtttatgcgc tactttcctt acgttttccc tgattgtttc    2160
catgctatca ggctgtggcc agtgatgagg gaggtgatga tgatagttgg agtgatatat   2220
gaatactcaa ctggaacgcg tatgaaactc ttttctgta tattcagcta gtacaagatg    2280
aagtgaaaaa atgtgaataa catccttttc ttcattgtaa ttagatttc caggtctgtt    2340
ttgtacctct ttttagttca cattagtgta ttctctcata ggcccatgcg gttgtggaaa   2400
tggttagatc attttcacat tatgtaaatt aactttatta tttattttg atagtgaaat    2460
taactggtaa aataagcatg ttaaactgtt ttttctagca atgtattgaa ataatatctc   2520
tttgcattca taataatatg ggggtgtatc tgtgcaacag atttatttt tcttcccccc    2580
ccctacccct ttgaagtatg ctgttgacct attgtccttc ccctcaacaa aggcaataat   2640
tctgaattgc aaatcattca cattactcta tcagctttgt ttggttaaca gcattatctg   2700
tgctatttac ttcatttgtt atgttggacc tacggaaaaa tctggtagat acatacttag   2760
ttgtgcaaac ttactgcgta cctggtgtta tttgttaagt taaaaatgct gctaatcagt   2820
ttaagtctag gttcttaagc tttgcttcca acttggtata atactattta tgtttgtccc   2880
ttcctgttct tattacaaac aagaaaggca gagtatggta tgcttttta tcctttgcat    2940
gagttgcaca acctgatcct agacaagcga cttctcatct tgatcctgtg gtctcttact   3000
actactgttt tgaacatggg cagactatgc tacagttata tcacttgtcc atagtaaact   3060
gctaagtgtt ttccttcttt tattagatgt atagcatgca ataataatta gttcagtcac   3120
caatttgtta cctcttagga tgcttctaat gccttttatt tttaacatga gttgtgcttt   3180
ctatttata tcattggatg ttcttaaatc tattactgtt tgtaaacaag ctcttctacg    3240
gcaatgcatt tttttatgcc acatatggta tctatctgtc atcagattga cgtggtacac   3300
aattcttgtg gtttgtggga actgggaaat ggtcatttgc aattgttact aaagcaagtg   3360
gcccatttg caatattttg tttctcacgt tgcaaactgg gctagttgaa tataaatttcc   3420
ttctgcattt ttccaatgtg aattcctgaa gcaaattgtc ttcctctcct attcgttgt    3480
```

| | |
|---|---|
| tcccagtttt taacagattg ttcctcttac agtgccatgg tctcatgggc aagatttgc | 3540 |
| agccaggcct ctctatcggt ccaatgttct accagctaca gaaaacgaaa gtctcagaat | 3600 |
| cccagccatg aacccgttgt gcagctcttc agccctccta agcgccagtt cctgaaagaa | 3660 |
| aacaaaacaa aagagccacc tggaacgtaa atacttcca gggatgcaaa ggctgacttc | 3720 |
| tcacaaatcc tcacagaaaa atgaaaagac agacaaaaca acacgcataa gtctcgcaaa | 3780 |
| ctgggataat tttcggcttc tcgccgtgcc acgggcgagc cgacgagcag cgtgcgtcac | 3840 |
| caccgtacgg cgagaattgt atggcacgca cgggagggtt agccacagcg gagatgagac | 3900 |
| atcagc | 3906 |

<210> SEQ ID NO 27
<211> LENGTH: 3510
<212> TYPE: DNA
<213> ORGANISM: Arabidopsis thaliana

<400> SEQUENCE: 27

| | |
|---|---|
| cgccagatca tacatgctgt aaagaaaaga tgtccagata cgccgatagt tttctacatc | 60 |
| aatggaaatg gtggccttct tgagcgaatg aaaggaactg gagctgatgt tattggactt | 120 |
| gactggactg tagatatggc tgatggaagg aggcgattgg gaagcgaggt aagtgtgcag | 180 |
| ggaaatgttg atccagctta cctattctct ccgcttcctg ctttgaccga agaaattgaa | 240 |
| aggtaggtca ctttgttcag ctgaataaaa aagtagtgct tataattcaa attaagaaac | 300 |
| tgaaagaaat gtatgttttg tgtcagagtt gtgaagtgtg ctggaccaaa agggcatatt | 360 |
| ctcaatctag gacacggtgt cttggtaggg acaccagagg aagccgtggc tcatttcttt | 420 |
| gaaaccgcta gaaacttgga ttaccaaaca cttttccaaa atcatgttcc tgcagaaaaa | 480 |
| gctgaacctg aattggttgt ctgagaaatg gtgactagac aagtgcctac gccgaagaat | 540 |
| ttgctgttta agttttgtga acatatgtct gaatctctta aacttggtgc aggaatgaga | 600 |
| gaaaaagttc catgtctgac ccttaatcga tgctagagtt ggtaacttgc tatgagatat | 660 |
| atgcgaagct gtccagtttt tgtttggctt gcttgaggat ttccaatctt ctggaccaag | 720 |
| ctctgcttaa cgtttaacaa tgtattgagt tgctcctagg cttcaaatgt tgctgcttct | 780 |
| tttggagata tgactctggt taaagtttaa ccaaacattc atttatctgg ttaatctcaa | 840 |
| acctttgcta tgtttgttat cccactttt tcatatggtt cttctagat ctctgtatct | 900 |
| ggtgtgtctt ctctcgtgat ctcaacattc gatgtgaaac caggtagatt gtaatattgt | 960 |
| atcatagact gcaaaagata acgcaaaaga gaagtctctg atctcaacct gaatcagact | 1020 |
| tgttaggagt ccctcttgtt tggtttaatt caatttttccg gttcggattt ctggattata | 1080 |
| aaccgaatta actacaaacg gaaaaacgta ccgcgttatt gcggtaacca gcaactttaa | 1140 |
| ttggcctata gtagaatcaa atgaaaagaa aagagcaatt ttttttttttt ttttttggtt | 1200 |
| ttttggttaa agaagaaaag agcaaattgg aaaaacaaat agataagata atttatatga | 1260 |
| tttaaaagtc aaatgtaatc acaacatata aattttaact tataaaatat agtcacacca | 1320 |
| ttgcctcatc gtatttgctt tcatgaatca tcccaccact tgtaagcttt attttattaa | 1380 |
| gaatgaaaac ggagaaatat aaattgaaca ctatatacta ttgtcgtcac cctccccgaa | 1440 |
| tgtttctgat aaataatgtt aactatcatc taatacgtca accggattat caccgacact | 1500 |
| gaccccacac ctaaccactg atgcacaagt ttatattagt gtaggtatca tccacaatat | 1560 |
| attatccaat aattgaacct tgttaatgtc tttggttcat aaagcgatct ataatcaatt | 1620 |

| | |
|---|---|
| cagcattatt gctaaaattc aaattaagaa gacggcatga tttgttaaaa ccataaagaa | 1680 |
| atacaaaagg gtcaatgata aaactgttta aacgaatcag tctacccaag agccgtctct | 1740 |
| cgaatactag ttttaaattc ataagcgtat agagtttagt gattccagaa cactttacag | 1800 |
| gccaaaatct aatatttcga tattttgaaa cgacattttt agtcctataa ttaaatttgc | 1860 |
| aacgtattag attactttta aaatgtgata ctgcgaagaa aatgaatcaa agattgaat | 1920 |
| cgaatattcg aacagacgga caagaaccca cgaagcgata cagatcagaa actctgcttc | 1980 |
| ttttttaac aagagatcac aaacttggtt gacttgagtt catattataa tgacgtactc | 2040 |
| agtgattcga atattccata aatagtcgta agaataaaga ccttaatgta tacattgttc | 2100 |
| atttcgtatg ccacattgac gaagatcact gatataaatt tcaattatat aaatgtaaaa | 2160 |
| taacaaaaca aaaagttaca tgttatcaaa tagtgtcatt agctaaataa catgttactt | 2220 |
| ggccaccaca tcacttttgt tgagaaattt ctaaatttg gctatttagt gcatataccc | 2280 |
| tttaaaactt gttgtaaaag caaggaagag gaaaaaagat tgaacctata gcaaaggaaa | 2340 |
| aagaaaagag agtacatatt cttaagtctt gattacaata ttttgttctt caacatattc | 2400 |
| tcttagagtt gagataacat aaattataat atagatgctc tattgggtag cagtagatag | 2460 |
| aagaacatat gctgaaaatc attttatag atctagcaaa tcacctttat aaaggatcca | 2520 |
| gatttttttt ttttttaactt tttgaaagtc aacttgatca tatgtgaaag ttagagtcag | 2580 |
| agatttatgc atcttcgtgc atagacaaaa tgcatgcacg agctcacacg atcctgtttt | 2640 |
| tttttcttaa tgaggtaatt ttcttgctgt cattttttt tctaaagtta agattcatat | 2700 |
| aaaaaccata tcaggtaatt ccttaatttt gtgtaataat taagaaatca ggatcattag | 2760 |
| atctttgacc accaaaactc aaatttgttc ccaaatacac tcagttaaag tactatcttt | 2820 |
| aatcatttca tattcgttac tttgtaaatt agtacaaagt aagtaacaaa ttttagttta | 2880 |
| cccaatgaaa tggaatgaag ttaatgaaaa tattcgttct tttagaatat tcttctgctc | 2940 |
| ttgacagtgt ttaattattt aattttctta cttgaaaaaa taaaattgac caacaattat | 3000 |
| ttttcttacc tcatgtagat aacttacaaa ataaaacata tatatatgta tatatatatt | 3060 |
| tattttcaac tcagaaataa ataattctaa cgaaaaaata tgaaataata aaaaaatctg | 3120 |
| acttaaaaag cgcgcatcgc tcatgccaac acactccctc gtctataaat acttcactct | 3180 |
| gctttcctca atcacatcca tctctgaatc tgattccaca tcttaaaccc ttattcccta | 3240 |
| aacatcgaat ttggttcctt ctcccacaat ccgcagagat ttcttctttt caggtttgtc | 3300 |
| aattcatttt ttttttcagt ttgagttttg ttttgttttt tcgtgatttt cggtcagtct | 3360 |
| accaaatccc ctgttttcc ggcgattcag ttgtcaacag attttgcttt tcttttccc | 3420 |
| ttttgtgta aaaaaactca tttcctttt gatctgatga ttacagaaga agtaagaggg | 3480 |
| tggcgaagaa gatttgattg atcggcgata | 3510 |

<210> SEQ ID NO 28
<211> LENGTH: 2997
<212> TYPE: DNA
<213> ORGANISM: Arabidopsis thaliana

<400> SEQUENCE: 28

| | |
|---|---|
| taagtatacc catgtggttt tcttttattt ttgaatagaa tttgggactt cacattcctt | 60 |
| caaagtagga cttcaatggt tttttggaaa catgacttat ttgcaaaata tatacaaaaa | 120 |
| caatgaatag caagactttt ttctttttgt cagcaatgaa tagcaagact taagtaacat | 180 |
| atttttaatt tttggcttat acacaagaaa aaagtcgcat attttttggtt tggaacttga | 240 |

```
gccggttcga tgtctgacaa gtcgatttga aaaacttctt tataattttt tacttttcgg    300 tttatattc ttttgtattt tacaactgga tcttgtttat atatatcaat atatgtgaaa    360
tgagcgtact agtactatta ttggtgtgga atactttcgc atgccctagt cttaactctt    420
aaggataagt aagggcaggt ttctctttgt tttccaaatt tatcgttcaa tatttcttaa    480
attaggatat aatgtacaat taatcgttca tttcttttaa ttagaaccgt agtttgtaca    540
catcactaca tagccacact atagtaatta agtgaagcct catcagaaaa ggaaaacgat    600
ctatagatga aaaagttaaa tacccaagag aagtgatttt cagttaaaag tatagttttt    660
gctaaaaata tttataacgg cattaatcac gatactcgcg taagtagtat actctaccat    720
atactatctt ttagtgagtc ggaaatatgt cataagccat tacgcgacca tgcaatattg    780
cttccgtaag catccgcact agtaaagtgt ccaaatggat gccgtcaaaa caacaaaagt    840
gttttaaaaa agaaccgaaa caagttttca cacttggtcc ttagcttctc aaactcttct    900
tcgtcctgat aatggacttt aattatcatg ttatacgtca accaagttat cagctaacca    960
tcatcacttt attaagtata tgcagccttg tgctcataat attcattata ttatactaaa   1020
agtctaatca tatgaagaaa ggaaaaaaaa aaaagaggc ttgtttatga aattaaggag   1080
tgcacgtaag gccatattta taattctatt tcagaaaatg taaattcaaa cacggcaaat   1140
atgttagttt catggtgcat gcatgatgca tttccaactg tttctttttt tggggatgaa   1200
aatgtatttc caccggttaa ttaacgaagc ttctatttca tgtttccgtt ttcttttact   1260
tttttttttt gttttacttt catatatatc atttgacaaa gttaaggctt taaaatggca   1320
gtagtttctt aatttgtttt tagattttgg atttatggtg tttagttctt agttttttt    1380 tgcagtaaat tttagttttt ataaatgt atgtacccaa tacatatcac tatatatttt   1440
atagtccaaa agaattttat gtgatggtga aaagaaaaaa atgtgtgatc attcgctgaa   1500
attaataaat tttgcagtat attaaagaaa actagaaaag tgagtaccta atattccaac   1560
aattagactg tatcactcat gcctgtcgtc tgtcgactgt tgacttgtgt tataataaag   1620
acatttcaaa ttatccgaat attccattag cacatatgaa gatatccaat ttttgaataa   1680
ttggagtcga ccaatgtaaa atattcataa cgtgacatca catcacatac atgtacgact   1740
ttgtcactta ccaaaaatga tctagttatg ataataacat catcacatga gtaagaatga   1800
taaggcatga tctaatcagc atcatatacc gctactttat ttactatcac attttcgttc   1860
acaagagtaa tattatattt gattttatat atgtctaaaa atttatcgta gactgccgat   1920
tttagatttt gggaggttag aagaactaat aaaaccgaaa gaaatagatg atggtcggtt   1980
aaatacttaa gtcctttata agaaagaaaa attaaaagtc aactttatcg ctgaaagtga   2040
aagttaggtt gaaagttcag agatttattc atcaacttcc gtgcattgac acatgctctt   2100
ctctacattc gctcacgtga attttagaac aacaaattat tttacaaaca ctataatctt   2160
ccggtaattt aaccacaata aagagataaa taatctttat attaaatcga tcgaattcta   2220
attctgtagg tactgtgagt caaacatgaa agtgtaaatt ttcaaaatat gattggtgtt   2280
aacttaggtg aatcaatttt tgatgttttt ttgttgatta tataaatcaa aattacggaa   2340
gaatgcatgt tgtttacata agtgatataa ttaattttt actgatatat taaaaataaa   2400 aatatttat gttattgttt tggttatttt tttgttccac aaaaattaat taatcataat   2460
atttctttct tgactatcac tagattcaat gaaaatctct cttttataca taaataaaaa   2520
tcttctcaat gcattaataa atatatataa attgaggaaa aaaagagata gaaatcatgg   2580
```

```
aaaaaaaggt taaaaattcc aactataagc gagcatcaca tatagaaata gaataatgta    2640
taggaatcca tcatgatctc actctctata tataggtaag ccaagtatct tattttggt     2700 tatgtatctc tgaaatctga atctgactga cttcaaagga cacagctttt acttctataa    2760
ctggttagct tctccacaca cacacacact tgttagattt acttttcctc cgcactatca    2820
gcagattttt ctcatctggg tctgtttgtt tctgttgact caaagtttcc gactttctta    2880
ttttctgtct ccgatttcat cgccgaaatc tcagtcaatt ttgtctttag atctttaatt    2940
tttggatccc tttaattatt ttgtttggtc ttacttcaga gcgaagcagg tgaaaaa      2997
```

<210> SEQ ID NO 29
<211> LENGTH: 3367
<212> TYPE: DNA
<213> ORGANISM: Arabidopsis thaliana

<400> SEQUENCE: 29

```
aaactaaaag aatttaaaac tgatgtcaat atcttatctg ccatattcgg accttactta      60
catccgatcc cactgattta ctacccaaa tcagattttg atattgggct gtgattgcgt     120
cacatttata tgggctaata tgatatgagc ccaggactat ctcgctcagg atttattgtg    180
tttgactttt caagttctcg tattcgaccc ccttccccca ccttaaaacg ctccgtttca    240
ctttcagttt cattttctat gactatttat ttattgaaat atattatgat ctctgcatag    300
acatatatag acctcgacgt atctctctct ctctctcggt aacttggacc actcgaaatt    360
gagttttgaa gcacggataa cgtttggttt gaccttttgg gtttgtcata ggtcgtttta    420
tttggtcggt acactcgtaa tctctaaaca aaaatatatc actttagtca cacctttta    480 tttggggtca ttgtgcatgt gtgtaataat aagtgaatac tgaatcatca ttctagtctc    540
taatacatca tatacaacta cataatagtt aactaaatgc taactcgtgt gcgtaaatta    600
ctgtattact atagtgttac tgttatgcat ttttgtctga gacgatgcaa atcttgatca    660
tatactatat acagggtaat tttagcatgc acaagtttat atttgcatat aaatatccga    720
agaatatccg tagaacagtt agaatatatt cccactagcc accactatct caaatttcat    780
tttcagatct aaagttatgc ttttattgtt tcttttctat ataactcaat catataccat    840
taatatcaaa catcacccat cacataagtt acgaatgtcc atttccgcac cggacttaac    900
ttgtttggag aaaatgtaat atcactcatg gcaataatca accatgtatg cacattgatt    960
aaaatgtgtt ttcccgatgg agagcaaata tatcttattc gagtgatcaa gttcataaag    1020
agctcgaatt agttatgctt ttattcaaag tagagcaatt tcataaaact ataatatatc    1080
ttaactgtaa taacagatca gctggctaaa tactatgatg ctactactga agatgagatt    1140
gcaaaacata aaacttgtgg cttgatgagt tcatatagaa gatataataa ttatgcaaac    1200
caaaatatgt atacgtacga atcttctttt accatacgga tcgtcgtcgg atactgcttg    1260
tctttttctc tgttttttc tcctaaatat cacatatata ttcaatgtga gaaagtatga    1320
gaaacaggac aaaatataga tattggttcg taagtttttt agtggctaga gttaaataag    1380
gaattaaatg agagcaaatc tctttgatat acacctcata tcaatgaaaa aacttaatat    1440
tggtgtattt gtttctttcg tccgactctt gaagaattaa aaggttatat acaaaaaaaa    1500
atttgccctt tcacattttc taaagatcat atcatctttg atataatcgt ttgatgcatg    1560
tttactcatt cataaacatt ttataaaatc ttctatatta ttttgattcg aaatttcaca    1620
ctcaaaacat aaaatttcca aggataacca atgaaatgaa tacacaagat ataatataag    1680
ttatcaccat aaattacata atcagtatag ataaagaaaa tgttctgaat accaatttag    1740
```

-continued

```
tttataaatt tatttttttc gtttatgatt tatcaatggt tcagttgagt ggttttaat      1800 taaaaaaata atattttgtt caacaaaaat tcagaacgat ggttggaaaa aataaattaa      1860
aacaatgcgt atattggatt aaaaataaat catattatat gattctattt gtccgggatt      1920
tataaattga tatgatacga taaggtcagt gataaaataa attgataaga taaggacttt      1980
atatgattct atttccaccc gttggaatct ttggttggct atttattctt agattcgaga      2040
atcaattagc gaaaacaaat actagtttaa aaaagaaaaa aactatatga taagagaccg      2100
taatagacgt ggtacgtttt aagtcaaagg tcaaaaagcc gaattatata tttctggctc      2160
cttccacaac ttttggaaaa tttccttcgt agttttcact tgaacccatt ttttaacaac      2220
aattcttcta cttggattga taattcaaaa ggaaactaac tctcccatag ttaaaactga      2280
atcactgtta aaaaaaaaaa aaagtaaagt aaatatacta aatcaatgtt tttttctctg      2340
gaagtaaata tacaagttta aaattaaagg agaagagaag ctatatattg ctttgcctca      2400
ccatttagga gataattcat atgaagcaaa gaaagcatat cctttggcat attcgataat      2460
atatggcatc taatcatctg tataagcttt tcatattttt gttagatgct ttttcgtaca      2520
aatgcattaa gataaaatta aacaaaaaaa caagatatga tattcagttt cgtgaaatat      2580
taaaagaagt caaaaaaagg gaaaaatgaa aagtcgaatt ggtggacagt ggactcattg      2640
gtccacttaa aagtcatcag aaccgtacac atgcaagctt ggtccatttt cgtatgacga      2700
cgtacaagtt acaacattca aaaaacttcc taatttacaa gttttgctt atgtttatgg      2760 gaaatatttt tctgcaacga aaaatcatta agactatatt tttctgttgg caaagacttg      2820
actcagtccc ttttactgc ccattagtaa tctttggagt gaaaatacga atttaactaa      2880
ttttctaaaa tttgattaaa gtctaagaga gaaaaaaaga tttcggctat aaataagtta      2940
caactacaca tcgaatggac tagaaaattt tcgcttctta tattttttta aaagaaaaa      3000 ccaaaaaatc ctttgaaact ttttagcct gtcgcttctc tttccatcgt cttcctcgtg       3060
aacgaaactt ctcgatcttc ttttctttt tttcacctgt ttttcggtat cacgagaata      3120
ctacacttcc cactccagta atacgccact ccttcttttt ttttttgtct cgtttaaatt     3180
tttataaact ccataatttt atcttaaagt gaatcttttt tgtttttttt gttccagctt     3240
tatcggatat atttccttga ttttctccga ttgtggtcaa tctggaaaat tattgagaat     3300
ctctccctca cttaaccaaa agcgttttta atcagataga gagagaggaa aaagcatcaa     3360
ccaaacc                                                               3367
```

<210> SEQ ID NO 30
<211> LENGTH: 1353
<212> TYPE: DNA
<213> ORGANISM: Zea mays
<220> FEATURE:
<221> NAME/KEY: misc_feature
<222> LOCATION: 585
<223> OTHER INFORMATION: n = A,T,C or G
<221> NAME/KEY: misc_feature
<222> LOCATION: 585
<223> OTHER INFORMATION: n = A,T,C or G

<400> SEQUENCE: 30

```
gtgccttatg cctgtgtatg cttttgatcc agatatgaga aaagcattat cacaagatgt        60
tgagaagaag tccatcatac cactcaagag gccaattacg cctgatgaac ttgaatatga       120
ttgatgttag ctacctggtg cttacgttgg atgctccggt ggggaatttg acaggctttg       180
aaaatctggt agtgagtgta ttgttgtcgt ttttacgcct gctaggggac aggttttgat       240
```

```
ggtgaattct gcagtttttg tatttgagaa tagcaagaac tatgacttgg catggaatca      300
aattgctttg ttgtgatgtc gtatttatcc gtcgctgttt gctctgtagt gtgttttat      360 acagcttgca taatatataa gttatattcg acccgtgcta agcggtgata ggtagaattt      420
aacctactgg caattcagtg cctgagatca tgaatggcac cgtgagcttg tcaatcaaat      480
gataagtgac catcactcat gactcatcgc ccttccacat gttgtgggcg cgcatagggt      540
aatagatcgt gatttaaatg gttcttcata aaatgtcaag gtccnaaata aattatagtt      600
caaaaatgat tagaaataga gtctaattct aatccaattc gatccttaaa tattatagtg      660
taaaatttat agcccattat tagccctagg cgcgcatgca agtgacctca ttccgaaaaa      720
cattactctg cacaatggtg gtaaagtaga agggtgaggc agaggagacc aaacagggaa      780
aatgaggtga aaatcaacac tgattcaagc agcaatacac ggtgcaacag gtcatgtgct      840
tgatatgctg gttctcaggt gcgggaaggc tgccggtgcc agagttaaat gtatgttaag      900
gtcttaggaa ttttcaaaaa aaaaaaaaaa gttggaccgg cgaggttaat gtgcagactt      960
aggtcattga acaatgaat agtttcagta cattgtttct aaggttgtca aacagaaggc      1020
tatttatata aaactctcat atctctcctc tgtcaccccg tttgcttagg tgatatgtca      1080
tttaataaaa atgaaactcc cactatgaat ggccttagga gttaggacat caaaaggttc      1140
attcagaatt aaaaatgtcg gggtatcgga tgcttcaact tatttggata cttgaatttc      1200
aaacaaattc aaaaattcag agcattcggt gtttcttttg cttcaaaatt cttgcccatt      1260
tttggtctgt caagttttg aaatgagatg tttagattag ttggccagta aaataacaa      1320 atgcaaaagg cattttatgg agagatgcag cta                                  1353

<210> SEQ ID NO 31
<211> LENGTH: 795
<212> TYPE: DNA
<213> ORGANISM: Glycine max

<400> SEQUENCE: 31
ggtgatcact ggtccgtaca tttcgatttt ttcactttg tactgtaaaa tcagtctaaa       60
gtgacgagga ttcgaaatga aacaagttgg agaaaatata aaaagcgaaa tgcaggaaaa     120
caaaaaatga tagccattaa ttttaaaata agttaatctc acgatttaaa tgtttacttt     180
tgtaccattt caaattttgt cactttagta tcttaaaatg ggtctaaagt gacgatggtc     240
ggaaatgaaa gaaggttttg tagtaggact ttacttctac tctttttca caactttctc     300 tctctttatt ttttctttta atttattgga tacgtgtctc ctttttttcc tatataatga     360
cactctctgc agtgctttgg atctgtgact ctagtacttc tctctctctc tgtcattggt     420
ttttctctgg ttgacatcat cgtcatctac tacttcttcc tcttatccaa ttggccccca     480
acactggtac tacattagat ccttatgatt gatccatcat ggttttgtca taaaaaagtt     540
acaattgttt tcccctttaat tctatacatg ctgtgtttat aggcactttg ttgttttgcc     600
ttctctactt tgtgtcttcc aaccatacag ttttcattgt caatgtctcc attgtagatg     660
atgttgtttt gattttccta tgttcaagtt ttgttttct tttttgttt tttatgtgg        720 gttttggttg tttcggatc ttttggtgtg acccttcga tgttggcagg ttttggggta       780
ctttgaaaag ttgca                                                       795

<210> SEQ ID NO 32
<211> LENGTH: 761
<212> TYPE: DNA
```

<213> ORGANISM: Glycine max

<400> SEQUENCE: 32

```
ccttgtctaa gttccttaac taattaatgg gtaggagctg atgactagtg ttttcgggtt      60
caatcgacat gtggtcgggc tttgatcagt caagtgtgag ggatgtttta ggaatttaga    120
cactggagaa tagtgatata ctacaaactt gaaaagaata tttaggtgat ccatgtatgg    180
aaatagaatg atattgttaa cctgatgtga gagatctatg ttggtaatgc aaattattca    240
atataactat taggagcgtt gttaagtgat ttagactctc tcactcgagg gatcgtgagt    300
agagtaggtt agtaaacgtg ataataatc atgtttatgt taaaaagaaa aaaratctat    360
tataattaca ttaagagtta gttttgacaa gcggagctta acacgtttca taattcattt    420
attttttat tccttcaagt ttcttgtctt gtagttaatt tacattaatt tatattaatt    480
aataaaccag agatttaagt tagatatata taactctaaa tataaataaa gttggtagac    540
tccatacttt tttagtttta ttattactta ttggtaggtt tgcgaaagag ttaaggatta    600
tcaacctcat ttttttttt acactctgcc tcactcaccc tctataaatt gaatgtctga    660
caagtccttt ttttcttcac atgacatctc tctttctttc cattctccgt gatctcaggc    720
gctagctagt tatcagttat tattgttgtc gttgaaggtt g                        761
```

<210> SEQ ID NO 33
<211> LENGTH: 2008
<212> TYPE: DNA
<213> ORGANISM: Sorghum bicolor

<400> SEQUENCE: 33

```
atagtctttt cctttaatct catccttttg tttttgagat gtctaattga tggagtgaca     60
gattagtttg ctgctttgct catacgtgac aacgaactac tgttagaata gaacattttg    120
cagtgctaat atttgcatat gggaattaat taatttggga attatgtctt gccatggctg    180
atccagatct cgacacctgc tcgatctaat gcacacatgc gtgttgatag ggatgtagag    240
atataaggcg ttaggagatg tggtgtggta gtatatgcaa ggtcaaaatt cgatgctttt    300
tccatgtttc tttgaaaacg caatgccgca ttttctttta aagtaagaat tgaggggtcc    360
catgtttctt tttgcacttt ttcacatcga tgtataactg aaaatctcat gaaacatcat    420
tacctctttta tatgcgtcat catctttttca acaaaactca ctgatagcat tgatgcactt    480
acactcatac gtgacaacta ctgctattga aagtggacat ttgcagtgct actttttgca    540
tatatgggaa attgggaatt ctatattgcc atggttgatc cagatctcga cctactcgac    600
taatacatgt tgacagcaag ctgaggatcg ggacatgtaa taaggagtta ggagatgtgg    660
tgtggtacta aatgcaaggt caaaattcga tgcttttttcc gtgctcaact attaactagt    720
actcattatt acctaatttt cacttgtgat gacaattaat gcatcgatcc acaattcagt    780
aaatactttc atttaagcat atgtatagta ttatacattt ccaattcttc ttttttgtgt    840
ggagatccac gacgatgcaa gttgctcctc ccaacccaaa tccacctctc tcttaaatcc    900
gcatatcttc accaccacca gctgctacac atcgtattgt ccaaatctgt gtcggcttga    960
cccagtgatg tgcgcgctag atttggcagc gcctgaatgc tgtgcagcca cctgtatggt   1020
gcccttggta gagtaacaac acccttatcc ctacggcagc catgtatgac ccttatccct   1080
acggcagcca tgtataccaa tacctttctt tgaaccacaa aattatagtc catatcctta   1140
accacaagtt catttttgt ttcccggtct cctaaggaaa ttaagttctg tttccacaat   1200
ttacatggat ataggacatc tatgttccta acattaacat tactggataa caggcaccct   1260
```

```
ctcctccaca ccctgcaaag ccttcctcca gcgccatgca tcctccgttg ctaacagaca   1320
cctctctcca catcgcgtgc aagcaaacct ccaaattcta ccgatcccca gaatccggcc   1380
ttgactgcaa acagacaccc ctctccccat cctgcaaacc catcagccaa ccgaataaca   1440
caagaaggca ggtgagcagt gacaaagcac gtcaacagca gcaaagccaa gccaaaaacg   1500
atccaggagc aaggtgcggc cgcagctctc ccggtcccct ttgcggttac cactagctaa   1560
gaatgaagat ggtactctaa atggatactt gcgcggtttt tctctagtct aacttaataa   1620
actaaataaa caatttcttt cttatttttt taatttagtt cgtttagtta gactagagaa   1680
gaaccacgag gagttatttg aagcgtcgtc cccatcctta ccactagcta gcactagcag   1740 acaccctct ccacgtcctg caaacaggca attagccagc ggaataacac aagcaggcaa    1800
gtgcgcagtg acaaagtacg tccacagcag cgatcccagc caaaagcagc gtagccacag   1860
ccgcgcgcag ctctcggcta cccttaccgc cgatcacatg catgcctttc caatcccgcg   1920
tgcacacgcc gaccacacac tcgccaactc cccatcccta tttgaagcca ccggccggcg   1980
ccctgcattg atcaatcaac tcgcagca                                      2008

<210> SEQ ID NO 34
<211> LENGTH: 3188
<212> TYPE: DNA
<213> ORGANISM: Sorghum bicolor

<400> SEQUENCE: 34
cctccgcatt agtggattct aaaacctctt ttttttttcat gaaattctat cacggcctag     60
tactagtagt cccctcctct tgagaatacc gagagtataa gcattggttg gggttcaatt    120
tgtttagttc gaatgattga tgagaagctt tatttattta tttactggag atgacaacca    180
aatgttgggg caggatacag aaaagaaaaa caacactctc tttggacggt gccagcttca    240
acggccgacc aaaataatac tactacactt ctagtgcgtg ctgactttga tgaggtgtcc    300
caaatagagt acgtagatga ataggagtat ttgtttctttt gggggttcc ttttcagaaa    360 gccttttctt attcgtccat gtcacggaga ccaaataaaa ttgggtgggc gtgacaattg    420
gcgtcagctt gacacgatag tccaccagag gcggcaatca gaggccgtgc caaaagaaa    480 tttcatcatc aaggaaattc aagtttctcg ttccaccaca ttccacgcag tgcaagactc    540
cattaatcca aactactgta gctactagct attcgtccca tcatcttttc ttagatattt    600
atttatttac tttttctata agcaaagttt cttagacaaa atcagtccca acttgactaa    660
cgtaggaata taattcgtaa ggtcggagca aaataattct gctcgatgta atcatacccta   720 cacgtacatg tggcggcaat cgttgcttga gaaaaaacaa atacctaact gttttgcaat    780
agcagcaatc atttaggttc aaaaaggaaa tgataataca acggttacat taccccatag    840
acaaaatttt ccttatagtt gttgcaaatt acgatgcgtg agcctctgat taaaaggtaa    900
agtattgata acaaattcat gggtgggagt tagcgcatac gtacaacacc actagtcaag    960
cactaatttg tactactaac tcctcaaatt ttaaagcaga taaaacttat gaaaatcaag   1020
agaagtgaaa tgaaaattga cgaattataa ccccatgacc attttttctct acgtcatcat   1080 caaatgacat ttgcatgact ttatcttgat ttacgatgtg aacaaccag gaaaatgaga     1140 aagaagaaat tgaccaagca tgtcataata ttcatttttt tctataattt ttcaacagag   1200
tctgactttt gcatggcttt ccttgaagtt gcataaagag atgatcatgc aaaagttgga   1260
ctgttgttat tggccaagcc ttttttttcc tttgctttga ccatcaagaa tagataatcc   1320
```

```
ctttcctatt acctttggtc tacagtaatg atccataaca cactatgaac aaaacacaag    1380
caagtactga ttttcaagaa attgaaaaat gattagatga ccttccagag ccctattgaa    1440
aaataagcaa gttggaaagg gagtgggact gagaatatta caatagctac attcttggca    1500
gtctcgatag acaagtgtca catagcattt tattccaaga ctatgtacaa gtatgttgta    1560
gaacaaaggg actattgttt aagatagcat atttcataaa tatttgtttt gaatagaatg    1620
ttttcaaaga tatgattcat cgaagtggca tattggaggt cttatctatt ttcttgtcga    1680
ttaataaggg tgcatttagt agggtccttt ctattttctt gttcacttta caataaatca    1740
accaacagta atttcaacca tgattttagc cagcagtgtt tttcttccca tgtgattaat    1800
caaaactcct ttgtaatatc atttgattag tagactgaat tttggtccac atgaagatat    1860
atatatatat atattaaaag tcatataaat aaaaatatgc ttaaaaatta taaacctttt    1920
gtgggtgaag aataatttaa atacaaccca ttttagtttg ttgtaataaa aaaggattac    1980
aaatgaaaaa aaaattaaaa ttggtagctt gcaagtgcat caaagaatcc agatcagttt    2040
tgtgtggaac gaacgtgtcc taatttctaa ctttgctgaa gaaacgcag aactgaaacg     2100 ttttggatct agacagaacg acgtttagag ccattttct agtgattcat gtgagaaatg     2160
aacctgattc tcacacatcc aaacggccca caagtatact gcttcgactt tttttttca     2220 tgagaatgag atgcacgaca atgcacacat cacgcctcac gcggcactct gatgtcccaa    2280
cattcctaat taaagtattc cggtgatgca atggatggaa gtaaactgaa aaactagatt    2340
ggtgtctaat aataatatac tcctactaaa gactagagat atattcatag atttaaatcc    2400
cttacttaca aagggtcgca caacttgtgt ttagttgaag gagttctcta aaatttgtat    2460
ggacaatagg tacacaaatt tttattatct tagaccttgt ttagttcaaa aaaattttca    2520
aggttctctc acgtcaaatc tttggacgca tgcatgaagc attaaataca gataaaaaat    2580
aactaattgc atagtttatc tctaatttgc aagacaaatc ttttaggctt aattagtcta    2640
tggttggaca ataattgtca atactccctc cgtataggat ttagaatttg tttaggacag    2700
cgacacggtc tccaaaatac aactttaacc tcttattttt tataaaaata tttagaaaaa    2760
tgatatatgt atacttttat aaaagtattt ttcaagacaa atctattcat gtaacttta     2820 tatttacaaa ctcaataatt taagagttat taatgattta tattccaata tttgacacaa    2880
actttgtcca aaacgacttc taaatcctat acgaaaagtg tacaatagtc aaattttaaa    2940
aaaaattcag gaactaacaa agcctccaaa actactagta caacttcaaa taatccccaa    3000
gttcacgggg atcaatctgc aaaagtagga gtacttgtac ttggcatgat gagtcatggg    3060
catgagggag acccacggtt gagcaacata aaattctcca aacgggcccc accaccacac    3120
acgatcacca tcaccccccgg gctccccgtc ccccgtaca aataggcacg gcacactccc    3180
aactcccc                                                             3188
```

NITRATE REDUCTASES FROM RED ALGAE, COMPOSITIONS AND METHODS OF USE THEREOF

CROSS REFERENCE

This utility application claims the benefit U.S. Provisional Application No. 60/944,343, filed Jun. 15, 2007 which is incorporated herein by reference.

BACKGROUND OF THE INVENTION

The domestication of many plants has correlated with dramatic increases in yield. The identification of specific genes responsible for the dramatic differences in yield, in domesticated plants, has become an important focus of agricultural research.

One group of genes effecting yield are the nitrate reductase genes. These genes have utility for improving the use of nitrogen in crop plants, especially maize. The genes can be used to alter the genetic composition of the plants rendering them more productive with current fertilizer application standards, or maintaining their productive rates with significantly reduced fertilizer input. Increased nitrogen use efficiency can result from enhanced uptake and assimilation of nitrogen fertilizer and/or the subsequent remobilization and reutilization of accumulated nitrogen reserves. Plants containing these genes can therefore be used for the enhancement of yield. Improving the nitrogen use efficiency in corn would increase corn harvestable yield per unit of input nitrogen fertilizer, both in developing nations where access to nitrogen fertilizer is limited and in developed nations were the level of nitrogen use remains high. Nitrogen utilization improvement also allows decreases in on-farm input costs, decreased use and dependence on the non-renewable energy sources required for nitrogen fertilizer production, and decreases the environmental impact of nitrogen fertilizer manufacturing and agricultural use.

Many efforts have recently been made to improve nitrogen efficiency of crop plants through overexpression of nitrate reductase (NR) in plants. One group has applied expression of the *Nicotiana plumbaginifolia* & *Arabidopsis thaliana* NR cDNA or gene under control of different promoters such as 35S CaMV (*Nicotiana plumbaginifolia*) Ferrario, et al., (1995) "Effects of constitutive expression of nitrate reductase in transgenic *Nicotiana plumbaginifolia* L. in response to varying nitrogen supply" *Planta* 196:288-294; and Lhcb1*3:: Nia1*2 (*Arabidopsis thaliana*) Nejidat, et al., (1997) "Increased protein content in transgenic *Arabidopsis Thalina* over-expressing nitrate reductase activity" *Plant Science* 130: 41-49. (references). Although increases in NR expression levels up to 2-5-fold were detected with the 35S CaMV:: Nia-2 gene in *Nicotiana plumbaginifolia* plants (Foyer, et al., (1994) "Adaptations of photosynthetic electron transport, carbon assimilation and carbon partitioning in transgenic *Nicotiana plumbaginifolia* plants to changes in nitrate reductase activity" *Plant Physiol.* 104:171-178), no improved nitrogen efficiency was observed. All these attempts to over express this enzyme have not resulted in improved growth under lower nitrogen fertility.

Therefore, despite several attempts to improve NR efficiency, no satisfactory composition or method has been provided that leads to an improvement of growth, productivity, and/or yield for agricultural crop plants. For these and other reasons, there is a need for the present invention.

BRIEF SUMMARY OF THE INVENTION

The present invention provides polynucleotides, related polypeptides and all conservatively modified variants of the present NR sequences. The invention provides sequences for the NR genes.

The present invention presents methods to alter the genetic composition of crop plants, especially maize, so that such crops can be more productive with current fertilizer applications and/or as productive with significantly reduced fertilizer input. The utility of this class of invention is then both yield enhancement and reduced fertilizer costs with corresponding reduced impact to the environment.

Therefore, in one aspect, the present invention relates to an isolated nucleic acid comprising an isolated polynucleotide sequence encoding an NR gene. One embodiment of the invention is an isolated polynucleotide comprising a nucleotide sequence selected from the group consisting of: (a) the nucleotide sequence comprising SEQ ID NO: 1, 2, 3, 4, 5 or 6; and (c) the nucleotide sequence comprising at least 70% sequence identity to SEQ ID NO: 1, 2, 3, 4, 5 or 6 wherein said polynucleotide encodes a polypeptide having increased NR activity.

Compositions of the invention include an isolated polypeptide comprising an amino acid sequence selected from the group consisting of: (a) the amino acid sequence comprising SEQ ID NO: 7, 8, 9, 10, 11 or 12 and (b) the amino acid sequence comprising at least 70% sequence identity to SEQ ID NO: 7, 8, 9, 10, 11 or 12 wherein said polypeptide has increased NR activity.

In another aspect, the present invention relates to a recombinant expression cassette comprising a nucleic acid as described. Additionally, the present invention relates to a vector containing the recombinant expression cassette. Further, the vector containing the recombinant expression cassette can facilitate the transcription and translation of the nucleic acid in a host cell. The present invention also relates to the host cells able to express the polynucleotide of the present invention. A number of host cells could be used, such as but not limited to, microbial, mammalian, plant, or insect.

In yet another embodiment, the present invention is directed to a transgenic plant or plant cells, containing the nucleic acids of the present invention. Preferred plants containing the polynucleotides of the present invention include but are not limited to maize, soybean, sunflower, sorghum, canola, wheat, alfalfa, cotton, rice, barley, tomato, and millet. In another embodiment, the transgenic plant is a maize plant or plant cells. Another embodiment is the transgenic seeds from the transgenic NR polypeptide of the invention operably linked to a promoter that drives expression in the plant. The plants of the invention can have altered NR as compared to a control plant. In some plants, the NR is altered in a vegetative tissue, a reproductive tissue, or a vegetative tissue and a reproductive tissue. Plants of the invention can have at least one of the following phenotypes including but not limited to: increased root mass, increased root length, increased leaf size, increased ear size, increased seed size, increased endosperm size, and increased biomass Another embodiment of the invention would be plants that have been genetically modified at a genomic locus, wherein the genomic locus encodes a NR polypeptide of the invention.

Methods for increasing the activity of a NR polypeptide in a plant are provided. The method can comprise introducing into the plant an NR polynucleotide of the invention.

Methods for reducing or eliminating the level of NR polypeptide in the plant are provided. The level or activity of the polypeptide could also be reduced or eliminated in specific tissues, causing alteration in plant growth, growth rate or nitrogen utilization efficiency (NUE). Reducing the level and/or activity of the NR polypeptide may lead to smaller stature or slower growth of plants.

BRIEF DESCRIPTION OF THE DRAWINGS

The invention can be more fully understood from the following detailed description and the accompanying drawing and Sequence Listing which form a part of this application.

FIG. 1. Peptide sequence comparison between *Porphyra perforata* (PpNR—SEQ ID NO: 5) and *P. yezoensis* (PyNR—SEQ ID NO: 10). PpNR and PyNR are approximately 94% identical. The identical amino acid residues are in bold and similar ones are underlined.

Maize nitrate reductase ZmNR was cloned from maize B73 (assembled from two truncated ESTs) based on the published genomic sequence (GenBank Accession Number AF153448). The cloned ZmNR has three different amino acid residues compared to AF153448. The KM71-containing YNT1 line was re-transformed with nitrate reductase gene ZMNR driven by GAP promoter with Zeocin selection marker (pAOXGAP-ZMNR) which integrated into AOX1 locus of *P. pastoris* genome. The transformant with the best Vmax was used for kinetic study.

The transformants carrying YNT1/YNR1, YNT1/ZMNR, or YNT1/PPNR, and KM71 wild type were cultured in rich media (YPD) at 30° C. for overnight. Yeast cells were collected and washed with water twice then re-suspended in 20 μM MOPS, pH6.5, or 20 μM MES, pH5.5, or 20 μM Tris, pH7.5 with 1% glucose containing 24 different concentrations of NaNO$_3$ from 0 up to 30 mM (0, 0.02, 0.04, 0.06, 0.08, 0.1, 0.12, 0.14, 0.16, 0.18, 0.2, 0.3, 0.4, 0.6, 0.8, 1, 2, 4, 8, 10, 15, 20, 25 and 30 mM). The reduced nitrite was assayed as mentioned above. The Km was estimated as the substrate concentration at ½ Vmax. The Km and preferred pH (with the best Vmax) of YNR1, ZMNR, and PPNR was summarized in the table. Please note that although the diagram shows YNR1 as the lowest line on the chart, only one tenth the volume of YNR1 material was used in the experiment, therefore the YNR1 had the best Vmax in the experiment.

Figure 2:
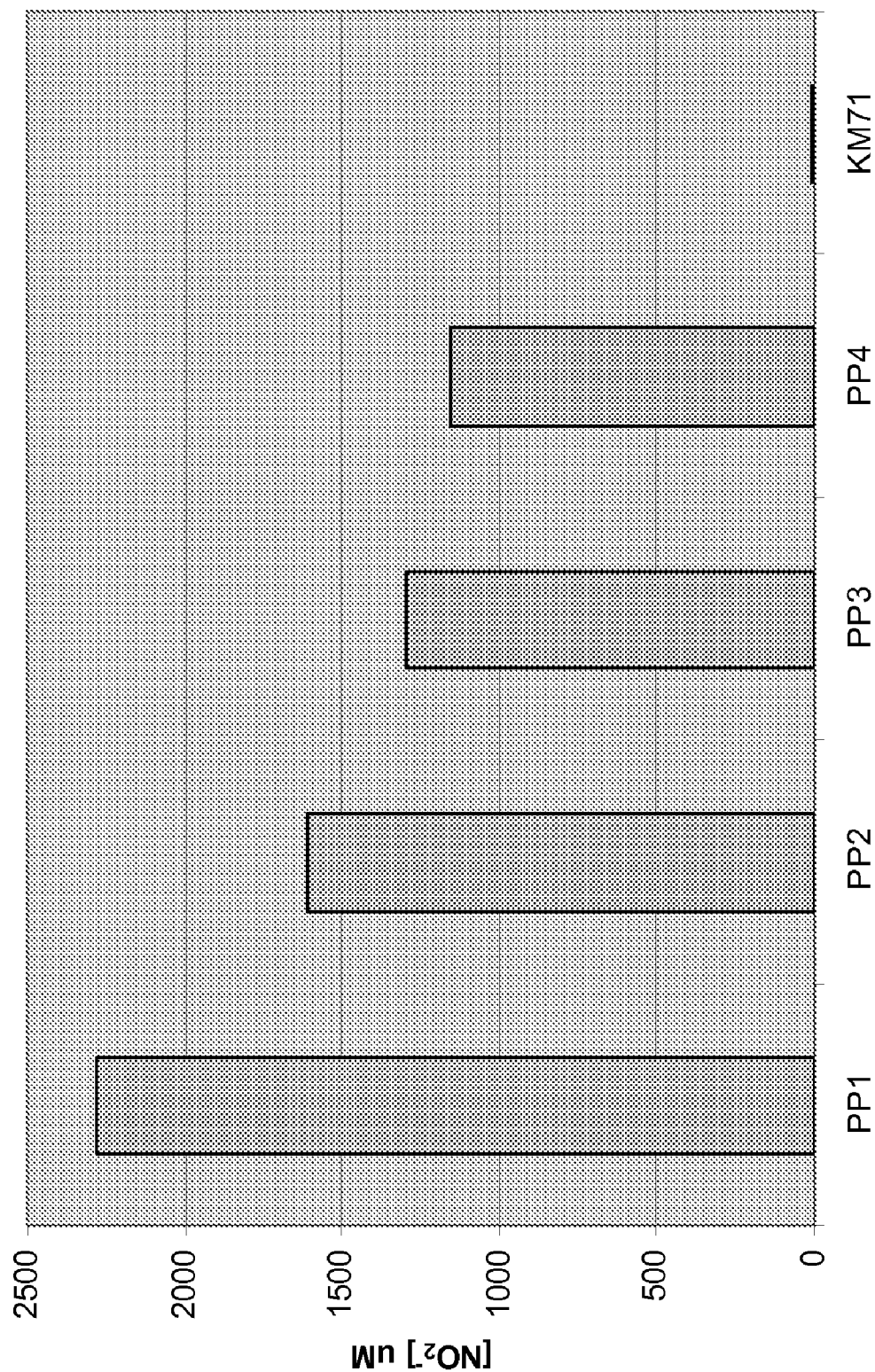
FIG. 2. Yeast nitrate transporter YNT1 was cloned from *Pichia angusta* based on the published sequence (GenBank Accession Number Z69783). YNT1 driven by a constitutive promoter glyceraldehyde-3-phosphate dehydrogenase (GAP) from *P. pastoris* with histidine auxotroph selection marker (p3.5GAP-YNT1) was integrated into His4 locus of *P. pastoris* strain KM71 (Invitrogen) using *Pichia* EasyComp transformation kit (Invitrogen). The recombinant strains were confirmed to carry the YNT1 expression cassette by PCR. The KM71-containing YNT1 line was re-transformed with nitrate reductase gene PPNR from *Porphyra perforate* driven by GAP promoter with Zeocin selection marker (pAOXGAP-PPNR) which integrated into AOX1 locus of *P. pastoris* genome. Nitrate reductase enzyme activity was assayed in vivo. Four transformants and KM71 wild type were cultured in rich media (YPD) at 30° C. for overnight. Yeast cells were collected and washed with water twice then re-suspended in 20 uM MOPS, pH6.5 and 1% glucose containing 5 mM NaNO$_3$. After 1 hour incubation at 30° C., the supernatant was collected for nitrite assay with 1% Sulfanilamide, 0.01% N-(1-Naphthyl)ethylene-diamine dihydrochloride and 15% (v/v) H$_3$PO$_4$. Strong NR activity was detected in transformants carrying PPNR comparing to KM71 wild type strain.
Figure 3:
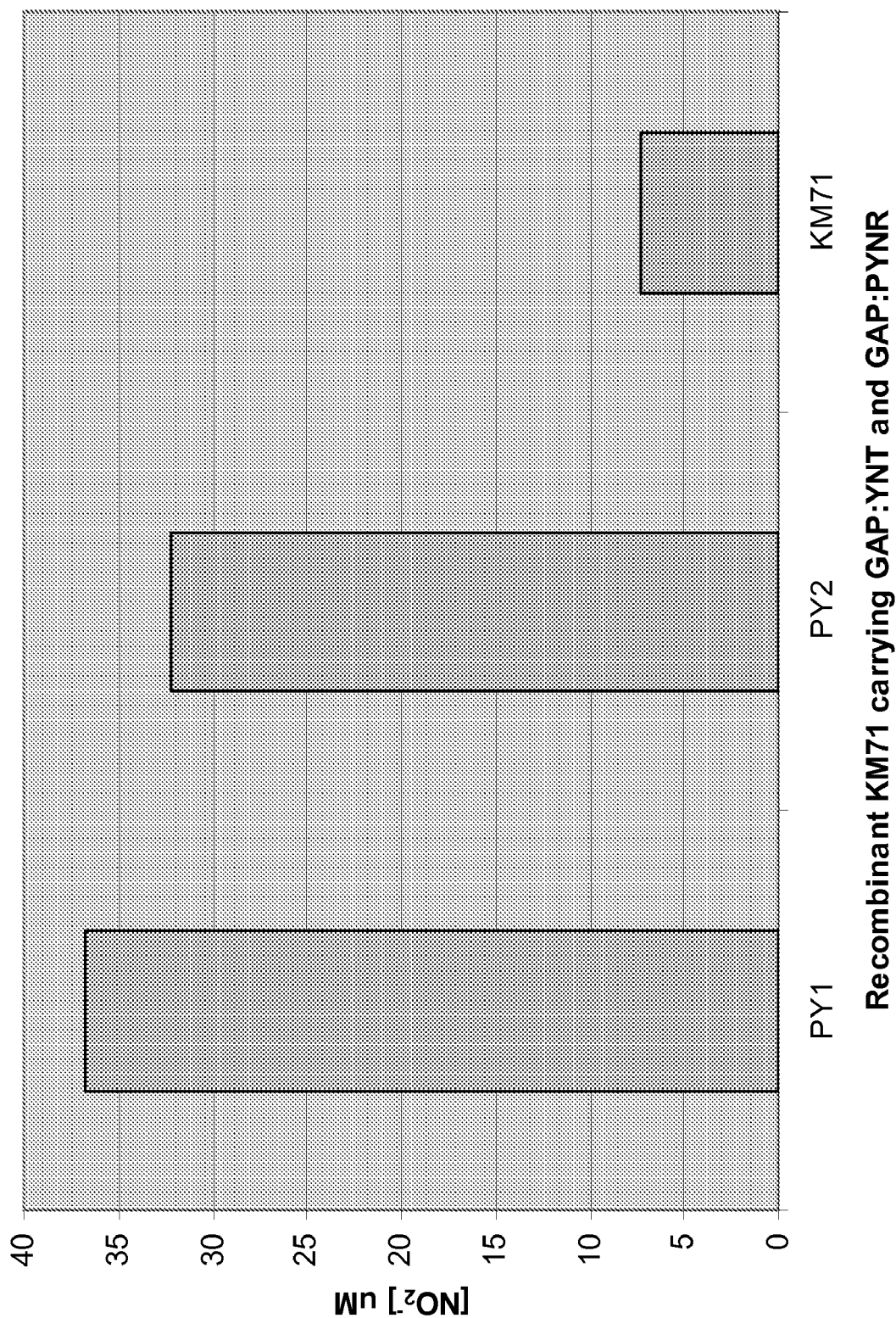
FIG. 3. The KM71-containing YNT1 line (see FIG. 2) was re-transformed with nitrate reductase gene PYNR from *Porphyra yezoensis* driven by GAP promoter with Zeocin selection marker (pAOXGAP-PYNR) which integrated into AOX1 locus of *P. pastoris* genome. In this case, the nitrate reductase enzyme activity from two transformants and KM71 wild type was assayed in vivo as before. The NR activity was detected from the transformants carrying PYNR comparing to KM71 wild type strain. However, the PYNR activity is much weaker then PPNR in *P. pastoris*.
Figure 4:
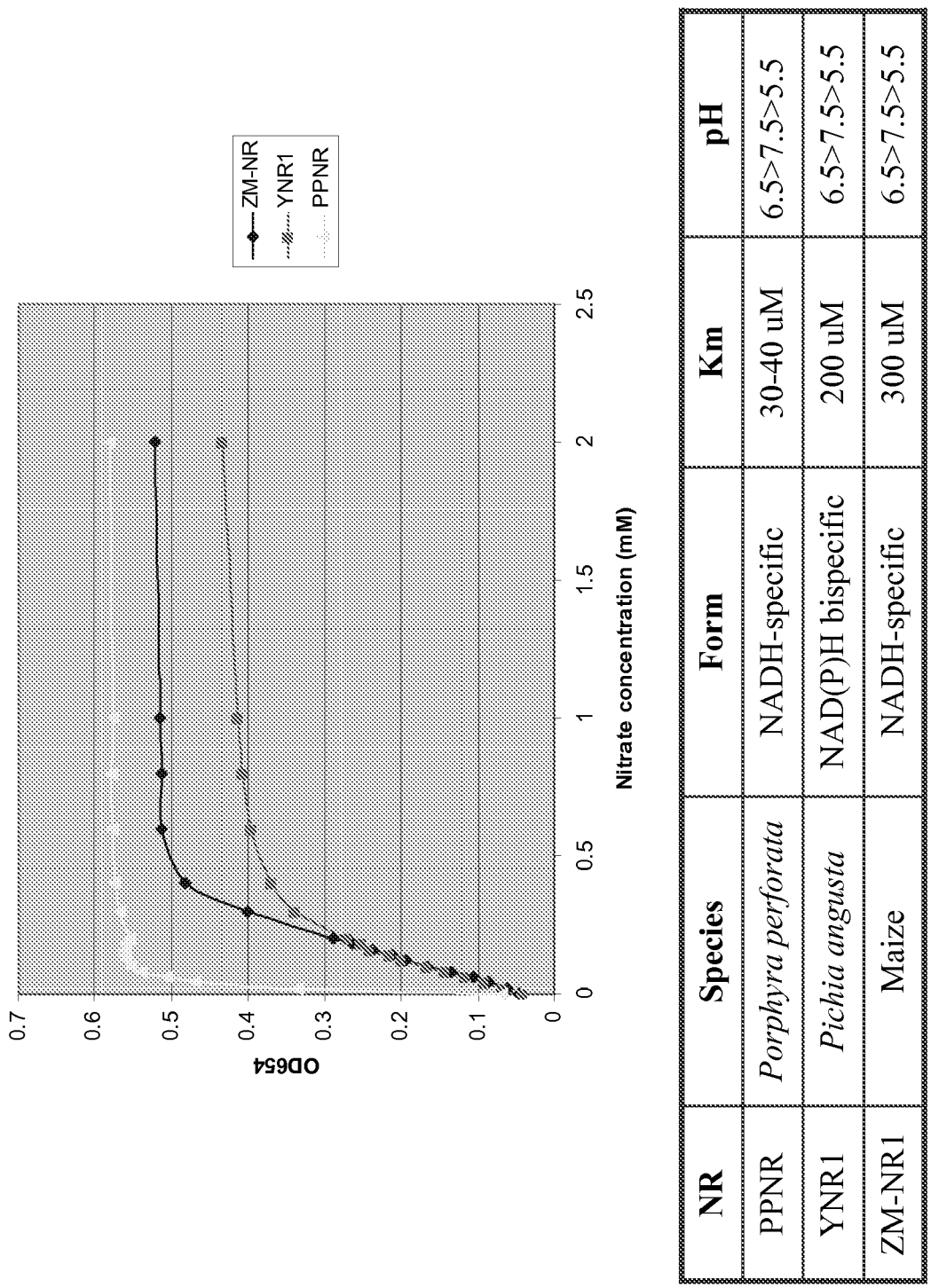
FIG. 4. Yeast nitrate reductase YNR1 was cloned from *Pichia angusta* based on the published sequence (GenBank Accession Number Z49110). The KM71-containing YNT1 line was re-transformed with nitrate reductase gene YNR1 driven by GAP promoter with Zeocin selection marker (pAOXGAP-YNR1) which integrated into AOX1 locus of *P. pastoris* genome. The transformant with the best Vmax was used for kinetic study.
Figure 5:
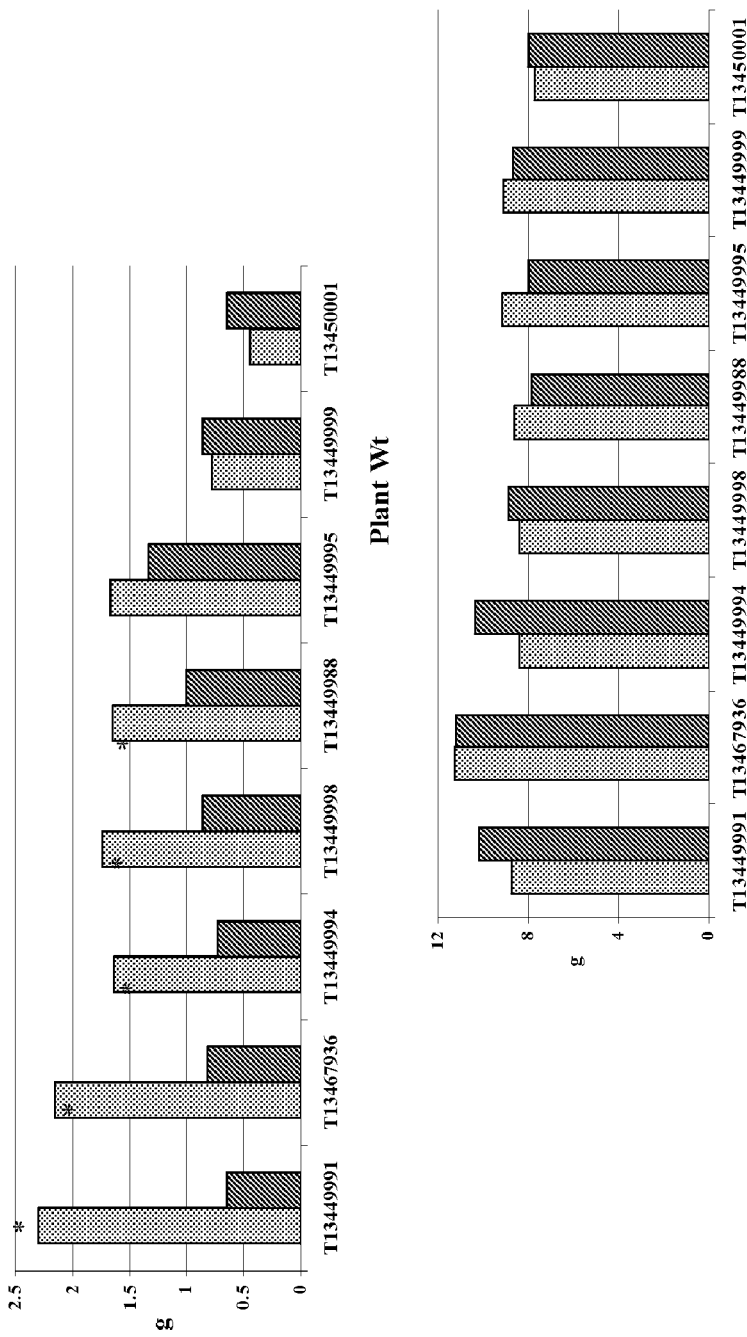

FIG. 5. The constructs of PPNR and PYNR driven by UBI promoter and/or maize nitrate reductase ZMNR promoter were made. The resulting constructs, PHP27800, PHP27801, PHP28335, and PHP28334 were used for maize transformation. Transgenic maize segregating 1:1 for UBI:*Porphyra perforata* NR was grown to anthesis in hydroponics medium maintained at 1 mM KNO$_3$ as the sole nitrogen source. Plants containing the transgene were identified during growth. All plants were harvested shortly after anthesis. The ear and the remaining plant were separated, dried in a forced air oven at 70° C. for 72 hr and weighed. Mean ear dry weight of each event transgenic plants were compared to the ear dry weight of the corresponding nulls. Similar comparisons were made between transgenic mean plant dry weight and the corresponding event nulls. Comparisons marked with * are statistically significant (p>t=0.1). This figure is a graphical representation of the data described in Example 10.

BRIEF DESCRIPTION OF THE SEQUENCES

The application provides details of NR sequences as shown in Table 1 below.

TABLE 1

| SEQ ID NO: | Polynucleotide (pnt) or polypeptide (ppt) | Length | Identification |
| --- | --- | --- | --- |
| 1 | pnt | 2865 | PpNR. |
| 2 | pnt | 2865 | Codon optimized polynucleotide sequence encoding PpNR S561Ala |
| 3 | pnt | 2865 | Codon optimized polynucleotide sequence encoding PpNR S561Asp |
| 4 | pnt | 2871 | PyNR |
| 5 | pnt | 2871 | Codon optimized polynucleotide sequence encoding PyNR S563Ala |
| 6 | pnt | 2871 | Codon optimized polynucleotide sequence encoding PyNR S563Asp |
| 7 | ppt | 954 | PpNR. |
| 8 | ppt | 954 | PpNR S561Ala - encoded by codon optimized polynucleotide |
| 9 | ppt | 954 | PpNR S561Asp - encoded by codon optimized polynucleotide |
| 10 | ppt | 954 | PyNR |
| 11 | ppt | 956 | PyNR S563Ala - encoded by codon optimized polynucleotide |

TABLE 1-continued

| SEQ ID NO: | Polynucleotide (pnt) or polypeptide (ppt) | Length | Identification |
|---|---|---|---|
| 12 | ppt | 956 | PyNR S563Asp - encoded by codon optimized polynucleotide |
| 13 | pnt | 26 | PYNR sense primer |
| 14 | pnt | 20 | PYNR anti-sense primer |
| 15 | pnt | 20 | PpNR walking primer |
| 16 | pnt | 20 | PpNR walking primer |
| 17 | pnt | 20 | PpNR walking primer |
| 18 | pnt | 25 | PpNR walking primer |
| 19 | pnt | 24 | PpNR walking primer |
| 20 | pnt | 25 | PpNR walking primer |
| 21 | pnt | 21 | ORF PpNR sense primer |
| 22 | pnt | 21 | ORF PpNR anti-sense primer |
| 23 | pnt | 19 | ORF PyNR sense primer |
| 24 | pnt | 22 | ORF PyNR anti-sense primer |

DETAILED DESCRIPTION OF THE PREFERRED EMBODIMENT

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Overview

Nitrate is the most important source of nitrogen for higher plants. Nitrate is absorbed by the roots, transported to various tissues of the plant and then reduced to aqueous ammonia in two steps. The first step requires the enzyme nitrate reductase (NR), which catalyzes the reduction of nitrate to nitrite in the cytoplasm. In a second step, the nitrite is then reduced in the chloroplast by nitrite reductase. The reduction of nitrate is considered to be limiting step in nitrate metabolism in plants.

Plant nitrate reductases are regulated at both transcriptional and post-translational levels. Several environmental factors such as light or nitrate regulate NR gene expression at transcriptional level. NR activity is also regulated at post-translational level by light. NR becomes inactive/active in response to dark/light by phosphorylation/dephosphorylation at putative Ser residues. The inactive form of NR binds to 14-3-3 protein in the dark. The putative regulation sites include N-terminal region (*Plant Cell* (1995) 7:611-621), hinge 1 (*Plant J.* (2003) 35:566-573) and other regions.

The present invention relates to the discovery of novel NRs from red algae (division of Rhodophyta) of *Porphyra perforate* (PpNR) and *Porphyra yezoensis* (PyNR). As described herein, the inventors have identified two novel NR cDNAs in red algae that share approximately 94% amino acid consensus with respect to one another but only 52% amino acid identity to a maize homolog of NR from B73 (Genbank Acc NoAF153448). The algal NR polynucleotides of this invention are 2865 bp (PpNR) and 2871 bp (PyNR), nucleotides in length encoding polypeptides with calculated molecular weight of 104.9 KDa (PpNR) and 105.2 KDa (PyNR). Also contemplated are variants of these sequences. For example, mutating the serine residue in a putative phosphorylation motif R/K-S/T-X-pS-X-P (*J of Experimental Botany* (2004) 55:1275-1282) at position 561 to an alanine or aspartic acid of the PpNR or an alanine or aspartic acid at position 563 of the PyNR sequence is believed to increase and maintain high level of active form of nitrate reductase in transgenic plants to facilitate nitrate assimilation.

Red algae (division of Rhodophyta) of *Porphyra perforate* (PpNR) and *Porphyra yezoensis* (PyNR) grow in concentrations of nitrate that are approximately one hundred times lower than the nitrate concentrations in which plants are capable of growing. These red algae have more efficient nitrate reductase enzymes that saturate at lower substrate concentrations than higher plant nitrate reductase. In particular, *Porphyra perforate* and *Porphyra yezoensis* have been reported in the literature to have a NR enzyme with a low Km for nitrate (30-65 µM). This is in contrast to a maize NR from B73 which has a Km for nitrate reductase of 300 µM. In vivo kinetic measurements made of PpNR and PyNR expressed in *Pichia pastoris* show this enzyme has a Km for nitrate of 30-50 µM compared to maize nitrate reductase Km of 200 µM. Without wishing to be bound by this theory, it is believed that expressing more efficient NRs that saturate at lower concentrations of substrate than the higher plant NR enzymes will be more efficient in nitrogen reduction. Modulation of the NRs of the present invention would provide a mechanism for manipulating a plant's nitrogen utilization efficiency (NUE). Accordingly, the present invention provides methods, polynucleotides, and polypeptides for the production of plants with improved or maintained yield under limited nitrogen supply. In one aspect, the methods include introducing into a plant cell, plant tissue or plant one or more polynucleotides encoding NR polypeptides having the enzymatic activity of nitrate reductase. This may be accomplished by introducing the nitrate reductase polynucleotides driven by a constitutive promoter or a mesophyll cell preferred promoter into the plant nuclear genome.

Advantageously, plants expressing a NR of the present invention will provide the customer increased revenue by lowering input costs and/or increasing yields with a significant reduction in applied nitrogen fertilizer. Furthermore, yields may be maintained or increased in plants expressing a NR of the present invention even under non-favorable growth conditions, for example, where nitrogen is in limited supply.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982)

*Botany: Plant Biology and Its Relation to Human Affairs*, John Wiley; *Cell Culture and Somatic Cell Genetics of Plants*, vol. 1, Vasil, ed. (1984); Stanier, et al., (1986) *The Microbial World*, 5th ed., Prentice-Hall; Dhringra and Sinclair, (1985) *Basic Plant Pathology Methods*, CRC Press; Maniatis, et al., (1982) *Molecular Cloning: A Laboratory Manual; DNA Cloning*, vols. I and II, Glover, ed. (1985); *Oligonucleotide Synthesis*, Gait, ed. (1984); *Nucleic Acid Hybridization*, Hames and Higgins, eds. (1984); and the series *Methods in Enzymology*, Colowick and Kaplan, eds, Academic Press, Inc., San Diego, Calif.

Units, prefixes, and symbols may be denoted in their Si accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

DEFINITIONS

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular *Microbiology: Principles and Applications*, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins*, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) *Proc. Natl. Acad. Sci. USA* 82:2306-9), or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "NR nucleic acid" means a nucleic acid comprising a polynucleotide ("NR polynucleotide") encoding a full length or partial length NR polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual*, $2^{nd}$ ed., vols. 1-3; and *Current Protocols in Molecular Biology*, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. A particularly preferred plant is *Zea mays*.

As used herein, "yield" may include reference to bushels per acre of a grain crop at harvest, as adjusted for grain moisture (15% typically for maize, for example), and the volume of biomass generated (for forage crops such as alfalfa, and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions, for example, the ubiquitin gene promoter UBI (GenBank Accesssion Number S94464).

As used herein, the term nitrate reductase (NR) includes but is not limited to the sequences disclosed herein, such as NR, their conservatively modified variants, regardless of source and any other variants which retain the biological properties of the NR, for example, NR activity as disclosed herein. The term "NR polypeptide" refers to one or more amino acid sequences. The term is also inclusive of fragments, variants, homologs, alleles or precursors (e.g., preproproteins or proproteins) thereof. A "NR protein" comprises a NR polypeptide. Unless otherwise stated, the term "NR nucleic acid" means a nucleic acid comprising a polynucleotide ("NR polynucleotide") encoding a NR polypeptide.

As used interchangeably herein, a "NR activity", "biological activity of NR" or "functional activity of NR", refers to an activity exerted by a NR protein, polypeptide or portion thereof as determined in vivo, or in vitro, according to standard techniques. In one aspect, a NR activity is the reduction of nitrate to nitrite. In one aspect, NR activity includes but is not limited to increased nitrate reduction rate and/or specificity for nitrate, for example, decreased Km for nitrate and NADH, increased velocity (Vmax) for nitrate reduction and the like as compared to NR activity of an endogenous NR of a crop plant of interest. In another aspect, NR activity includes but is not limited to increasing NUE and/or plant productivity/yield as compared to a control plant. NUE may be inferred from amount and/or rate of nitrogen uptake from the soil or medium as described herein in Example 11.

The expression level of the NR polypeptide may be measured directly, for example, by measuring the level of the NR polypeptide by Western in the plant, or indirectly, for example, by measuring the NR activity of the NR polypeptide in the plant. Methods for determining the NR activity may be determined using standard techniques such as Hageman, et al., *Methods Enzymol.* (1971) 23:491-503, Tucker, et al., (2004). "Control of nitrate reductase by circadium and diurnal rhythms in tomato" *Planta* 219:277-285. and Scheible, et al., (1997) "Accumulation of nitrate in the shoot acts as a signal to regulate shoot:root allocation in tobacco" *Plant J.* 11:671-691, including the evaluation of activity in various expression systems, for example of *Xenopus* oocytes (see, Miller, et al., (2000) "*Xenopus* Oocytes as an Expression System for Plant Transporters", *Biochimica et Biophysica Acta* 1465:343-358.) or yeast such as *Pichia pastoris* (U.S. Provisional Patent Application Ser. No. 60/944,223 filed Jun. 15, 2007), NR activity may also include evaluation of phenotypic changes, such as increased or maintained yield or NUE in a plant grown under nitrate limiting conditions such as lower nitrogen fertility. Examples of phenoypic changes include but are not limited to increased ear size in maize, increased ear growth rate, increased biomass, higher grain yields, synchronous flowering so that pollen is shed at approximately the same time as silking, enhanced root growth, increased seed size, increased seed weight, seed with increased embryo size, increased leaf size, increased seedling vigor, enhanced silk emergence, and greater chlorophyll content (greener).

Maintained or increased yield may be achieved through NRs of the present invention. Thus, modulation of NR activity of the NRs of the present invention in a plant cell provides a novel strategy for maintaining or increasing yield or NUE of a plant grown under limited nitrogen supply or lower nitrogen fertility Accordingly, the present invention further provides plants having increased yield or a maintained yield when grown under limited nitrogen fertility. In some embodiments, the plants having an increased or maintained yield when grown under limited nitrogen fertility have a modulated level/activity of a NR polypeptide of the invention.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention; or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-84:

$T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part 1, chapter 2, "Overview of principles of hybridization and the strategy of nucleic acid probe assays," Elsevier, N.Y. (1993); and *Current Protocols in Molecular Biology*, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

Nucleic Acids

The present invention provides, inter alia, isolated nucleic acids of RNA, DNA, and analogs and/or chimeras thereof, comprising a NR polynucleotide.

The present invention also includes polynucleotides optimized for expression in different organisms. For example, for expression of the polynucleotide in a maize plant, the sequence can be altered to account for specific codon preferences and to alter GC content as according to Murray, et al, supra. Maize codon usage for 28 genes from maize plants is listed in Table 4 of Murray, et al., supra.

The NR nucleic acids of the present invention comprise isolated NR polynucleotides which are inclusive of:
(a) a polynucleotide encoding a NR polypeptide and conservatively modified and polymorphic variants thereof;
(b) a polynucleotide having at least 70% sequence identity with polynucleotides of (a);
(c) complementary sequences of polynucleotides of (a) or (b).

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, PGEM, pSK+/−, pGEX, pSPORTI and II, pOPRSVI CAT, pOP13 CAT, pXT1, pSG5, pPbac, pMbac, pMC1 neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20): 1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Publication Number 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A number of promoters can be used in the practice of the invention, including the native promoter of the endogenous NR polynucleotide sequence of the crop plant of interest. The promoters can be selected based on the desired outcome. The nucleic acids can be combined with constitutive, tissue-preferred, inducible, or other promoters for expression in plants.

A plant promoter or promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No.

5,683,439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); PEMU (Last, et al., (1991) *Theor. Appl. Genet.* 81:581-8); MAS (Velten, et al., (1984) *EMBO J.* 3:2723-30); and maize H3 histone (Lepetit, et al., (1992) *Mol. Gen. Genet.* 231:276-85; and Atanassvoa, et al., (1992) *Plant Journal* 2(3):291-300); ALS promoter, as described in PCT Application Number WO 96/30530; and other transcription initiation regions from various plant genes known to those of skill. For the present invention ubiquitin is the preferred promoter for expression in monocot plants.

Tissue-preferred promoters can be utilized to target enhanced type A RR expression within a particular plant tissue. By "tissue-preferred" is intended to mean that expression is predominately in a particular tissue, albeit not necessarily exclusively in that tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen. Genet.* 255(3):337-353; Russell, et al., (1997) *Transgenic Res.* 6(2):157-168; Rinehart, et al., (1996) *Plant Physiol.* 112(3):1331-1351; Van Camp, et al., (1996) *Plant Physiol.* 112(2):525-535; Canevascini, et al., (1996) *Plant Physiol.* 112(2):513-525; Yamamoto, et al., (1995) *Plant Cell Physiol.* 35(5):773-778; Lam (1995) *Results Probl. Cell Differ.* 20:181-196; Orozco, et al., (1993) *Plant Mol. Biol.* 23(6):1129-1138; Matsuoka, et al., (1993) *Proc Natl. Acad. Sci. USA* 90(20):9586-9590; and Guevara-Garcia, et al., (1993) *Plant J.* 5(3):595-505. Such promoters can be modified, if necessary, for weak expression. See, also, U.S. Patent Application Number 2003/0074698, herein incorporated by reference.

A mesophyllic cell preferred promoter includes but is not limited to promoters such as known phosphoenopyruvate decarboxylase (PEPC) promoters or putative PEPC promoters from any number of species, for example, *Zea mays, Oryza sativa, Arabidopsis thaliana, Glycine max* or *Sorghum bicolor*. Examples include *Zea mays* PEPC of GenBank Accession Number gi:116268332_HTG AC190686, (SEQ ID NO: 25) and gCAT GSS composite sequence (SEQ ID NO: 30); *Oryza sativa* PEPC of GenBank Accession Number gi|208044452|dbj|AP003052.31 (SEQ ID NO: 26); *Arabidopsis thaliana* PEPC of GenBank Accession Number gi/5541653|dbj|AP000370.1|AP000370 (SEQ ID NO: 27); gi:7769847 (SEQ ID NO: 28); or gi|20198070|gb|AC007087.7 (SEQ ID NO: 29); *Glycine max* (GSS contigs) (SEQ ID NOS: 31-32); or *Sorghum bicolor* (JGI assembly scaffold_832, 89230 bp., JGI assembly scaffold_1632, SEQ ID NOS: 33-34) (1997) *Plant J.* 12(2):255-265; Kwon, et al., (1995) *Plant Physiol.* 105:357-67; Yamamoto, et al., (1995) *Plant Cell Physiol.* 35(5):773-778; Gotor, et al., (1993) *Plant J.* 3:509-18; Orozco, et al., (1993) *Plant Mol. Biol.* 23(6):1129-1138; Baszczynski, et al., (1988) *Nucl. Acid Res.* 16:5732; Mitra, et al., (1995) *Plant Molecular Biology* 26:35-93; Kayaya, et al., (1995) *Molecular and General Genetics* 258:668-675; and Matsuoka, et al., (1993) *Proc. Natl. Acad. Sci. USA* 90(20):9586-9590. Senescence regulated promoters are also of use, such as, SAM22 (Crowell, et al., (1992) *Plant Mol. Biol.* 18:559-566). See also, U.S. Pat. No. 5,589,052, herein incorporated by reference.

Shoot-preferred promoters include, shoot meristem-preferred promoters such as promoters disclosed in Weigal, et al., (1992) *Cell* 69:853-859; Accession Number AJ131822; Accession Number Z71981; Accession Number AF059870, the ZAP promoter (U.S. patent application Ser. No. 10/387, 937), the maize tb1 promoter (Wang, et al., (1999) *Nature* 398:236-239, and shoot-preferred promoters disclosed in McAvoy, et al., (2003) *Acta Hort.* (ISHS) 625:379-385.

Root-preferred promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger, et al., (1990) *Plant Mol. Biol.* 15(3):533-553 (root-specific promoter of the mannopine synthase (MAS) gene of *Agrobacterium tumefaciens*); and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-651, where two root-specific promoters isolated from hemoglobin genes from the nitrogen-fixing nonlegume *Parasponia andersonil* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):353-350). The TR1' gene, fused to nptII (neomycin phosphotransferase II) showed similar characteristics. Additional root-preferred promoters include the VfENOD-GRP3 gene promoter (Kuster, et al., (1995) *Plant Mol. Biol.* 29(5):759-772); rolB promoter (Capana, et al., (1995) *Plant Mol. Biol.* 25(5):681-691; and the CRWAQ81 root-preferred promoter with the ADH first intron (U.S. Provisional Application No. 60/509,878, filed Oct. 9, 2003, herein incorporated by reference). See also, U.S. Pat. Nos. 5,837,876; 5,750,386; 5,633,363; 5,559,252; 5,501,836; 5,110,732; and 5,023,179.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50; and An, et al., (1989) *Plant Cell* 1:115-22); and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell. Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2 and 6, the Bronze-1 intron are known in the art. See generally, *The Maize Handbook*, Chapter 116, Freeling and Walbot, eds., Springer, N.Y. (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell*, 2:301-13); signal peptides which cause proteins to be secreted, such as that of PR1b (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference), or signal peptides which target proteins to the plastids such as that of rapeseed enoyl-Acp reductase (Verwaert, et al., (1994) *Plant Mol. Biol.* 26:189-202) are useful in the invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987), *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11, and Berger, et al., (1989) *Proc. Natl. Acad. Sci. USA*, 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts. Conversely, a "strong promoter" drives expression of a coding sequence at a "high level," or about $1/10$ transcripts to about $1/100$ transcripts to about $1/1,000$ transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas ($7^{th}$ ed., 1992).

Appropriate vectors for expressing proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Other useful terminators for practicing this invention include, but are not limited to, pinII (see, An, et al., (1989) *Plant Cell* 1(1):115-122), glb1 (see, Genbank Accession Number L22345), gz (see, gzw64a terminator, Genbank Accession Number S78780), and the nos terminator from *Agrobacterium*.

Sequences for accurate splicing of the transcript may also be included. An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the NR gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert an NR polynucleotide into a plant host, including biological and physical plant transformation protocols. See, e.g., Miki, et al., (1993) "Procedure for Introducing Foreign DNA into Plants," in *Methods in Plant Molecular Biology and Biotechnology*, Glick and Thompson, eds., CRC Press, Inc., Boca Raton, pp. 67-88. The methods chosen vary with the host plant, and include chemical transfection methods such as calcium phosphate, microorganism-mediated gene transfer such as *Agrobacterium* (Horsch, et al., (1985) *Science* 227:1229-31), electroporation, micro-injection, and biolistic bombardment.

Expression cassettes and vectors and in vitro culture methods for plant cell or tissue transformation and regeneration of plants are known and available. See, e.g., Gruber, et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski, et al., (1984) *EMBO J.* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. Gamborg and Phillips. Springer-Verlag Berlin Heidelberg N.Y., 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren and Hooykaas (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. G. P. Chapman, et al., pp. 197-209. Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou and Ford, (1995) *Annals of Botany* 75:407-413 (rice); Osjoda, et al., (1996) *Nature Biotech.* 14:745-750; Agrobacterium mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185); all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. patent application Ser No. 913,914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the *Liliales* and *Arales*) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application Number 604 662 A1 discloses a method for transforming monocots using *Agrobacterium*. European Application Number 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. patent application Ser. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant*

*Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC*, A2-38, p. 53; D'Halluin, et al., (1992) *Plant Cell* 4:1495-505; and Spencer, et al., (1994) *Plant Mol. Biol.* 24:51-61.

Increasing the Activity and/or Level of a NR Polypeptide

Methods are provided to increase the activity and/or level of the NR polypeptide of the invention. An increase in the level and/or activity of the NR polypeptide of the invention can be achieved by providing to the plant a NR polypeptide. The NR polypeptide can be provided by introducing the amino acid sequence encoding the NR polypeptide into the plant, introducing into the plant a nucleotide sequence encoding a NR polypeptide or alternatively by modifying a genomic locus encoding the NR polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having enhanced nitrogen utilization activity. It is also recognized that the methods of the invention may employ a polynucleotide that is not capable of directing, in the transformed plant, the expression of a protein or an RNA. Thus, the level and/or activity of a NR polypeptide may be increased by altering the gene encoding the NR polypeptide or its promoter. See, e.g., Kmiec, U.S. Pat. No. 5,565,350; Zarling, et al., PCT/US93/03868. Therefore mutagenized plants that carry mutations in NR genes, where the mutations increase expression of the NR gene or increase the NR activity of the encoded NR polypeptide are provided.

Reducing the Activity and/or Level of a NR Polypeptide

Methods are provided to reduce or eliminate the activity of a NR polypeptide of the invention by transforming a plant cell with an expression cassette that expresses a polynucleotide that inhibits the expression of the NR polypeptide. The polynucleotide may inhibit the expression of the NR polypeptide directly, by preventing transcription or translation of the NR messenger RNA, or indirectly, by encoding a polypeptide that inhibits the transcription or translation of an NR gene encoding NR polypeptide. Methods for inhibiting or eliminating the expression of a gene in a plant are well known in the art, and any such method may be used in the present invention to inhibit the expression of NR polypeptide.

In accordance with the present invention, the expression of NR polypeptide is inhibited if the protein level of the NR polypeptide is less than 70% of the protein level of the same NR polypeptide in a plant that has not been genetically modified or mutagenized to inhibit the expression of that NR polypeptide. In particular embodiments of the invention, the protein level of the NR polypeptide in a modified plant according to the invention is less than 60%, less than 50%, less than 40%, less than 30%, less than 20%, less than 10%, less than 5%, or less than 2% of the protein level of the same NR polypeptide in a plant that is not a mutant or that has not been genetically modified to inhibit the expression of that NR polypeptide. The expression level of the NR polypeptide may be measured directly, for example, by assaying for the level of NR polypeptide expressed in the plant cell or plant, or indirectly, for example, by measuring the nitrogen uptake activity of the NR polypeptide in the plant cell or plant, or by measuring the phenotypic changes in the plant. Methods for performing such assays are described elsewhere herein.

In other embodiments of the invention, the activity of the NR polypeptides is reduced or eliminated by transforming a plant cell with an expression cassette comprising a polynucleotide encoding a polypeptide that inhibits the activity of a NR polypeptide. The enhanced nitrogen utilization activity of a NR polypeptide is inhibited according to the present invention if the NR activity of the NR polypeptide is less than 70% of the NR activity of the same NR polypeptide in a plant that has not been modified to inhibit the NR activity of that NR polypeptide. In particular embodiments of the invention, the NR activity of the NR polypeptide in a modified plant according to the invention is less than 60%, less than 50%, less than 40%, less than 30%, less than 20%, less than 10%, or less than 5% of the NR activity of the same NR polypeptide in a plant that that has not been modified to inhibit the expression of that NR polypeptide. The NR activity of a NR polypeptide is "eliminated" according to the invention when it is not detectable by the assay methods described elsewhere herein. Methods of determining the alteration of nitrogen utilization activity of a NR polypeptide are described elsewhere herein.

In other embodiments, the activity of a NR polypeptide may be reduced or eliminated by disrupting the gene encoding the NR polypeptide. The invention encompasses mutagenized plants that carry mutations in NR genes, where the mutations reduce expression of the NR gene or inhibit the nitrogen utilization activity of the encoded NR polypeptide.

Thus, many methods may be used to reduce or eliminate the activity of a NR polypeptide. In addition, more than one method may be used to reduce the activity of a single NR polypeptide.

1. Polynucleotide-Based Methods:

In some embodiments of the present invention, a plant is transformed with an expression cassette that is capable of expressing a polynucleotide that inhibits the expression of an NR polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one NR polypeptide is an expression cassette capable of producing an RNA molecule that inhibits the transcription and/or translation of at least one NR polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a NR polypeptide are given below.

i. Sense Suppression/Cosuppression

In some embodiments of the invention, inhibition of the expression of a NR polypeptide may be obtained by sense suppression or cosuppression. For cosuppression, an expression cassette is designed to express an RNA molecule corresponding to all or part of a messenger RNA encoding a NR polypeptide in the "sense" orientation. Over expression of the RNA molecule can result in reduced expression of the native gene. Accordingly, multiple plant lines transformed with the cosuppression expression cassette are screened to identify those that show the greatest inhibition of NR polypeptide expression.

The polynucleotide used for cosuppression may correspond to all or part of the sequence encoding the NR polypeptide, all or part of the 5' and/or 3' untranslated region of a NR polypeptide transcript, or all or part of both the coding sequence and the untranslated regions of a transcript encoding a NR polypeptide. In some embodiments where the polynucleotide comprises all or part of the coding region for the NR polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication Number 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323; herein incorporated by reference.

ii. Antisense Suppression

In some embodiments of the invention, inhibition of the expression of the NR polypeptide may be obtained by antisense suppression. For antisense suppression, the expression cassette is designed to express an RNA molecule complementary to all or part of a messenger RNA encoding the NR polypeptide. Over expression of the antisense RNA molecule can result in reduced expression of the native gene. Accordingly, multiple plant lines transformed with the antisense suppression expression cassette are screened to identify those that show the greatest inhibition of NR polypeptide expression.

The polynucleotide for use in antisense suppression may correspond to all or part of the complement of the sequence encoding the NR polypeptide, all or part of the complement of the 5' and/or 3' untranslated region of the NR transcript, or all or part of the complement of both the coding sequence and the untranslated regions of a transcript encoding the NR polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Publication Number 20020048814, herein incorporated by reference.

iii. Double-Stranded RNA Interference

In some embodiments of the invention, inhibition of the expression of a NR polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of NR polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of a NR polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731; and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7, and US Patent Publication Number 2003/0175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295, and US Patent Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) *EMBO J.* 19:5194-5201; Matzke, et al., (2001) *Curr. Opin. Genet. Devel.* 11:221-227; Scheid, et al., (2002) *Proc. Natl. Acad. Sci.*, USA 99:13659-13662; Aufsaftz, et al., (2002) *Proc. Nat'l. Acad. Sci.* 99(4): 16499-16506; Sijen, et al., *Curr. Biol.* (2001) 11:436-440), herein incorporated by reference.

V. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the NR polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362, and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the NR polypeptide. Thus, the polynucleotide causes the degradation of the endogenous messenger RNA, resulting in reduced expression of the NR polypeptide. This method is described, for example, in U.S. Pat. No. 4,987,071, herein incorporated by reference.

vii. Small Interfering RNA or Micro RNA

In some embodiments of the invention, inhibition of the expression of a NR polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of NR expression, the 22-nucleotide sequence is selected from a NR transcript sequence and contains 22 nucleotides of said NR sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a NR polypeptide, resulting in reduced expression of the gene. In particular embodiments, the zinc finger protein binds to a regulatory region of a NR gene. In other embodiments, the zinc finger protein binds to a messenger RNA encoding a NR polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355; each of which is herein incorporated by reference.

3. Polypeptide-Based Inhibition of Protein Activity

In some embodiments of the invention, the polynucleotide encodes an antibody that binds to at least one NR polypeptide, and reduces the enhanced nitrogen utilization activity of the NR polypeptide. In another embodiment, the binding of the antibody results in increased turnover of the antibody-NR complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of a NR polypeptide is reduced or eliminated by disrupting the gene encoding the NR polypeptide. The gene encoding the NR polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced nitrogen utilization activity.

i. Transposon Tagging

In one embodiment of the invention, transposon tagging is used to reduce or eliminate the NR activity of one or more NR polypeptide. Transposon tagging comprises inserting a transposon within an endogenous NR gene to reduce or eliminate expression of the NR polypeptide. "NR gene" is intended to mean the gene that encodes a NR polypeptide according to the invention.

In this embodiment, the expression of one or more NR polypeptide is reduced or eliminated by inserting a transposon within a regulatory region or coding region of the gene encoding the NR polypeptide. A transposon that is within an exon, intron, 5' or 3' untranslated sequence, a promoter, or any other regulatory sequence of a NR gene may be used to reduce or eliminate the expression and/or activity of the encoded NR polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540; and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (enhanced nitrogen utilization activity) of the encoded protein are well known in the art. Insertional mutations in gene exons usually result in null-mutants. Mutations in conserved residues are particularly effective in inhibiting the activity of the encoded protein. Conserved residues of plant NR polypeptides suitable for mutagenesis with the goal to eliminate NR activity have been described. Such mutants can be isolated according to well-known procedures, and mutations in different NR loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more NR polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

iii. Modulating Nitrogen Utilization Activity

In specific methods, the level and/or activity of a NR regulator in a plant is decreased by increasing the level or activity of the NR polypeptide in the plant. The increased expression of a negative regulatory molecule may decrease the level of expression of downstream one or more genes responsible for an improved NR phenotype.

Methods for increasing the level and/or activity of NR polypeptides in a plant are discussed elsewhere herein. Briefly, such methods comprise providing a NR polypeptide of the invention to a plant and thereby increasing the level and/or activity of the NR polypeptide. In other embodiments, a NR nucleotide sequence encoding a NR polypeptide can be provided by introducing into the plant a polynucleotide comprising a NR nucleotide sequence of the invention, expressing the NR sequence, increasing the activity of the NR polypeptide, and thereby decreasing the number of tissue cells in the plant or plant part. In other embodiments, the NR nucleotide construct introduced into the plant is stably incorporated into the genome of the plant.

In other methods, the growth of a plant tissue is increased by decreasing the level and/or activity of the NR polypeptide in the plant. Such methods are disclosed in detail elsewhere herein. In one such method, a NR nucleotide sequence is introduced into the plant and expression of said NR nucleotide sequence decreases the activity of the NR polypeptide, and thereby increasing the tissue growth in the plant or plant part. In other embodiments, the NR nucleotide construct introduced into the plant is stably incorporated into the genome of the plant.

As discussed above, one of skill will recognize the appropriate promoter to use to modulate the level/activity of a NR in the plant. Exemplary promoters for this embodiment have been disclosed elsewhere herein.

In other embodiments, such plants have stably incorporated into their genome a nucleic acid molecule comprising a NR nucleotide sequence of the invention operably linked to a promoter that drives expression in the plant cell.

iv. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development, or radial expansion.

Methods for modulating root development in a plant are provided. The methods comprise modulating the level and/or activity of the NR polypeptide in the plant. In one method, a NR sequence of the invention is provided to the plant. In another method, the NR nucleotide sequence is provided by introducing into the plant a polynucleotide comprising a NR nucleotide sequence of the invention, expressing the NR sequence, and thereby modifying root development. In still other methods, the NR nucleotide construct introduced into the plant is stably incorporated into the genome of the plant.

In other methods, root development is modulated by altering the level or activity of the NR polypeptide in the plant. A change in NR activity can result in at least one or more of the following alterations to root development, including, but not limited to, alterations in root biomass and length.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by decreasing the activity and/or level of the NR polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by altering the level and/or activity of the NR polypeptide also finds use in promoting in vitro propagation of explants.

Furthermore, higher root biomass production due to NR activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has an increased level/activity of the NR polypeptide of the invention and has enhanced root growth and/or root biomass. In other embodiments, such plants have stably incorporated into their genome a nucleic acid molecule comprising a NR nucleotide sequence of the invention operably linked to a promoter that drives expression in the plant cell.

v. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length, and leaf senescence.

As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant comprises modulating the activity and/or level of a NR polypeptide of the invention. In one embodiment, a NR sequence of the invention is provided. In other embodiments, the NR nucleotide sequence can be provided by introducing into the plant a polynucleotide comprising a NR nucleotide sequence of the invention, expressing the NR sequence, and thereby modifying shoot and/or leaf development. In other embodiments, the NR nucleotide construct introduced into the plant is stably incorporated into the genome of the plant.

In specific embodiments, shoot or leaf development is modulated by altering the level and/or activity of the NR polypeptide in the plant. A change in NR activity can result in at least one or more of the following alterations in shoot and/or leaf development, including, but not limited to, changes in leaf number, altered leaf surface, altered vasculature, internodes and plant growth, and alterations in leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, and leaf-preferred promoters. Exemplary promoters have been disclosed elsewhere herein.

Increasing NR activity and/or level in a plant results in altered internodes and growth. Thus, the methods of the invention find use in producing modified plants. In addition, as discussed above, NR activity in the plant modulates both root and shoot growth. Thus, the present invention further provides methods for altering the root/shoot ratio. Shoot or leaf development can further be modulated by altering the level and/or activity of the NR polypeptide in the plant.

Accordingly, the present invention further provides plants having modulated shoot and/or leaf development when compared to a control plant. In some embodiments, the plant of the invention has an increased level/activity of the NR polypeptide of the invention. In other embodiments, the plant of the invention has a decreased level/activity of the NR polypeptide of the invention.

vi. Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the NR polypeptide has not been modulated. "Modulating floral development" further includes any alteration in the timing of the development of a plant's reproductive tissue (i.e., a delayed or a accelerated timing of floral development) when compared to a control plant in which the activity or level of the NR polypeptide has not been modulated. Macroscopic alterations may include changes in size, shape, number, or location of reproductive organs, the developmental time period that these structures form, or the ability to maintain or proceed through the flowering process in times of environmental stress. Microscopic alterations may include changes to the types or shapes of cells that make up the reproductive organs.

The method for modulating floral development in a plant comprises modulating NR activity in a plant. In one method, a NR sequence of the invention is provided. A NR nucleotide sequence can be provided by introducing into the plant a polynucleotide comprising a NR nucleotide sequence of the invention, expressing the NR sequence, and thereby modifying floral development. In other embodiments, the NR nucleotide construct introduced into the plant is stably incorporated into the genome of the plant.

In specific methods, floral development is modulated by increasing the level or activity of the NR polypeptide in the plant. A change in NR activity can result in at least one or more of the following alterations in floral development, including, but not limited to, altered flowering, changed number of flowers, modified male sterility, and altered seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S11-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters, and inflorescence-preferred promoters.

In other methods, floral development is modulated by altering the level and/or activity of the NR sequence of the invention. Such methods can comprise introducing a NR nucleotide sequence into the plant and changing the activity of the NR polypeptide. In other methods, the NR nucleotide construct introduced into the plant is stably incorporated into the genome of the plant. Altering expression of the NR sequence of the invention can modulate floral development during periods of stress. Such methods are described elsewhere herein. Accordingly, the present invention further provides plants having modulated floral development when compared to the floral development of a control plant. Compositions include plants having a altered level/activity of the NR polypeptide of the invention and having an altered floral development. Compositions also include plants having a modified level/activity of the NR polypeptide of the invention wherein the plant maintains or proceeds through the flowering process in times of stress.

Methods are also provided for the use of the NR sequences of the invention to increase seed size and/or weight. The method comprises increasing the activity of the NR sequences in a plant or plant part, such as the seed. An increase in seed size and/or weight comprises an increased size or weight of the seed and/or an increase in the size or weight of one or more seed part including, for example, the embryo, endosperm, seed coat, aleurone, or cotyledon.

As discussed above, one of skill will recognize the appropriate promoter to use to increase seed size and/or seed weight. Exemplary promoters of this embodiment include constitutive promoters, inducible promoters, seed-preferred promoters, embryo-preferred promoters, and endosperm-preferred promoters.

The method for altering seed size and/or seed weight in a plant comprises increasing NR activity in the plant. In one embodiment, the NR nucleotide sequence can be provided by introducing into the plant a polynucleotide comprising a NR nucleotide sequence of the invention, expressing the NR sequence, and thereby decreasing seed weight and/or size. In other embodiments, the NR nucleotide construct introduced into the plant is stably incorporated into the genome of the plant.

It is further recognized that increasing seed size and/or weight can also be accompanied by an increase in the speed of growth of seedlings or an increase in early vigor. As used herein, the term "early vigor" refers to the ability of a plant to grow rapidly during early development, and relates to the successful establishment, after germination, of a well-developed root system and a well-developed photosynthetic apparatus. In addition, an increase in seed size and/or weight can also result in an increase in plant yield when compared to a control.

Accordingly, the present invention further provides plants having an increased seed weight and/or seed size when compared to a control plant. In other embodiments, plants having an increased vigor and plant yield are also provided. In some embodiments, the plant of the invention has a modified level/activity of the NR polypeptide of the invention and has an increased seed weight and/or seed size. In other embodiments, such plants have stably incorporated into their genome a nucleic acid molecule comprising a NR nucleotide sequence of the invention operably linked to a promoter that drives expression in the plant cell.

vii. Method of Use for NR Polynucleotide, Expression Cassettes, and Additional Polynucleotides The nucleotides, expression cassettes and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885, 801; 5,885,802; and 5,703,409); barley high lysine (Williamson, et al., (1987) *Eur. J. Biochem.* 165:99-106; and WO 98/20122); and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. patent application Ser. No. 10/053,410, filed Nov. 7, 2001); and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262: 1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem.* 27:16749-16752, Arredondo-Peter, et al., (1997) *Plant Physiol.* 115: 1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference); and rice (Musumura, et al., (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser, et al., (1986) *Gene* 48:109); and the like.

Genes encoding disease resistance traits include detoxification genes, such as against fumonosin (U.S. Pat. No. 5,792, 931); avirulence (avr) and disease resistance (R) genes (Jones, et al., (1994) *Science* 266:789; Martin, et al., (1993) *Science* 262:1432; and Mindrinos, et al., (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

Isolation of NR Sequences 20,778 *Porphyra yezoensis* ESTs were identified in Genbank then downloaded. The dataset was converted to fasta, formatted for BLAST algorithm searching, and searched with maize nitrate reductase as the query.

Multiple ESTs likely encoding fragments of nitrate reductase genes were identified, and EST contigs were built, supplemented by 5'- and 3'-directional EST walking and final contig assembly of the gene transcript region. Prior to this contig assembly the gene and its coding region existed in the public databases as short EST sequences representing merely fragments of the gene. The resulting *Porphyra yezoensis* nitrate reductase transcript contig represented a 5'UTR, the N-terminus, and all but the last (C-terminal) 167 codons of the peptide.

Assuming the two strains of *Porphyra* were closely related organisms, oligonucleotide primers were designed from the assembled *Porphyra yezoensis* nitrate reductase gene with sense: attgtggtgcacaacaaggtgtatga (SEQ ID NO: 13) and anti-sense primers: tcggcttccacatgttcctg (SEQ ID NO: 14). These primers were used to amplify a 448 bp internal region of the gene using *Porphyra perforata* genomic DNA. A Genome Walking kit from Bio S&T (Montreal, Quebec, Canada) was then used to determine both ends of the gene, walking out from the internal fragment. (Standard conditions for nested PCR, ligation and digestion as per the provided SOP from Bio S&T were used). For the *Porphyra perforata* gene discovery, the following walking primers were designed—ccgtgtacctc-cgcaactct (SEQ ID NO: 15), gctgcactttgtgcgcaacc (SEQ ID NO: 16), gcatgggacgagggcaacaa (SEQ ID NO: 17), gcttgc-ccgtcggcttccacatgtt (SEQ ID NO: 18), catcgaaggctccatggt-catgcg (SEQ ID NO: 19) and ctacacgccaacgtcgtctgacgca (SEQ ID NO: 20).

Again assuming the *Porphyra* were closely related organisms, *Porphyra perforata* primers for full length nitrate reductase were used to amplify the gene from the closely related *Porphyra yezoensis* red algae, but with a lower annealing temperature of 52° C. in the initial PCR set-up for 40 cycles. Regions were sequence verified as correct, then using the same Genome Walking kit from Bio S&T ambiguous regions and the remaining ends of the *Porphyra yezoensis* along with associated untranslated regions were determined.

The entire ORF of the nitrate reductase gene from both species was cloned as a large PCR product using a high-fidelity Taq polymerase and a minimal of at least three independent clones was used to verify the correct internal sequence. The ORF of the *Porphyra perforata* nitrate reductase gene was amplified with sense: catggaggctgcttctggtgc (SEQ ID NO: 21) and anti-sense primers: tcaacgagctgct-tgtgggca (SEQ ID NO: 22). The ORF of the *Porphyra yezoensis* nitrate reductase gene was amplified with sense: cccatcac-cgcacagccga (SEQ ID NO: 23) and anti-sense primers: agagaggcgccccttgcatgtt (SEQ ID NO: 24). For most regions of the gene, more clones were used to validate the full-length sequence. Protein and nucleotide alignments confirmed that both genes were closely associated and had many conserved protein residues when compared to other nitrate reductase enzymes. There are no introns for either Nitrate Reductase coding DNA sequence.

Example 2

*Pichia Pastoris* Expression Vectors and Yeast Transformation

*Pichia pastoris* is a non-nitrate assimilating yeast and requires both functional nitrate transporter and nitrate reductase to uptake nitrate (Unkles, et al., (2004) *J. Biol. Chem.* 279:28182-28186). *P. pastoris* has been used as a model system for identification and characterization of nitrate reductases and/or plant nitrate transporters. The nitrate reductase activity can be determined in vitro or in vivo when a nitrate transporter gene was co-expressed. The wild type nitrate reductase genes from *Porphyra performa* (PpNR) and *Porphyra yezoensis* (PyNR) driven by a yeast constitutive promoter (GAP promoter, glyceraldehydes-3-phosphate dehydrogenase) was integrated into AOX1 locus of *P. pastoris* stain KM71 carrying a yeast nitrate transporter gene (YNT1).

Details: YNT1 (nitrate transporter from *Pichia angusta*) driven by GAP promoter (vector: p3.5GAP-YNT1) was integrated into *P. pastoris* strain KM71 genome at His4 locus to generate YNT1-containing lines. After the YNT1-containing lines were confirmed by PCR, PpNR or PyNR driven by GAP promoter was integrated into the genome at AOX1 locus (vectors: PAOXGAP-PPNR and PAOXGAP-PYNR). (*Pichia* transformation kit is from Invitrogen. Both expression vector backbones were modified based on the versions from Invitrogen.)

Functional expression in *P. pastoris*: Recombinant KM71 transformed with p3.5GAP-YNT1 and/or PAOXGAP-PPNR, PAOXGAP-PYNR were screened for NR activity. Transformants were cultured in rich media (YPD) at 30° C. for overnight. Yeast cells were collected and washed with water twice then re-suspended in 20 uM MOPS, pH6.5 and 1% glucose containing 1 mM $NaNO_3$. After 2 hours incubation at 30° C., the supernatant was collected for nitrite assay with 2% and 2%. The Vmax of PpNR is 70-80× higher than Py-NR. The transformants containing PpNR showed much stronger nitrate reductase activity than PyNR in *P. pastoris* in vivo.

Kinetics in *P. Pastoris*: The nitrite concentration of *P. pastoris* KM71-containing YNT1 and PpNR line incubated with different nitrate concentration from 0-30 mM at three pH, pH5.5, 6.5, and 7.5 was assayed in vivo. PpNR has better Vmax at pH6.5. The Km is about 30-40 μM. This data match the predicted results (published PyNR with Km 64 μM). At the same time, maize NR, ZM-NR, and yeast NR from *P. angusta*, YNR1, were assayed at similar conditions. The Km of ZM-NR is about 300 uM and YNR1 has Km about 200-400

μM. They also have the better Vmax at pH6.5. The PpNR is an efficient NR with Km 10× lower than others.

Example 3

PpNR and PyNR Mutants

To maintain high level of active form of PPNR in transgenic plants, the serine residue in a putative phosphorylation motif R/K-S/T-X-pS-X-P (*J. of Experimental Botany* (2004) 55:1275-1282) at position 561 will be mutated to either alanine (S561A mutant, sequence provided) or aspartic acid (S561D mutant). The mutated PPNRs will be generated in *P. pastoris* and tested in YNT1-carrying line for NR activity as described before. The functional S561A or S561 D will be expressed in transgenic plants driven by a constitutive promoter or a mesophyll preferred promoter. The NR activity will be tested during light/dark transitions. Other putative post-translational regions such as N-terminal region of PPNR may be modified or deleted to de-regulate by light at post-translational level.

Example 4

Transformation and Regeneration of Transgenic Plants

Immature maize embryos from greenhouse donor plants are bombarded with a plasmid containing the NR sequence operably linked to the drought-inducible promoter RAB17 promoter (Vilardell, et al., (1990) *Plant Mol Biol* 14:423-432) and the selectable marker gene PAT, which confers resistance to the herbicide Bialaphos. (Miller, et al., (2000) *Biochimica et Biophysica Acta* 1465:343-358). Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the NR sequence operably linked to an ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water

10 μl (1 μg) DNA in Tris EDTA buffer (1 μg total DNA)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in a particle gun. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel-earring capacity yields under drought conditions when compared to control maize plants under identical environmental conditions. Alternatively, the transformed plants can be monitored for a modulation in meristem development (i.e., a decrease in spikelet formation on the ear). See, for example, Bruce, et al., (2002) *Journal of Experimental Botany* 53:1-13.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-1 $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Example 5

Agrobacterium-Mediated Transformation

For Agrobacterium-mediated transformation of maize with an antisense sequence of the NR sequence of the present invention, preferably the method of Zhao is employed (U.S. Pat. No. 5,981,840, and PCT Patent Application Publication WO98/32326; the contents of which are hereby incorporated by reference). Briefly, immature embryos are isolated from maize and the embryos contacted with a suspension of Agrobacterium, where the bacteria are capable of transferring the antisense NR sequences to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Plants are monitored and scored for a modulation in meristem development (for instance, alterations of size and appearance of the shoot and floral meristems and/or increased yields of leaves, flowers, and/or fruits).

Example 6

Soybean Embryo Transformation

Soybean embryos are bombarded with a plasmid containing an antisense NR sequences operably linked to an ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188), and the 3' region of the nopaline synthase gene from the T-DNA of the Ti plasmid of Agrobacterium tumefaciens. The expression cassette comprising an antisense NR sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Sunflower Meristem Tissue Transformation

Sunflower meristem tissues are transformed with an expression cassette containing an antisense NR sequences operably linked to a ubiquitin promoter as follows (see also, European Patent Number EP 0 486233, herein incorporated by reference, and Malone-Schoneberg, et al., (1994) Plant Science 103:199-207). Mature sunflower seed (Helianthus annuus L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer, et al. (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.,* 15:473-497), Shepard's vitamin additions (Shepard, (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS1000® particle acceleration device.

Disarmed *Agrobacterium tumefaciens* strain EHA105 is used in all transformation experiments. A binary plasmid vector comprising the expression cassette that contains the NR gene operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of contiNRd development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by NR activity analysis of leaf extracts while transgenic seeds harvested from NPTII-positive $T_0$ plants are identified by NR activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at $OD_{600}$. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive explants are identified, those shoots that fail to exhibit modified NR activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for modified NR expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 8

Rice Tissue Transformation

Genetic Confirmation of the NR Gene

One method for transforming DNA into cells of higher plants that is available to those skilled in the art is high-velocity ballistic bombardment using metal particles coated with the nucleic acid constructs of interest (see, Klein, et al., Nature (1987) (London) 327:70-73, and see, U.S. Pat. No. 4,945,050). A Biolistic PDS-1000/He (BioRAD Laboratories, Hercules, Calif.) is used for these complementation experiments. The particle bombardment technique is used to transform the NR mutants and wild type rice with DNA fragments The bacterial hygromycin B phosphotransferase (Hpt II) gene from *Streptomyces hygroscopicus* that confers resistance to the antibiotic is used as the selectable marker for rice transformation. In the vector, pML18, the Hpt II gene was engineered with the 35S promoter from Cauliflower Mosaic Virus and the termination and polyadenylation signals from the octopine synthase gene of *Agrobacterium tumefaciens*. pML18 was described in WO 97/47731, which was published on Dec. 18, 1997, the disclosure of which is hereby incorporated by reference.

Embryogenic callus cultures derived from the scutellum of germinating rice seeds serve as source material for transformation experiments. This material is generated by germinating sterile rice seeds on a callus initiation media (MS salts, Nitsch and Nitsch vitamins, 1.0 mg/l 2,4-D and 10 μM AgNO$_3$) in the dark at 27-28° C. Embryogenic callus proliferating from the scutellum of the embryos is the transferred to CM media (N6 salts, Nitsch and Nitsch vitamins, 1 mg/l 2,4-D, Chu, et al., 1985, *Sci. Sinica* 18: 659-668). Callus cultures are maintained on CM by routine sub-culture at two week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate.

Each genomic DNA fragment is co-precipitated with pML18 containing the selectable marker for rice transformation onto the surface of gold particles. To accomplish this, a total of 10 μg of DNA at a 2:1 ratio of trait:selectable marker DNAs are added to 50 μl aliquot of gold particles that have been resuspended at a concentration of 60 mg ml$^{-1}$. Calcium chloride (50 μl of a 2.5 M solution) and spermidine (20 μl of a 0.1 M solution) are then added to the gold-DNA suspension as the tube is vortexing for 3 min. The gold particles are centrifuged in a microfuge for 1 sec and the supernatant removed. The gold particles are then washed twice with 1 ml of absolute ethanol and then resuspended in 50 μl of absolute ethanol and sonicated (bath sonicator) for one second to disperse the gold particles. The gold suspension is incubated at −70° C. for five minutes and sonicated (bath sonicator) if needed to disperse the particles. Six μl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Two to four plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates are incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus is transferred to RM2 media (MS salts, Nitsch and Nitsch vitamins, 3% sucrose, 0.4% gelrite+50 ppm hyg B) and placed under cool white light (~40 μm$^{-2}$s$^{-1}$) with a 12 hr photoperiod at 25° C. and 30-40% humidity. After 2-4 weeks in the light, callus begin to organize, and form shoots. Shoots are removed from surrounding callus/media and gently transferred to RM3 media (½×MS salts, Nitsch and Nitsch vitamins, 1% sucrose+50 ppm hygromycin B) in phytatrays (Sigma Chemical Co., St. Louis, Mo.) and incubation is contiNRd using the same conditions as described in the previous step.

Plants are transferred from RM3 to 4" pots containing Metro mix 350 after 2-3 weeks, when sufficient root and shoot growth have occurred. The seed obtained from the transgenic plants is examined for genetic complementation of the NR mutation with the wild-type genomic DNA containing the NR gene.

Example 9

Variants of NR Sequences

A. Variant Nucleotide Sequences of NR that do not Alter the Encoded Amino Acid Sequence The NR nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequences of the variants are altered, the amino acid sequences encoded by the open reading frames do not change.

B. Variant Amino Acid Sequences of NR Polypeptides

Variant amino acid sequences of the NR polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method.

C. Additional Variant Amino Acid Sequences of NR Polypeptides

In this example, artificial protein sequences are created having 80%, 85%, 90%, and 95% identity relative to the reference protein sequence. This latter effort requires identifying conserved and variable regions from the alignment and then the judicious application of an amino acid substitutions table. These parts will be discussed in more detail below.

Largely, the determination of which amino acid sequences are altered is made based on the conserved regions among NR protein or among the other NR polypeptides. Based on the sequence alignment, the various regions of the NR polypeptide that can likely be altered are represented in lower case letters, while the conserved regions are represented by capital letters. It is recognized that conservative substitutions can be made in the conserved regions below without altering function. In addition, one of skill will understand that functional variants of the NR sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 2.

TABLE 2

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the NR polypeptides are generating having about 80%, 85%, 90% and 95% amino acid identity to the starting ORF nucleotide sequence of SEQ ID NO: 1, 2, 3, 4, 5 or 6.

Example 10

Transgenic Maize Plants $T_0$ transgenic maize plants containing the NR construct under the control of a promoter were generated. To improve nitrate assimilation, PPNR and PYNR driven by constitutive promoter (ZM-UBI) and tissue-specific promoter (ZM-NR) (4 constructs) were transformed in transgenic maize plants via *Agrobacteria*.

These plants were grown in greenhouse conditions, under the FASTCORN system, as detailed in US Patent Application Publication Number 2003/0221212, U.S. patent application Ser. No. 10/367,417.

Each of the plants was analyzed for measurable alteration in one or more of the following characteristics in the following manner:

$T_1$ progeny derived from cross fertilization each $T_0$ plant containing a single copy of each NR construct that were found to segregate 1:1 for the transgenic event were analyzed for improved growth rate in low (1 mM) $KNO_3$. Growth was monitored up to anthesis when cumulative plant growth, growth rate and ear weight were determined for transgene positive, transgene null, and non-transformed controls events. The distribution of the phenotype of individual plants was compared to the distribution of a control set and to the distribution of all the remaining treatments. Transgenic means were compared to the grand mean, the block mean in which the transgene resides and the corresponding transgenic null mean and tested for statistical significance using a Students' t-test. Variances for each set were calculated and used as the denominator of the Student's t-test after adjustment for the number of observations in each mean compared ie: Student's t test=(transgene mean−transgenic null mean)/Sqr (variance*(1/number of observations of transgene mean+1/number of observations of transgene null mean)). The probability of obtaining the calculated Student's t-test at random was calculated based on the magnitude of the Student's t-test and the number of degrees of freedom associated with the variance. A probability of 0.1 (1 chance in 10 of obtaining the result at random) or lower was used to indicate a significant response to $KNO_3$ fertility.

Example 11

Transgenic Event Analysis from Field Plots

Transgenic events are evaluated in field plots where yield is limited by reducing fertilizer application by 30% or more. Transgenic maize will be grown hydroponically. Improvements in yield, yield components, or other agronomic traits between transgenic and non-transgenic plants in these reduced nitrogen fertility plots are used to assess improvements in nitrogen utilization contributed by expression of transgenic events.

The rate of nitrate removal from hydroponics medium, the nitrate, and total nitrogen level in the plant may be determined using routine techniques. Nitrate levels in the growth medium will be monitored and compared to the nitrate levels in the growth medium of transgenic nulls. The rate of nitrate loss from the medium is an indication of nitrate utilization efficiency. Plant samples will be dried, ground and nitrate extracted and quantified. Total N will be determined in the tissue by micro-Kjeldahl. (Yasuhura and Nokihara (2001) "High-Throughput Analysis of Total Nitrogen Content that Replaces Classic Kjeldahl Method" *J Agric Food Chem* 49:4581-4583). Comparisons are made in plots supplemented with recommended nitrogen fertility rates. Effective transgenic events are those that achieve similar yields in the nitrogen-limited and normal nitrogen experiments.

Example 12

Maize Backcross Analysis

Segregating $T_4$ backcrosses to Gaspe-3 were grown in nutrient solutions containing 1 or 2 mM $KNO_3$ as the sole nitrogen source till anthesis. Leaf color (SPAD), stem diameter, vegetative and ear dry weight were determined and compared to the corresponding segregating null plants. There were 9 replicates of all treatments. Results for the plants containing the PpNR transgene showed statistically significant (at 0.001 level) improvement in ear dry weight (at both 1 and 2 mM $KNO_3$ concentrations) in comparison to non-transgenic control plants. At 2 mM $KNO_3$, there were also statistically significant improvements noted in SPAD, ear dry weight and total dry weight, as compared to non-transgenic control plants. This demonstrates the gene is stable after 5 cycles of backcrossing.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. An isolated polynucleotide comprising a member selected from the group consisting of:
    (a) a nitrate reductase (NR) polynucleotide that encodes the polypeptide of SEQ ID NO:7;
    (b) a nitrate reductase (NR) polynucleotide comprising the sequence set forth in SEQ ID NO:1;
    (c) a nitrate reductase (NR) polynucleotide having at least 95% sequence identity to SEQ ID NO:1, wherein the % sequence identity is based on the entire encoding region and is determined by BLAST 2.0 under default parameters wherein the polynucleotide encodes a polypeptide having nitrate reductase (NR) activity; and
    (d) a polynucleotide fully complementary to the polynucleotide of any one of (a) to (c).

2. The isolated polynucleotide according to claim 1 that encodes a NR polypeptide that confers increased yield or nitrogen utilization efficiency to transformed plants as compared to non-transformed control plants, when grown under limiting nitrogen conditions.

3. A vector comprising at least one polynucleotide of claim 1.

4. An expression cassette comprising at least one polynucleotide of claim 1 operably linked to a promoter, wherein the polynucleotide is in sense orientation.

5. A host cell into which is introduced at least one expression cassette of claim 4.

6. The host cell of claim 5 that is a plant cell.

7. A transgenic plant comprising at least one expression cassette of claim 4.

8. The transgenic plant of claim 7, wherein the plant is selected from the group consisting of: corn, soybean, sunflower, sorghum, canola, wheat, alfalfa, cotton, rice, barley and millet.

9. A transgenic seed from the transgenic plant of claim 7.

10. The seed of claim 9, wherein the seed is corn, soybean, sunflower, sorghum, canola, wheat, alfalfa, cotton, rice, barley or millet.

11. A recombinant expression cassette comprising a polynucleotide operably linked to a promoter, wherein the polynucleotide encodes a polypeptide that has at least 95% sequence identity to SEQ ID NO: 7, and wherein the polypeptide has NR activity.

12. A transformed host cell comprising the polynucleotide of claim 11.

13. The host cell of claim 12, wherein the host cell is a transformed plant cell.

14. The plant cell of claim 13, wherein the plant cell is selected from the group consisting of sorghum, maize, rice, wheat, soybean, sunflower, canola, alfalfa, barley and millet.

15. A transformed plant regenerated from the plant cell of claim 13.

16. The plant of claim 15, wherein the plant is sorghum, maize, rice, wheat, soybean, sunflower, canola, alfalfa, barley or millet.

17. A transformed seed of the plant of claim 15.

* * * * *